(12) United States Patent
Chang et al.

(10) Patent No.: US 12,138,281 B2
(45) Date of Patent: Nov. 12, 2024

(54) METHODS OF TREATING CHRONIC INFLAMMATORY DISEASES

(71) Applicant: METIMEDI PHARMACEUTICALS CO., LTD., Uiwang-si (KR)

(72) Inventors: Chong-Hwan Chang, Incheon (KR); Keun-Yeong Jeong, Seoul (KR)

(73) Assignee: METIMEDI PHARMACEUTICALS CO., LTD., Uiwang-si (KR)

(*) Notice: Subject to any disclaimer, the term of this patent is extended or adjusted under 35 U.S.C. 154(b) by 0 days.

(21) Appl. No.: 18/314,442

(22) Filed: May 9, 2023

(65) Prior Publication Data
US 2023/0302046 A1  Sep. 28, 2023

Related U.S. Application Data

(63) Continuation of application No. 17/131,820, filed on Dec. 23, 2020, now Pat. No. 11,684,635, which is a continuation of application No. 16/942,757, filed on Jul. 29, 2020, now Pat. No. 10,898,514, which is a continuation of application No. 16/246,252, filed on Jan. 11, 2019, now Pat. No. 10,751,365.

(60) Provisional application No. 62/616,923, filed on Jan. 12, 2018.

(51) Int. Cl.
| | |
|---|---|
| A61K 33/06 | (2006.01) |
| A61K 9/00 | (2006.01) |
| A61K 31/19 | (2006.01) |
| A61K 47/36 | (2006.01) |
| A61P 1/16 | (2006.01) |
| A61P 9/10 | (2006.01) |
| A61P 25/16 | (2006.01) |
| A61P 25/28 | (2006.01) |
| A61P 29/00 | (2006.01) |

(52) U.S. Cl.
CPC ............ *A61K 33/06* (2013.01); *A61K 9/00* (2013.01); *A61K 31/19* (2013.01); *A61K 47/36* (2013.01); *A61P 1/16* (2018.01); *A61P 9/10* (2018.01); *A61P 25/16* (2018.01); *A61P 25/28* (2018.01); *A61P 29/00* (2018.01)

(58) Field of Classification Search
None
See application file for complete search history.

(56) References Cited

U.S. PATENT DOCUMENTS

| | | | |
|---|---|---|---|
| 5,916,880 A | 6/1999 | Bar-Shalom et al. | |
| 5,958,436 A | 9/1999 | Hahn et al. | |
| 5,980,863 A | 11/1999 | Hamish et al. | |
| 6,036,985 A | 3/2000 | Jacobson et al. | |
| 6,261,610 B1 | 7/2001 | Sher et al. | |
| 6,306,902 B1 | 10/2001 | Anderson et al. | |
| 6,812,215 B2 | 11/2004 | Bushholz et al. | |
| 6,946,151 B2 | 9/2005 | Chatterji | |
| 7,309,502 B2 | 12/2007 | Zhao | |
| 7,323,439 B2 | 1/2008 | Crabtree et al. | |
| 7,358,277 B2 | 4/2008 | Krauskopf et al. | |
| 7,423,063 B2 | 9/2008 | Bartorelli | |
| 8,105,086 B2 | 1/2012 | Asgary | |
| 8,444,958 B2 | 5/2013 | Kamasaka et al. | |
| 8,518,459 B2 | 8/2013 | Wahli et al. | |
| 9,295,677 B2 | 3/2016 | Ling et al. | |
| 9,592,202 B2 | 3/2017 | Poxon et al. | |
| 9,839,644 B2 | 12/2017 | Kumar | |
| 9,931,365 B2 | 4/2018 | Geng | |
| 2002/0106396 A1 | 8/2002 | Herzog et al. | |
| 2002/0147296 A1 | 10/2002 | Teller | |
| 2003/0203040 A1 | 10/2003 | Cleland et al. | |
| 2004/0253323 A1 | 12/2004 | Giles | |
| 2005/0148661 A1 | 7/2005 | Gamelin et al. | |
| 2005/0245612 A1 | 11/2005 | Blass | |
| 2006/0115538 A1 | 6/2006 | Krauskopf et al. | |
| 2006/0165784 A1 | 7/2006 | Zhao | |
| 2007/0292493 A1 | 12/2007 | Brierre | |
| 2008/0085248 A1 | 4/2008 | Sela | |
| 2009/0285909 A1 | 11/2009 | Leverve | |
| 2010/0015068 A1 | 1/2010 | Karp et al. | |
| 2012/0064178 A1 | 3/2012 | Dean et al. | |
| 2012/0083531 A1 | 4/2012 | Clarke et al. | |
| 2013/0164338 A1* | 6/2013 | Lipp | A61M 15/00 424/680 |
| 2013/0296314 A1 | 11/2013 | Borody et al. | |
| 2015/0057332 A1 | 2/2015 | Tedgui et al. | |
| 2015/0366908 A1 | 12/2015 | Pomrink et al. | |
| 2016/0271085 A1 | 9/2016 | Goldberg | |
| 2016/0374381 A1 | 12/2016 | Mine et al. | |

(Continued)

FOREIGN PATENT DOCUMENTS

| | | |
|---|---|---|
| CA | 103230409 A | 8/2013 |
| CN | 101584889 A | 11/2009 |

(Continued)

OTHER PUBLICATIONS

Arican, 0. et al., "Serum levels of TNF-a, IFN-y, IL-6, IL-8, IL-12, IL-17, and IL-18 in Patients With Active Psoriasis and Correlation With Disease Severity," Mediators of Inflammation '12005:273-9 (2005), Hindawi Publishing Corporation.

Barnes, P.J. et al., "Nuclear factor-KB—A Pivotal Transcription Factor in Chronic Inflammatory Diseases," The New England Journal of Medicine 336: 1066-1071 (1997), Massachusetts Medical Society.

Benizri, E. et al., "The magic of the hypoxia-signaling cascade," Cellular and Molecular Life Sciences 65: 1133-1149 (2008), SP Birkhauser Verlag Basel, Switzerland.

Blanco, P. et al, "Dendritic cells and cytokines in human inflammatory and autoimmune diseases," Cytokine & Growth Factor Reviews 19:41-52 (2008), Elsevier Ltd., The Netherlands.

Bronner, F. et al., "Nutritional Aspects of Calcium Absorption," The Journal of Nutrition pp. 9-12 (1999), American Society for Nutritional Services.

(Continued)

*Primary Examiner* — Brian J Davis
(74) *Attorney, Agent, or Firm* — ArentFox Schiff LLP

(57) ABSTRACT

The invention relates to method of treating chronic inflammatory diseases in subjects in need thereof by administering calcium lactate as an active agent. The calcium lactate can be provided in a pharmaceutical, food, or nutrient composition.

9 Claims, 32 Drawing Sheets

(56) References Cited

U.S. PATENT DOCUMENTS

| | | | |
|---|---|---|---|
| 2017/0014366 | A1 | 1/2017 | Osterloh et al. |
| 2017/0304564 | A1 | 10/2017 | DeHaan et al. |
| 2017/0360727 | A1 | 12/2017 | Kim et al. |
| 2018/0008538 | A1 | 1/2018 | Izquierdo Torres et al. |

FOREIGN PATENT DOCUMENTS

| | | |
|---|---|---|
| CN | 103110133 A | 5/2013 |
| CN | 103535580 A | 1/2014 |
| EP | 1129715 A | 2/2000 |
| EP | 2599477 A | 6/2013 |
| EP | 2799060 A | 11/2014 |
| KR | 100941210 B1 | 2/2010 |
| KR | 1020120121196 A | 11/2012 |
| KR | 1020140037278 | 3/2014 |
| PL | 168049 B1 | 12/1995 |
| RU | 2235534 C1 | 9/2004 |
| WO | 9951114 A | 10/1999 |
| WO | 0025671 A | 5/2000 |
| WO | 0067750 A | 11/2000 |
| WO | 0122838 A | 4/2001 |
| WO | 0224957 A | 3/2002 |
| WO | 03006031 A | 1/2003 |
| WO | 03011309 A | 2/2003 |
| WO | 03047587 A | 6/2003 |
| WO | 03059361 A | 7/2003 |
| WO | 03063836 A | 8/2003 |
| WO | 2005000205 A2 | 1/2005 |
| WO | 2006072940 A2 | 7/2006 |
| WO | 2007065441 A | 6/2007 |
| WO | 2008005509 A2 | 1/2008 |
| WO | 2010111650 A2 | 9/2010 |
| WO | 2011152810 A | 12/2011 |
| WO | 2013184943 A | 12/2013 |
| WO | 2016081676 A1 | 5/2016 |
| WO | 2017085138 A | 5/2017 |
| WO | 2018100442 A | 6/2018 |

OTHER PUBLICATIONS

Choy, E.H. et al., "Cytokine Pathways and Joint Inflammation in Rheumatoid Arthritis," The New England Journal of Medicine 344:907-916 (2001 ), Massachusetts Medical Society.
Cooper, D.J. et al., "Plasma ionized calcium and blood lactate concentrations are inversely associated in human lactic acidosis*," Intensive Care Medicine 18:286-289 (1992), Springer-Verlag.
Davies, C.W., "The Extent of Dissociation of Salts in Water. Part VI. Some Calcium Salts of Organic Acids", pp. 277-281 (1938) (downloaded by Northeastern University on Oct. 27, 2014), Royal Society of Chemistry, London, UK. 2014.
Dillion, E. L. et al., "Lactate Inhibits Citrulline and Arginine Synthesis from Proline in Pig Enterocytes", pp. GI079-GI086 (1998) (downloaded from http://ajpgi.physiology.org on Feb. 1, 2017), American Physiological Society.
Eltzschig, H.K. et al., "Hypoxia and Inflammation," The New England Journal of Medicine 364:656-665(Feb. 2011), Massachusetts Medical Society.
Fomoni, A. et al, "Role of Inflammation in Diabetic Nephropathy," Current Diabetes Reviews 4: 10-17 (2008), Bentham Science Publishers Ltd.
Fujiwara, N. et al., "Macrophages in Inflammation," Current Drug Targets—Inflammation and Allergy 4:281-286 (2005), Bentham Science Publishers Ltd.
Genin, M. et al., "MI and M2 macrophages derived from THP-1 cells differentially modulate the esponse of cancer cells to etoposide," BMC Cancer 15:577 (2015), Bio Med Central.
Gilmore, T.D., "Introduction to NF-KB: players, pathways, perspectives," Oncogene 25:6680-6684 (2006), Springer Nature Publishing AG.
Gilroy, D. et al., "New insights into the resolution of inflammation," Seminars in Immunology 27:161-168 (2015), Elsevier Ltd, The Netherlands.

Hamid, Q. et al., "Differential in Situ Cytokine Gene Expression in Acute versus Chronic Atopic Dermatitis," The Journal of Clinical Investigation 94:870-876 (1994), The American Society of Clinical Investigation.
Hessen, M. et al., "Dry Eye: an Inflammatory Ocular Disease," Journal of Ophthalmic & Vision NPL17 Research, Ophthalmic Research Center 9:240-250 (2014), Wolters Kluwer—Medknow Publications, India.
Hotamisligil, G.S., "Inflammation and metabolic disorders," Nature 444:860-867 (2006), Springer Nature Publishing AG.
Jang J.H. et al., "BAI, a novel Cdk inhibitor, enhances famesyltransferase inhibitor LB42708-1mediated apoptosis in renal carcinoma cells through the downregulation of Bcl-2 and c-FLIP (L)," International Journal of Oncology 45:1680-1690 (2014).
Jiao, J. et al., "Comparative study of laser-induced choroidal neovascularization in rats by paraffin sections, frozen sections and high-resolution optical coherence tomography," Graefe's Archive for Clinical and Experimental Ophthalmology 251:301-307 (2013), Springer Nature Switzerland AG., Switzerland.
Kang, S. et al., "Effect of cediranib, an inhibitor of vascular endothelial growth factor receptor tyrosine kinase, in a mouse model of choroidal neovascularization," Clinical & Experimental Ophthalmology 41:63-72 (2013), The Authors.
Karin, M., "How NF-KB is activated: the role of the IKB kinase (IKK) complex," Oncogene 18:6867-6874 (1999), Springer Nature Publishing AG.
Kofler, S. et al., "Role of cytokines in cardiovascular diseases: a focus on endothelial responses to inflammation," Clinical Science 108:205-2 I 3 (2005), The Biochemical Society, Great Britain.
Kubantseva, N. et al., "Factors Affecting Solubility of Calcium Lactate in Aqueous Solutions," Journal of Dairy Science 87:863-867 (2004), Elsevier.
Lee, D.C. et al., "A Lactate-Induced Response to Hypoxia", Cel! 161:595-609 (2015), Cell Press, Cambridge, Massachusetts.
Manabe, I., "Chronic Inflammation Links Cardiovascular, Metabolic and Renal Diseases," Circulation Journal 75:2739-2748 (2011), The Japanese Circulation Society.
Medina, J. et al., "Angiogenesis in Chronic Inflammatory Liver Disease," Hepatology 39:1185-1 195(2004 ), American Association for the Study of Liver Diseases.
Minghetti, L., "Role of inflammation in neurodegenerative diseases," Current Opinion Neurology 18:315-321 (2005), Wolters Kluwer Health, Inc., Philadelphia, Pennsylvania.
Mojsilovic-Petrovic, J et al., "Hypoxia-inducible factor-I (HIF-1) is involved in the regulation of hypoxia-stimulated expression of monocyte chemoattractant protein-I (MCP-I/CCL2) and MCP-5 (Ccl 12) in astrocytes," Journal of Neuroinflammation 4: 1-15(2007), Bio Med Central Ltd.
Mundy, G.R., "Osteoporosis and Inflammation," Nutrition Reviews 65:SI47-SI51 (2007), Oxford Academic, Oxford, England.
Narrima, P. et al, "Persea Declinata (BI.) Kosterm Bark Crude Extract Induces Apoptosis in MCF-7 Cells via Go/G1 Cell Cycle Arrest, Bcl-2/Bax/Bcl-XI Signaling Pathways, and ROS Generation," Evidence-Based Complementary and Alternative Medicine 20 I 4: 1-14 (2014 ), Hindawi Publishing Corporation.
Page, R.C. et al., "Pathogenesis of inflammatory periodontal disease. A summary of current work," Laboratory Investigation 34:235-249 (1976), Williams & Wilkins.
Roh, Y.J. et al., "The Antiangiogenic Effects of Gold Nanoparticles on Experimental Choroidal Neovascularization in Mice," Investigative Ophthalmology & Vision Science 57:6561-6567 (2016), ARVO Journals.
Rui, L., "Energy Metabolism in the Liver," Comprehensive Physiology 4: 177-197 (2014), American Physiological Society.
Sevenoaks, M.J. et al., "Chronic Obstructive Pulmonary Disease, inflammation and co-morbidity—a common Inflammatory phenotype?" Respiratory Research 7: 1-9 (2006), Bio Med Central Ltd.
Shaw, A.C. et al., "Age-dependent dysregulation of innate immunity," Nature Reviews Immunology 13:1-27 (2013), Springer Nature Publishing AG.

(56) References Cited

OTHER PUBLICATIONS

Sheikh, M.D., M.S. et al., "Gastrointestinal Absorption of Calcium from Milk and Calcium Salts," The New English Journal of Medicine 317:532-536 ( 1987), Massachusetts Medical Society, Waltham, Massachusetts.

Stein, W.D. "Transport and Diffusion across Cell Membranes," Science 233:898 (1986), Academic Press.

Taylor, C.T. et al., "Ancient Atmospheres and the Evolution of Oxygen Sensing via the Hypoxia-Inducible Factor in Metazoans," Physiology 25:272-279 (2010), American Physiological Society.

Taylor, C.T., "Interdependent roles for hypoxia inducible factor and nuclear factor-KB in hypoxic inflammation," The Journal of Physiology 586:4055-4059 (2008), The Physiological Society.

Tilg, H. et al., "Insulin resistance, inflammation, and non-alcoholic fatty liver disease," Trends in Endocrinology and Metabolism: Trends in Endocrinology & Metabolism 19:371-379 (2008), Elsevier Inc., The Netherlands.

Vadlapatla, R.K. et al., "Hypoxia-Inducible Factor-I (HIF-1): A Potential Target for Intervention in OcularNeovascular Diseases," Current Drug Targets 14:1-33 (2013), Bentham Science Publishers.

Wang, G.L. et al., "Hypoxia-inducible factor I is a basic-helix-loop-helix-PAS heterodimer regulated by cellular 02 tension," Proceedings of the National Academy of Sciences of the United States of America 92:5510-5514 (1995).

Whyte, M.K. et al., "The Regulation of Pulmonary Inflammation by the Hypoxia-Inducible Factor-Hydroxylase Oxygen-Sensing Pathway," Annals of the American Thoracic Society 5:S271-S276 (2014), ATS Journals 11:Supp.

Kalman et al., "Lactate infusion fails to itnprove se1nantic categorization in 1\Izhei1ner's disease ", Brain Research Bulletin, 2005, pp. 533-539., 65(6).

\* cited by examiner

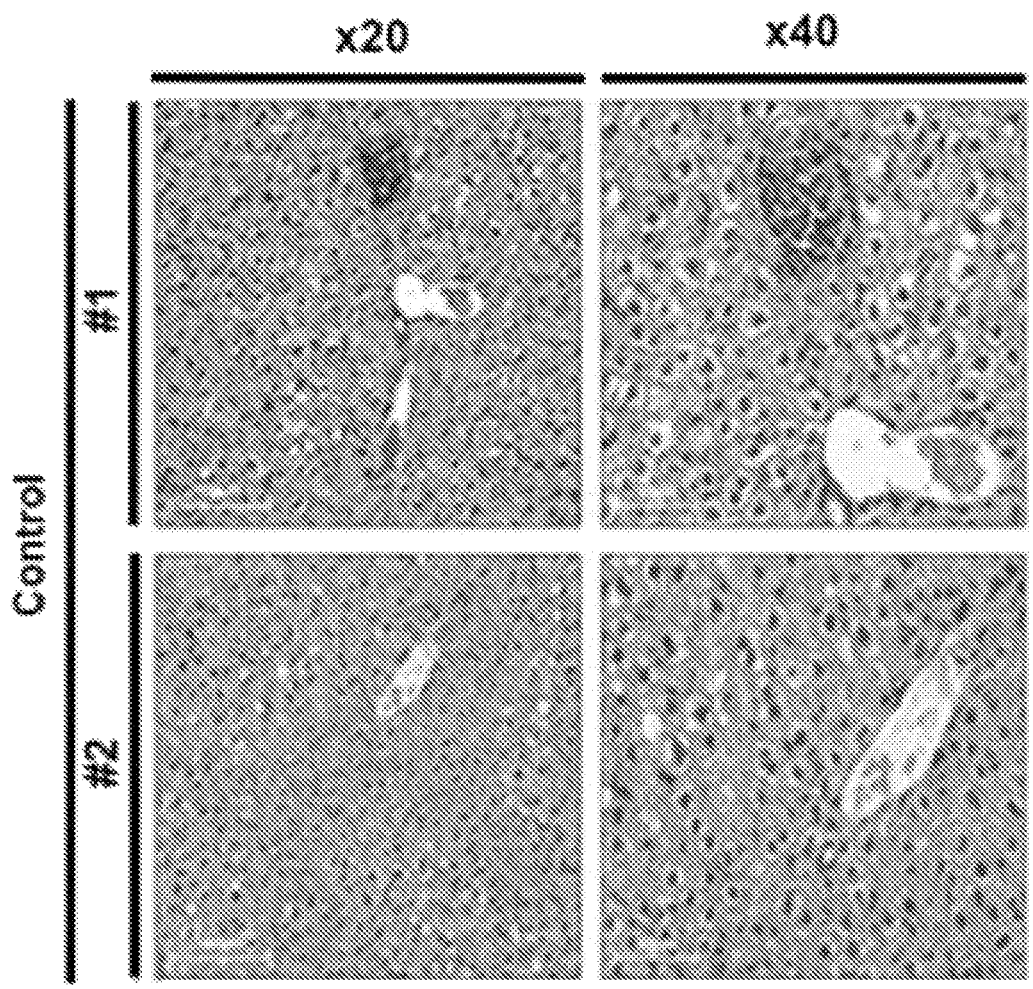

Comparison of collagen accumulation (Control vs. each group)

Control

Atherosclerosis

Atherosclerosis + CaLa

🟦 Loss of ligaments or gingiva
⬆ Aggressive periodontitis tissue

⬆ Aggressive periodontitis tissue

Control

Rheumatoid arthritis

⇧ Swollen by inflammation

Rheumatoid arthritis + CaLa

Normal

Crohn's

Crohn's + Cala

Normal

Colitis (ulcerative)

Colitis + CaLa

METHODS OF TREATING CHRONIC INFLAMMATORY DISEASES

CROSS-REFERENCE TO RELATED APPLICATIONS

This application is a continuation of U.S. patent application Ser. No. 17/131,820, filed Dec. 23, 2020, which is a continuation of U.S. patent application Ser. No. 16/942,757, filed Jul. 29, 2020 now U.S. Pat. No. 10,898,514 issued on Jan. 6, 2021, which is a continuation of U.S. patent application Ser. No. 16/246,252 filed Jan. 11, 2019 now U.S. Pat. No. 10,751,365 issued on Aug. 25, 2020, which claims benefit of the filing date of U.S. Provisional Application No. 62/616,923, filed Jan. 12, 2018, the contents of each of which are incorporated herein by reference in its entirety.

BACKGROUND OF THE INVENTION

Chronic inflammatory disease(s) (CID) underpins the pathological condition characterized by chronic inflammation, defined as a prolonged and persistent pro-inflammatory state (1). CID includes many common and uncommon CID such as respiratory diseases (e.g., asthma, chronic obstructive pulmonary disease, pneumonitis, and pulmonary fibrosis) (2), ocular diseases (e.g., keratitis and age-related macular degeneration) (3), autoimmune diseases (4), nephropathy (5), neurodegenerative diseases (e.g., Alzheimer's disease, stroke, Parkinson's disease, and multiple sclerosis) (6), cardiovascular diseases (e.g., atherosclerosis, arteriosclerosis, and myocarditis) (7), metabolic disorders (e.g., diabetes and obesity) (8), musculoskeletal diseases (e.g., rheumatoid arthritis and osteoporosis) (9, 10), periodontal diseases (e.g., pulpitis and periodontitis) (11), digestive diseases (e.g., non-alcoholic fatty liver disease, gastroenteritis, and chronic inflammatory bowel disease) (12), and skin disorders (e.g., psoriasis and atopic dermatitis) (13, 14).

An epidemiological study showed that CID is a leading cause of death throughout the world and has been increasing over the last three decades. It has been estimated that by 2030, 171 million people will be affected by CID in the United States (15). There are various types of anti-inflammatory drugs to treat inflammation, such as aspirin, antihistamines, COX-2 inhibitors, corticosteroid, and nonsteroidal anti-inflammatory drugs (NSAIDs). However, there are limitations for long term administration of such existing drugs due to side effects and temporal efficacy.

BRIEF SUMMARY OF THE INVENTION

Disclosed herein is a method of treating a chronic inflammatory disease, the method comprising administering to a subject in need thereof a therapeutically effective amount of calcium lactate.

Disclosed herein is a method of treating Alzheimer's disease, Parkinson's disease, atherosclerosis, and/or stroke, the method comprising administering to a subject in need thereof a therapeutically effective amount of calcium lactate.

Also disclosed is a method of treating multiple sclerosis, age-related macular degeneration, nonalcoholic fatty liver disease (NAFLD), and/or rheumatoid arthritis, the method comprising administering to a subject in need thereof a therapeutically effective amount of calcium lactate. In some embodiments, the method is for treating NAFLD and the NAFLD is nonalcoholic steatohepatitis (NASH).

Also disclosed is a method of treating pulpitis and/or periodontitis, the method comprising administering to a subject in need thereof a therapeutically effective amount of calcium lactate.

Further disclosed is a method of treating inflammatory bowel disease (IBD), the method comprising administering to a subject in need thereof a therapeutically effective amount of calcium lactate. In some embodiments, the IBD is Crohn's disease or ulcerative colitis.

Further disclosed is a method of treating spinal cord injury, cerebral hemorrhage, myocardial infarction, keratitis, and/or diabetic retinopathy, the method comprising administering to a subject in need thereof a therapeutically effective amount of calcium lactate.

Disclosed herein is a method of treating asthma, pulmonary fibrosis, obesity, gastroenteritis, chronic inflammatory bowel disease, and/or atopic dermatitis, the method comprising administering to a subject in need thereof a therapeutically effective amount of calcium lactate. Also disclosed herein is a method of treating chronic obstructive pulmonary disease, pneumonitis, keratitis, atherosclerosis, arteriosclerosis, myocarditis, diabetes, rheumatoid arthritis, pulpitis, periodontitis, and/or psoriasis, the method comprising administering to a subject in need thereof a therapeutically effective amount of calcium lactate. Also disclosed herein is a method of treating Alzheimer's disease, stroke, Parkinson's disease, multiple sclerosis, age-related macular degeneration, non-alcoholic fatty liver disease, sepsis, and/or osteoporosis, the method comprising administering to a subject in need thereof a therapeutically effective amount of calcium lactate.

In some embodiments, the calcium lactate is administered in a pharmaceutical composition comprising a pharmaceutically acceptable carrier, excipient, and/or diluent. In some embodiments, the pharmaceutical composition is formulated into liquid, powder, aerosol, injection, fluid transfusion, patch, capsule, pill, tablet, depot, or suppository.

In some embodiments, the pharmaceutical composition comprises a therapeutically effective amount of calcium lactate as an active agent and a pharmaceutically acceptable polysaccharide, polymer, lipid, or combinations thereof. In some embodiments, the pharmaceutical composition comprises the calcium lactate and the polysaccharide. In some embodiments, a weight ratio of the calcium lactate to the polysaccharide is 1:<0.2 to 1:5. In some embodiments, a weight ratio of the calcium lactate to the polysaccharide is 1:<0.2. In some embodiments, a weight ratio of the calcium lactate to the polysaccharide is 1:0.2 to 1:5.

In some embodiments, the pharmaceutical composition further comprises a polymer and/or lipid. In some embodiments, the pharmaceutical composition further comprises the polymer and lipid, wherein the weight ratio of the polymer to the lipid is 1:0.1 to 1:50. In some embodiments, the weight ratio of the calcium lactate to the polymer and/or lipid is at least 1:5. In some embodiments, a weight ratio of the calcium lactate to the polymer and/or lipid is 1:5 to 1:30.

In some embodiments, the pharmaceutical composition comprises the calcium lactate and the polymer and/or lipid. In some embodiments, the pharmaceutical composition comprises the polymer and lipid, wherein the weight ratio of the polymer to the lipid is 1:0.1 to 1:50. In some embodiments, a weight ratio of the calcium lactate to the polymer and/or lipid is at least 1:5. In some embodiments, the weight ratio of the calcium lactate to the polymer and/or lipid is 1:5 to 1:30.

In some embodiments, the composition is short-acting. In some embodiments, the composition is long-acting. In some embodiments, the composition is an injectable composition.

In some embodiments, the polysaccharide is a cellulose derivative, pectin, hyaluronic acid, starch, guar gum, chitosan, gelatin, collagen, alginate, alginic acid or combinations thereof.

In some embodiments, the polymer is a poloxamer, polyvinylpyrrolidone, polyethylene glycol (PEG), polyglycolic lactic acid (PLGA), or combinations thereof.

In some embodiments, the lipid is a mono- or tri-fatty acid glycerin ester or polyethylene glycol, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachidonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, at least about 40% of the active agent is released after 6 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, at least about 60% of the active agent is released after 12 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, at least about 80% of the active agent is released after 24 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, at least about 90% of the active agent is released after 48 hours.

In some embodiments, wherein upon placement of the pharmaceutical composition in an in vitro dissolution test comprising an elution test method at 300 rpm in 200 ml aqueous medium having a pH of 6.8 at 37° C. using a nylon filter having a pore size of 45 μm, less than about 40% of the active agent is released after 24 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, less than about 60% of the active agent is released after 48 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, less than about 80% of the active agent is released after 72 hours.

In some embodiments, upon placement of the pharmaceutical composition in an in vitro dissolution test comprising an elution test method at 300 rpm in 200 ml aqueous medium having a pH of 6.8 at 37° C. using a nylon filter having a pore size of 45 μm, less than about 90% of the active agent is released after 144 hours.

In some embodiments, the pharmaceutical composition is contained in a sterile glass or polyolefin container.

In some embodiments, the calcium lactate is coated with a pharmaceutically acceptable enteric coating. In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments, the weight ratio of the calcium lactate to the enteric coating is 10:0.5 to 1:1.5. In some embodiments, in an in vitro dissolution test comprising a USP Paddle method at a paddle speed of 50 rpm at 37° C., when the composition is placed in 0.1 HCl for 120 minutes followed by adjusting to pH 6.8 with phosphate buffer, less than about 20% of the active agent is released after 30 minutes. In some embodiments, in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 30% of the active agent is released after 60 minutes. In some embodiments, in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 50% of the active agent is released after 120 minutes. In some embodiments, in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 10% of the active agent is released after 120 minutes.

In some embodiments, the calcium lactate is provided in a food or nutrient composition comprising calcium lactate. In some embodiments, the food or nutrient composition is an injectable nutritional supplement.

BRIEF DESCRIPTION OF THE FIGURES

FIGS. 22A, 22B, and 22C Immunohistochemical results show that in the liver lipid droplets are not present in the 2 mg/kg calcium lactate-treated group, similar to the control group, while they are found in the methionine-choline deficient (MCD) group.

DETAILED DESCRIPTION OF THE INVENTION

Figure 1:
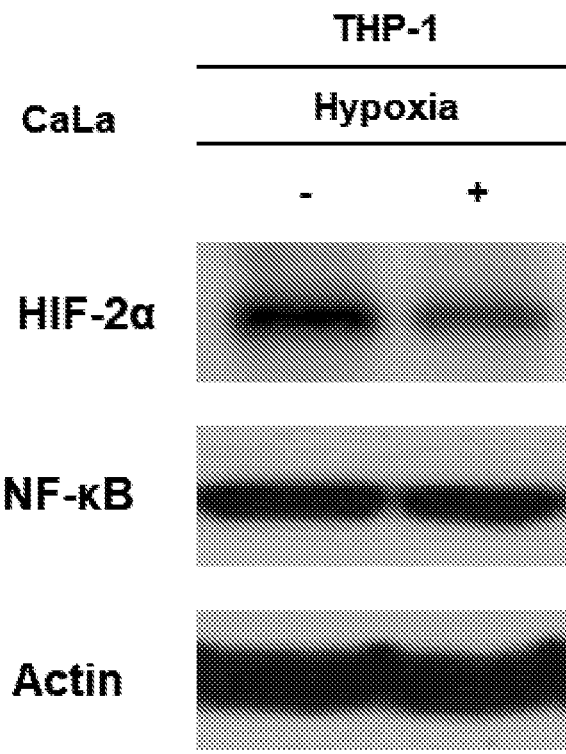
FIG. 1. Human leukemic monocyte in vitro experiment. Western blot results indicated that inflammatory factor (NF-Kb) was decreased by 2.5 mM calcium lactate treatment in THP-1 cells (human leukemic monocyte) under hypoxia condition.

Recently, many studies showed that CID is related to advancing age and suggested chronic inflammation as being associated with age-related immuno-senescence diseases (1-29). Chronic inflammation was elucidated to occur via complex interactions between parenchymal cells and stromal cells, such as immune cells, endothelial cells, and fibroblasts. Among others, myeloid-originated cells, such as monocytes and activated macrophages, were identified as major effector cells in CID. Upon activation with bacterial lipopolysaccharide, IFN-gamma, and damaged cells, macrophages produced many inflammatory cytokines and cleared endogenous and exogenous inflammatory agents through transcriptional control by nuclear factor-kappa B (NF-kB). Macrophages were also further polarized to more specialized macrophage subtypes. However, their finely controlled differentiation and activation of myeloid cells were dysregulated in chronic inflammation. Local tissue hypoxia caused the metabolic changes of cells, such as parenchymal and stromal cells, through induction of hypoxia inducible factors (HIFs). HIFs, especially HIF-1, contribute to the abnormal activation of macrophages and are a major contributor to chronic inflammatory response.

Most CID are characterized by inflammation. Injured tissue become resistant to blood flow and delivery of oxygen, thus becoming a hypoxic environment. Proinflammatory mediators and a hypoxic condition can elicit an angiogenic response through the induction of HIF-1. Additionally, a local inflammatory reaction exists in most CID, including as respiratory diseases (e.g., asthma, chronic obstructive pulmonary disease, pneumonitis, and pulmonary fibrosis), ocular diseases (e.g., keratitis and age-related macular degeneration), autoimmune diseases, nephropathy, neurodegenerative diseases (e.g., Alzheimer's disease, stroke, Parkinson's disease, and multiple sclerosis), cardiovascular diseases (e.g., atherosclerosis, arteriosclerosis, and myocarditis), metabolic disorders (e.g., diabetes and obesity), musculoskeletal diseases (e.g., rheumatoid arthritis and osteoporosis), periodontal diseases (e.g., pulpitis and periodontitis), digestive diseases (e.g., non-alcoholic fatty liver disease, gastroenteritis, and chronic inflammatory bowel disease), and skin disorders (e.g., psoriasis and atopic dermatitis). During inflammation, vascular permeability is increased and monocytes, macrophages, platelets, mast cells, and other leukocytes are recruited under the attraction of chemokines. Therefore, disclosed herein are therapeutic approaches targeting activation of macrophages and regulation of extracellular matrix degradation by targeting HIF-1, NF-kB, and lactate dehydrogenase (LAD) A and B.

Methods of Treatment

Disclosed herein is a method of treating a chronic inflammatory disease, the method comprising administering to a subject in need thereof a therapeutically effective amount of calcium lactate.

Disclosed herein is a method of treating Alzheimer's disease, Parkinson's disease, atherosclerosis, and/or stroke, the method comprising administering to a subject in need thereof a therapeutically effective amount of calcium lactate.

Also disclosed is a method of treating multiple sclerosis, age-related macular degeneration, nonalcoholic fatty liver disease (NAFLD), and/or rheumatoid arthritis, the method comprising administering to a subject in need thereof a therapeutically effective amount of calcium lactate. In some embodiments, the method is for treating NAFLD and the NAFLD is nonalcoholic steatohepatitis (NASH).

Also disclosed is a method of treating pulpitis and/or periodontitis, the method comprising administering to a subject in need thereof a therapeutically effective amount of calcium lactate.

Further disclosed is a method of treating inflammatory bowel disease (IBD), the method comprising administering to a subject in need thereof a therapeutically effective amount of calcium lactate. In some embodiments, the IBD is Crohn's disease or ulcerative colitis.

Further disclosed is a method of treating spinal cord injury, cerebral hemorrhage, myocardial infarction, keratitis, and/or diabetic retinopathy, the method comprising administering to a subject in need thereof a therapeutically effective amount of calcium lactate.

Disclosed herein are methods of treating asthma, pulmonary fibrosis, obesity, gastroenteritis, chronic inflammatory bowel disease, and/or atopic dermatitis, the method comprising administering to a subject in need thereof a therapeutically effective amount of calcium lactate. Also disclosed herein are methods of treating chronic obstructive pulmonary disease, pneumonitis, keratitis, atherosclerosis, arteriosclerosis, myocarditis, diabetes, rheumatoid arthritis, pulpitis, periodontitis, and/or psoriasis, the method comprising administering to a subject in need thereof a therapeutically effective amount of calcium lactate. Also disclosed herein are methods of treating Alzheimer's disease, stroke, Parkinson's disease, multiple sclerosis, age-related macular degeneration, non-alcoholic fatty liver disease, and/or sepsis, the method comprising administering to a subject in need thereof a therapeutically effective amount of calcium lactate.

Also disclosed herein are methods of treating osteoporosis, the method comprising administering to a subject in need thereof a therapeutically effective amount of calcium lactate.

The term "subject" or "patient" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the mammal is a human or a nonhuman.

As used herein, "treat", "treating", or "treatment" of one or more of the diseases disclosed herein by administration of the pharmaceutical composition refers to any lessening of severity, delay in onset, slowing of progression, or shortening of duration of one or more of the diseases disclosed herein, whether permanent or temporary, lasting or transient that can be attributed to or associated with administration of the composition.

The term "co-administration" or the like, as used herein, is meant to encompass administration of the selected two or more active agents to a single patient and is intended to include treatment regimens in which the agents are administered by the same or different route of administration or at the same or different time.

The pharmaceutical composition of the present disclosure can be administered in a therapeutically effective amount, and as used herein, the term "effective amount" or therapeutically effective amount" refers to an amount sufficient to treat or prevent diseases, at a reasonable benefit/risk ratio applicable to any medical treatment or prevention. The effective dosage level can be determined depending on severity of the disease, activity of the drug or active agent, a patient's age, body weight, health and sex, sensitivity to the drug, administration time, administration route, and excretion rate of the composition of the present disclosure, duration of treatment, drugs used simultaneously or in combination with the composition of the present disclosure, and other factors known in the medical field. The pharmaceutical composition of the present disclosure can be administered alone or in combination with other publicly-known drugs or components known as known for treating one or more of the diseases disclosed herein. It is important to administer the composition in the minimum amount that can exhibit the maximum effect without causing side effects, in consideration of all the above factors.

The pharmaceutical composition of the present disclosure can be administered such that the dosage per day of calcium lactate is, for example, about 10 mg/kg to about 1,000 mg/kg, about 10 mg/kg to about 500 mg/kg, about 10 mg/kg to about 250 mg/kg, about 10 mg/kg to about 200 mg/kg, about 10 mg/kg to about 100 mg/kg, about 1 mg/kg to about 100 mg/kg, about 1 mg/kg to about 75 mg/kg, about 1 mg/kg to about 50 mg/kg, about 1 mg/kg to about 25 mg/kg, or about 1 mg/kg to about 10 mg/kg. The administration frequency of the composition can be, but is not particularly limited to, once, twice, three times, four times, etc. divided doses a day.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the active agent described herein are administered to a patient susceptible to or otherwise at risk of one or more of the diseases disclosed herein. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the active agent described herein can be administered chronically, that is, for an extended period of time, including throughout the duration of the patient's life in order to ameliorate or otherwise control or limit the symptoms of the patient's disease or condition.

The amount of a given agent that will correspond to such an amount will vary depending upon factors such as the particular compound, disease condition and its severity, the identity (e.g., age, weight, gender, etc.) of the subject or host in need of treatment, but can nevertheless be routinely determined in a manner known in the art according to the particular circumstances surrounding the case, including, e.g., the specific agent being administered, the route of administration, the condition being treated, and the subject or host being treated.

Pharmaceutical Compositions

The term "calcium lactate" refers to a type of lactate metal salt that can, for example, exist as a hydrate, represented by $C_6H_{10}O_6Ca \cdot 5H_2O$ in which calcium ion is bonded to lactate. Calcium lactate can be in the form of white powder or granules at room temperature, or anhydrous at a 120° C. heating condition, and has a solubility of 5% (w/v).

Calcium lactate can be formulated into pharmaceutical compositions for treating one or more of the diseases disclosed herein.

In various embodiments, the invention provides a pharmaceutical composition comprising a therapeutically effective amount of calcium lactate as an active agent for treating one or more of the diseases disclosed herein and a pharmaceutically acceptable polysaccharide, polymer, lipid, or combinations thereof. In some embodiments, the pharmaceutical composition comprises the calcium lactate and the polysaccharide.

In some embodiments, the invention provides an enteric coating of the calcium lactate such that the active agent is protected from the acidic environment of the stomach and absorbed in the small intestine before it reaches the large intestine when the active agent is administered orally.

The present invention also provides short-acting and long-acting pharmaceutical compositions comprising calcium lactate. In some embodiments, the long-acting compositions comprise calcium lactated coated with at least one enteric-coating material such as hydroxypropyl methyl cellulose phthalate (HPMCP), cellulose acetate phthalate (CAP), polyvinyl acetate phthalate (PVAP), shellac and a polymer of methacrylic acid, and an ester thereof.

The pharmaceutical composition of the invention can be formulated into pharmaceutical preparations for oral administration. Examples of the preparation include powders, tablets, capsules, granules or syrups, tablets and capsules, but not limited thereto.

Also provided herein are formulations of hydrogels particularly methylcellulose, poloxamer, pectin, and alginate hydrogel which can remain in a solution or nanoparticle form in vitro, and the gel can form when injected into the body and allow sustained release of calcium lactate. The relatively short drug release time which is the weakness of the hydrogel has been improved by increasing the interaction between the drug and hydrogel or by delaying the diffusion of the drug in the hydrogel.

The weight ratio of the calcium lactate to the polysaccharide can be, e.g., 1:<0.2 to 1:5, 1:0.01 to 1:5, 1:0.05 to 1:5, or 1:0.1 to 1:5. The weight ratio of the calcium lactate to the polysaccharide can be 1:<0.2. The weight ratio of the calcium lactate to the polysaccharide can be 1:0.2 to 1:5.

In some embodiments, the pharmaceutical composition further comprises a polymer or lipid. The weight ratio of the calcium lactate to the polymer or lipid can be at least 1:5. The weight ratio of the calcium lactate to the polymer or lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition further comprises a polymer and lipid. The weight ratio of the calcium lactate to the polymer and lipid can be at least 1:5. The weight ratio of the calcium lactate to the polymer and lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition comprises the calcium lactate and the polymer or lipid. The weight ratio of the calcium lactate to the polymer or lipid can be at least 1:5. The weight ratio of the calcium lactate to the polymer or lipid can be 1:5 to 1:30. The weight ratio of the calcium lactate to the polymer or lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the pharmaceutical composition comprises the calcium lactate and the polymer and lipid. The weight ratio of the calcium lactate to the polymer and lipid can be at least 1:5. The weight ratio of the calcium lactate to the polymer and lipid can be 1:5 to 1:30. The weight ratio of the calcium lactate to the polymer and lipid can be 1:5 to 1:30, e.g., 1:5 to 1:30, 1:5 to 1:20, 1:5 to 1:10, 1:10 to 1:30, 1:10 to 1:20, or 1:20 to 1:30.

In some embodiments, the weight ratio of the polymer to the lipid can be 1:0.1 to 1:50, 1:0.1 to 1:20, 1:0.1 to 1:10, 1:0.1 to 1:5, 1:0.1 to 1:2, 1:0.1 to 1:1, 1:0.1 to 0.5, or 1:0.1 to 1:0.2.

Polysaccharides suitable for use in the composition can be a cellulose derivative (e.g., carboxymethyl cellulose (CMC), ethyl cellulose (EC), hydroxypropyl methyl cellulose (HPMC), methyl cellulose (MC)), pectin, hyaluronic acid, starch, guar gum, chitosan, gelatin, collagen, alginate, alginic acid, or combinations thereof.

Polymers suitable for use in the composition can be a poloxamer, polyvinylpyrrolidone, polyethylene glycol (PEG), polyglycolic lactic acid (PLGA), or combinations thereof.

Lipids suitable for use in the composition can be a mono- or tri-fatty acid glycerin ester or polyethylene glycol, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, acetyl palmitate, lauryl alcohol, oleyl alcohol, acetyl alcohol, stearyl alcohol, or combinations thereof.

The invention is further directed to a pharmaceutical composition comprising a therapeutically effective amount of calcium lactate as an active agent for treating one or more of the diseases disclosed herein, wherein the calcium lactate is coated with a pharmaceutically acceptable enteric coating. In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments, the weight ratio of the calcium lactate to the enteric coating is 10:0.5 to 10:15, 10:0.5 to 1:1, 10:0.5 to 10:5, 10:0.5 to 10:3, 10:0.5 to 10:2, 10:0.5 to 10:1, 10:0.5 to 1:0.8.

By "pharmaceutically acceptable," as used herein, refers a material, such as a carrier or diluent, which does not abrogate the biological activity or properties of the compound, and is relatively nontoxic, i.e., the material can be administered to an individual without causing undesirable biological effects or interacting in a deleterious manner with any of the components of the composition in which it is contained.

A pharmaceutical composition, as used herein, refers to a mixture of calcium lactate with other chemical components that are pharmaceutically acceptable, such as but not limited to carriers, stabilizers, diluents, disintegrants, suspending agents, thickening agents, binders, antimicrobial agents, antimicrobial preservatives, antioxidants, and/or buffering agents. The pharmaceutical composition facilitates administration of the calcium lactate to a subject.

The term "carrier," as used herein, refers to relatively nontoxic chemical compounds or agents that facilitate the incorporation of a compound into cells or tissues. The term "diluent" refers to chemical compounds that are used to dilute the compound of interest prior to delivery. Diluents can also be used to stabilize compounds because they can provide a more stable environment. Pharmaceutically acceptable additives include diluents, binders, solubilizers, solubility enhancers, pore formers, osmotic agents, gas formers, lubricants and fluidizers well known in the art, but not limited thereto.

Diluents can include lactose, fructose, dextrose, sucrose, maltose, microcrystalline cellulose, starch, calcium hydrogen phosphate, mannitol or a mixture thereof, but not limited thereto. Other diluents include microcrystalline cellulose, lactose, mannitol, calcium phosphate and the like.

Examples of binders can include povidone, hydroxypropylcellulose, polyvinylalcohol, hydroxypropylmethylcellulose, carboxymethyl-cellulose sodium and thereof.

Solubilizing agents include surfactants, cyclodextrins and derivatives thereof, lipophilic substances or mixtures thereof, but are not limited thereto.

Surfactants include water soluble or water dispersible nonionic, nonpolar nonionic, anionic, cationic, amphoteric or ionic surface activators or mixtures thereof, but are not limited thereto.

Examples of disintegrants include crospovidone, croscarmellose sodium, glycolic acid starch sodium, and examples of the lubricant include magnesium stearate, calcium stearate, sodium stearyl fumarate and thereof.

The pharmaceutical compositions of the invention can further include antimicrobial agents, such as benzyl alcohol, chlorobutanol, phenylethyl alcohol, phenyl-mercuric acetate, potassium sorbate, and sorbic acid. Antifungal agents include such compounds as benzoic acid, butylparaben, ethylparaben, methylparaben, propylparaben, and sodium benzoate.

Antimicrobial preservatives can be added to the pharmaceutical compositions of the present invention in order to protect them against the growth of potentially harmful microorganisms, which usually invade the aqueous phase, but in some cases can also grow in the oil phase of a composition. Thus, preservatives with both aqueous and lipid solubility are desirable. Suitable antimicrobial preservatives include, e.g., alkyl esters of p-hydroxybenzoic acid, propionate salts, phenoxyethanol, methylparaben sodium, propylparaben sodium, sodium dehydroacetate, benzalkonium chloride, benzethonium chloride, benzyl alcohol, hydantoin derivatives, quaternary ammonium compounds and cationic polymers, imidazolidinyl urea, diazolidinyl urea, and trisodium ethylenediamine tetracetate (EDTA).

Antioxidants can be added to protect all of the ingredients of the pharmaceutical compositions from damage or degradation by oxidizing agents present in the composition itself or the use environment, e.g., anoxomer, ascorbyl palmitate, butylated hydroxyanisole, butylated hydroxytoluene, hypophosphorous acid, potassium metabisulfite, propyloctyl and dodecyl gallate, sodium metabisulfite, sulfur dioxide, and tocopherols.

Buffering agents can be used to maintain a desired pH of the pharmaceutical compositions once established, from the effects of outside agents and shifting equilibria of components of the composition.

The pharmaceutical compositions described herein can be prepared following techniques known in the art, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

In some embodiments, the pharmaceutical compositions of the invention are short-acting. The term "short-acting" refers to a composition that releases substantially all of the active agent within 48 hours when tested in an in vitro dissolution test described herein, for example, from time of delivery, time 0, until about 1 hour to about 48 hours, until about 3 hours to about 24 hours, until about 6 hours to about 24 hours, or until about 12 hours to about 24 hours.

For example, upon placement of the composition in an in vitro dissolution test comprising an elution test method (e.g., from Labfine Co., Mumbai, India) at 300 rpm in 200 ml aqueous medium having a pH of 6.8 at 37° C. using a nylon filter having a pore size of 45 inn, at least about 40% of the active agent is released after 6 hours, at least about 60% of the active agent is released after 12 hours, at least about 80% of the active agent is released after 24 hours, and/or at least about 90% of the active agent is released after 48 hours. In some embodiments, upon placement of the composition in an in vitro dissolution test comprising an elution test method (e.g., from Labfine Co., Mumbai, India) at 300 rpm in 200 ml aqueous medium having a pH of 6.8 at 37° C. using a nylon filter having a pore size of 45 inn, at least about 40% to about 60% of the active agent is released after 6 hours, at least about 60% to about 80% of the active agent is released after 12 hours, at least about 80% to about 90% of the active agent is released after 24 hours, and/or at least about 90% to about 100% of the active agent is released after 48 hours.

In some embodiments, the pharmaceutical compositions of the invention are long-acting. The term "long-acting" is intended to mean composition that releases the active agent slowly after the initial dosage, for example, from time of delivery, time 0, until about 48 hours to about 192 hours, until about 72 hours to about 192 hours, until about 96 hours to about 192 hours, until about 120 hours to about 192 hours, or until about 144 hours to about 192 hours.

In some embodiments, upon placement of the composition in an in vitro dissolution test comprising an elution test method (e.g., from Labfine Co., Mumbai, India) at 300 rpm in 200 ml aqueous medium having a pH of 6.8 at 37° C. using a nylon filter having a pore size of 45 µm, less than about 40% of the active agent is released after 24 hours, less than about 60% of the active agent is released after 48 hours, less than about 80% of the active agent is released after 72 hours, less than about 90% of the active agent is released after 144 hours. In some embodiments, upon placement of the composition in an in vitro dissolution test comprising an elution test method (e.g., from Labfine Co., Mumbai, India) at 300 rpm in 200 ml medium having a pH of 6.8 at 37° C. using a nylon filter having a pore size of 45 µm, about 20% to about 50% of the active agent is released after 24 hours, about 20% to about 40% of the active agent is released after 24 hours, about 40% to about 70% of the active agent is released after 48 hours, about 40% to about 60% of the active agent is released after 48 hours, about 40% to about 80% of the active agent is released after 72 hours, about 50% to about 80% of the active agent is released after 72 hours, about 60% to about 90% of the active agent is released after 144 hours, or about 70% to about 90% of the active agent is released after 144 hours.

In some embodiments, upon placement of the composition in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than about 20% of the active agent is released after 30 minutes, less than 30% of the active agent is released after 60 minutes, less than 50% of the active agent is released after 120 minutes, and/or less than 10% of the active agent is released after 120 minutes.

In some embodiments, the pharmaceutical compositions of the invention are injectable dosage forms. For parenteral injections, appropriate formulations can include aqueous or nonaqueous solutions, preferably with physiologically compatible carriers.

Pharmaceutical formulations for parenteral administration include aqueous solutions of the active compound(s) in water-soluble form. Additionally, suspensions of the active agent can be prepared as appropriate oily injection suspensions. Suitable lipids or lipophilic carriers include fatty oils such as sesame oil, or synthetic fatty acid esters, such as ethyl oleate or triglycerides, or liposomes. The lipid can be a mono- or tri-fatty acid glycerin ester or polyethylene glycol, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

Since the medical application of hydrogels, numerous hydrogels have been developed and studied in many fields, including the medical, pharmaceutical, and cosmetic industries. Although hydrogels are generally biocompatible, they have various problems that are limiting the delivery of a drug, and various efforts are made to solve the problems. A hydrogel is a three-dimensional structure composed of a network of hydrophilic polymers. More than 90% of the components are composed of water. Hydrogels have been actively studied in the biomedical field due to their similarity to bio-tissue such as high moisture content, porous structure, relatively soft properties, and biocompatibility. Hydrogels can exhibit various properties depending on the kind of polymer used as the main chain or the crosslinking method adopted. When a polymer of polyacrylic acid series polymer or a synthetic compound such as polyvinyl alcohol is used, the biocompatibility is low, but the chemical modification is easy, so that the engineering application is very easy. On the other hand, when natural compounds, especially pectin, alginate, collagen, fibrin and hyaluronic are used as the main chain, the chemical modification is difficult. Nevertheless, there are advantages of using these materials that are biologically derived components, as it is suitable for clinical application and there are few side effects such as immune inflammation reaction at the time of transplantation.

It is the cross-linking method that affects the properties of the hydrogel as well as the type of polymer used. Even if the same polymer is used as the main chain, the hydrogel having completely different characteristics can be obtained if the crosslinking method is different. The method of crosslinking hydrogels can be broadly divided into physical and chemical methods. Physical crosslinking methods include ionic interaction, hydrophobic interaction, hydrogen bond, and reversible crosslinking by structural entanglement. These crosslinking methods can easily induce the formation of a three-dimensional network structure without the need for a separate chemical additive or complicated process. On the other hand, the chemical crosslinking method typically forms covalent bond that result an irreversible and stable network as compared with the physical crosslinking method. Hydrogels with excellent biocompatibility and various physicochemical properties have been extensively studied in biomedical fields such as drug delivery and tissue engineering. Most hydrogels exhibit shorter drug release time than other drug delivery systems due to their high water content, and there is a need to develop a system with a longer drug release time.

In some embodiments, the pharmaceutical compositions of the invention are oral dosage forms. For oral administration, the compound described herein can be formulated readily by combining the active agent with pharmaceutically acceptable carriers or excipients well known in the art. Such carriers enable the active agent described herein to be formulated as tablets, powders, pills, dragees, capsules, liquids, gels, syrups, elixirs, slurries, suspensions and the like, for oral ingestion by a patient to be treated.

Pharmaceutical preparations for oral use can be obtained by mixing one or more solid carriers with the compound described herein, optionally grinding the resulting mixture, and processing the mixture of granules, after adding suitable auxiliaries, if desired, to obtain tablets or dragee cores. Suitable excipients include, but are not limited to, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents can be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical compositions can be formulated in conventional manner using one or more pharmaceutically acceptable carriers comprising excipients and auxiliaries which facilitate processing of the active agent into preparations which can be used pharmaceutically. Proper formulation is dependent upon the route of administration chosen. Any of the well-known techniques can be used as suitable and as understood in the art. Pharmaceutical compositions described herein can be manufactured in a conventional manner, such as, by way of example only, by means of conventional mixing, dissolving, granulating, dragee-making, levigating, emulsifying, encapsulating, entrapping or compression processes.

Aqueous suspensions can also contain one or more polymers as suspending agents. The polymer can be a poloxamer, polyvinylpyrrolidone, polyethylene glycol (PEG), polyglycolic lactic acid (PLGA), or combinations thereof. Other useful polymers include water-soluble polymers such as cellulosic polymers, e.g., hydroxypropyl methylcellulose, and water-insoluble polymers such as cross-linked carboxyl-containing polymers. Useful compositions can also include a mucoadhesive polymer, selected from, for example, carboxymethylcellulose, carbomer (acrylic acid polymer), poly (methylmethacrylate), polyacrylamide, polycarbophil, acrylic acid/butyl acrylate copolymer, sodium alginate, and dextran.

In some embodiments, provided are pharmaceutical dosage forms comprising calcium lactate and a pharmaceutically acceptable enteric coating in order to control the release of the active agent. In some embodiments, the coating is a film and, in another embodiment, it is a membrane. The enteric coating, e.g., film or membrane, can serve to delay release until after the stomach and to protect the active agent from gastric fluid. The enteric coating can comprise one or more substances preferably of a polymeric nature (e.g., methacrylates etc.; polysaccharides etc. as described in more detail below) or combination of more than one such substance, optionally including other excipients, such as, for example, plasticizers. In some embodiments, the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof. In some embodiments of the invention the composition comprises a hydrogel-forming polymer and further polymers able to achieve a desired delay (or other change) in the release of the active agent.

In the case of tablets for oral use, carriers which are commonly used include lactose and corn starch. Lubricating agents, such as magnesium stearate, are also typically added. For oral administration in a capsule form, useful diluents include lactose and dried corn starch.

The sterile injectable preparation can also be a sterile injectable suspension in a non-toxic parenterally acceptable carrier such as lipids.

The amount of calcium lactate included in the pharmaceutical compositions can be, but is not limited to, from 1 wt % to 50 wt %, from 1 wt % to 40 wt %, from 1 wt % to 35 wt %, from 1 wt % to 30 wt %, from 1 wt % to 20 wt %, from 1 wt % to 15 wt %, or from 1 wt % to 10 wt % based on the total weight of the final composition. The concentration of the calcium lactate included in a single dose of the pharmaceutical composition can be, but is not limited to, 2.5 mM to 100 mM, 2.5 mM to 50 mM, 2.5 mM to 25 mM, 5 mM to 100 mM, 5 mM to 50 mM, 5 mM to 25 mM, 10 mM to 100 mM, 10 mM to 50 mM, or 10 mM to 25 mM.

Solid oral pharmaceutical compositions can be prepared by conventional techniques such as dry granulation, direct compression, wet granulation, extrusion spheronization, melt granulation or compression coating, but not limited thereto. The coating can be applied as described below and can vary as to thickness and density. The amount of coating is defined by the additional weight added to (gained by) the dry composition (e.g., bead or core containing the calcium lactate) of the invention. Weight gain can be in the range of 0.1% to 50%, 1% to 20%, 1% to 15%, 3% to 10%, 5% to 12%, or 8% to 12%.

The coating process can be carried out by any suitable means such as, for example, by use of a coating machine which applies a solution of a polymer coat (as described above in particular) to the composition. Polymers for coating are either provided by the manufacturer in ready-made solutions for direct use or can be made up before use following manufacturers' instructions.

Unit Dosages and Kits

The term "unit dosage form" refers to a physically discrete unit suitable as a single dosage, each unit containing a predetermined quantity of active ingredient, in association with a suitable pharmaceutical excipient, by which one or more is used throughout the dosing regimen to produce a desired therapeutic effect, e.g., treating one or more of the diseases disclosed herein.

The pharmaceutical compositions described herein can be in unit dosage forms suitable for single administration of precise dosages. In unit dosage form, the formulation is divided into unit doses containing appropriate quantities of one or more active agents. The unit dosage can be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection can be presented in unit dosage form, which include, but are not limited to ampoules, or in multi-dose containers.

The daily dosages appropriate for calcium lactate can be from about 1 mg/kg to about 1000 mg/kg, about 10 mg/kg to about 750 mg/kg, about 10 mg/kg to about 500 mg/kg, or about 100 mg/kg to 500 mg/kg per body weight. An indicated daily dosage in the larger mammal, including, but not limited to, humans, is in the range from about 5 mg to about 100,000 mg, conveniently administered in divided doses, including, but not limited to, up to four times a day or in long-acting form. Suitable unit dosage forms for administration include from about 10 mg to about 1000 mg, about 100 mg to about 1000 mg, about 500 mg to about 750 mg, about 25 mg to about 250 mg, about 50 mg to about 100 mg, about 10 mg to about 200 mg, or about 10 mg to about 250 mg of the active agent. The administration frequency of the composition of the present disclosure can be, but is not particularly limited to, once, twice, three times, four times, etc. divided doses a day. An appropriate "effective" amount in any individual case can be determined using techniques, such as a dose escalation study.

The foregoing ranges are merely suggestive, as the number of variables in regard to an individual treatment regime is large, and considerable excursions from these recommended values are not uncommon. Such dosages can be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of the active agent lies preferably within a range of circulating concentrations that include the $ED_{50}$ with minimal toxicity. The dosage can vary within this range depending upon the dosage form employed and the route of administration utilized.

According to the present invention, the pharmaceutical compositions can be in the form of a sterile injectable preparation, for example a sterile injectable aqueous or oleaginous suspension. The pharmaceutical compositions of the present invention can be orally administered in any orally acceptable dosage form including, but not limited to, capsules, tablets, aqueous suspensions or solutions.

The invention is also directed to a sterile glass or polyolefin container comprising a pharmaceutical composition disclosed herein. In some embodiments, the container is non-DEHP (Bis(2-ethylhexyl) phthalate (di-2-ethylhexyl phthalate, diethylhexyl phthalate, DEHP; dioctyl phthalate, DOP) or non-PVP (Polyvinylpyrrolidone).

A kit comprises suitable containers, such as boxes, individual bottles, bags or ampoules. Suspension compositions can be packaged in single-dose non-reclosable containers or multiple-dose reclosable containers.

Incorporated herein by reference in their entirety are US2017/0360727A1, published Dec. 21, 2017, and PCT/IB2017/054091, Int'l Filing Date: Jul. 7, 2017. Also incorporated herein by reference in their entirety are U.S. Appl. No. 62/616,923 filed Jan. 12, 2018.

EXAMPLES

Example 1. Cell Culture for Age-Related Macular Disease

Human retinal pigment epithelium cell line, ARPE-19, was purchased from American Type Culture Collection (Manassas, VA, USA). The ARPE-19 cells were maintained in RPMI1640 containing 10% fetal bovine serum (Life Technologies, Gaithersburg, MD, USA), 100 IU/ml penicillin, and 100 µg/ml streptomycin (Welgene, Daegu, South Korea).

Example 2. Cell Culture for Alzheimer's Disease

Human Brain cell line, SK-N-SH, was purchased from American Type Culture Collection (Manassas, VA, USA). The SK-N-SH cells were maintained in RPMI1640 containing 10% fetal bovine serum (Life Technologies, Gaithersburg, MD, USA), 100 IU/ml penicillin, and 100 µg/ml streptomycin (Welgene, Daegu, South Korea).

Example 3. Cell Culture for Fibroblast

Human Colon Fibroblast cell line, CCD-18-Co, was purchased from American Type Culture Collection (Manassas, VA, USA). The CCD-18Co cells were maintained in DMEM containing 10% fetal bovine serum (Life Technologies, Gaithersburg, MD, USA), 100 IU/ml penicillin, and 100 µg/ml streptomycin (Welgene, Daegu, South Korea).

Example 4. Cell Culture for Non-Alcoholic Steatohepatitis (NASH)

Human Hepatocellular carcinoma cell line, HepG2, was purchased from American Type Culture Collection (Manassas, VA, USA). The HepG2 cells were maintained in RPMI 1640 containing 10% fetal bovine serum (Life Technologies, Gaithersburg, MD, USA), 100 IU/ml penicillin, and 100 µg/ml streptomycin (Welgene, Daegu, South Korea).

Example 5. Cell Culture for Vascular Disease

Human Umbilical Vein Endothelial cell line, HUVEC, was purchased from American Type Culture Collection (Manassas, VA, USA). The HUVEC cells were Endothelial Cell Growth Medium 2 maintained in Endothelial Cell Growth Medium 2 Supplement MIX (PromoCell, Heidelberg, Germany)

Example 6. Macrophage Culture

Human Hepatic Stellate cell line, LX-2, was purchased from Sigma-Aldrich (St Louis, MO, USA). The LX-2 cells were maintained in DMEM containing 2% fetal bovine serum (Life Technologies, Gaithersburg, MD, USA), 100 IU/ml penicillin, and 100 µg/ml streptomycin (Welgene, Daegu, South Korea).

Human Monocyte cell line, THP-1, was purchased from American Type Culture Collection (Manassas, VA, USA). The THP-1 cells were maintained in RPMI1640 containing 10% fetal bovine serum (Life Technologies, Gaithersburg, MD, USA), 100 IU/ml penicillin, 100 µg/ml streptomycin (Welgene, Daegu, South Korea), and 0.55 uM 2-Mecaptpethanol. Cell were cultured in both conditions, one condition is a humidified atmosphere at 37° C. containing 5% $CO_2$, and another is hypoxia culture condition was maintained at 1% oxygen, 5% and 94%.

Example 7. Regents

Calcium lactate (CaLa) and lipopolysaccharide (LPS) were purchased from Sigma-Aldrich (St Louis, MO, USA). 2-mercaptoethanol was purchased from Gibco (Grand Island, NY, USA). Phorbol 12-myristate 13-acetate (PMA) was purchased from Enzo Lifesciences (Enzo Diagnostic, NY, USA). Human Interferon-gamma, Human Interleukin-4 (IL-4) and Human Interleukin-10 (IL-10) were purchased from BPS Bioscience (San Diego, CA, USA). Paraformaldehyde (PFA) solution (4%) was purchased from Biosesang (Biosesang Inc., Gyeonggi, Korea).

Example 8. Cell Viability Assay

The live cell movie analyzer, JuLI™ Br (NanoEnTek Inc., Seoul, Korea) in ARPE-19 cells, was used to confirm the toxicity of CaLa. Cells were seeded into 6-well culture plates at a density of $2.5 \times 10^5$ cells/well in medium. After 24 h incubation, the cells treated with 2.5 mM CaLa for 12 hr and 24 hr. The cells were continuously monitored for 24 h during CaLa treatment time. (30, 31)

Example 9. Macrophage Differentiation

The human monocytic cell line, THP-1, was purchased from American Type Culture Collection (Manassas, VA, USA). THP-1 cells were maintained in RPMI 1640 media (Hyclone Laboratories, Inc., Logan, UT, USA) supplemented with 10% fetal bovine serum (Hyclone Laboratories, Inc., Logan, UT, USA), 100 IU/ml penicillin (Welgene, Daegu, South Korea), 100 µg/ml streptomycin (Welgene, Daegu, South Korea), and 0.55 µM 2-mercaptoethanol (Gibco, Grand Island, NY, USA). THP-1 cell was maintained in a humidified atmosphere of 5% CO2, at 37° C. THP-1 monocytes are differentiated into macrophages by 12 h incubation with Phorbol 12-myristate 13-acetate (PMA) and 100 µg/ml (Enzo Diagnostic, NY, USA) in RPMI 1640 medium. Macrophages were polarized in M1 macrophages by 24 h incubation with 20 ng/ml of IFN-γ (BPS Bioscience, San Diego, CA, USA) and 100 µg/ml of LPS (Sigma-Aldrich, St Louis, MO, USA) in RPMI 1640 medium. Macrophage M2 polarization was obtained by 24 h incubation with 20 ng/ml of IL-4 (BPS Bioscience, San Diego, CA, USA) and 20 ng/ml of IL-10 (BPS Bioscience, San Diego, CA, USA) in RPMI 1640 medium. (32)

Example 10. Optical Observation for Cell Viability

The live cell movie analyzer, JuLI™ Br (NanoEnTek Inc., Seoul, Korea) in ARPE-19 cells, was used to confirm the toxicity of CaLa. Cells were seeded into 6-well culture plates at a density of $2.5 \times 10^5$ cells/well in medium. After a 24 h incubation, the cells treated with 2.5 mM CaLa for 12 h and 24 hr. The cells were continuously monitored for 24 h during CaLa treatment time.

Example 11. Western Blot Analysis

To prepare whole cell lysate, cells were lysed with lysis buffer (1% NP-40, 0.25% sodium deoxycholate, 150 mM NaCl, 1 mM EDTA, 1% Triton X-100, 50 mM Tris-HCl (pH 7.4), 10% Glycerol) with protease inhibitor cocktail (Roche, Basel, Switzerland) and phosphatase inhibitors ($NA_3VO_4$ 1 mM, NaF 100 mM). Then, protein concentration was measured using the Bicinchoninic acid (BCA) assay kit (Thermo Scientific, Waltham, MA). Whole cell or nuclear lysates were transferred onto polyvinylidene fluoride membranes (Merck Millipore, Billerica, MA, USA). After blocking in 5% non-fat milk (Bio-Rad, Hercules, CA, USA) for 1 h, the membranes were incubated overnight at 4° C. with primary antibody diluted in TBST containing 100 mM Tris-HCl (pH 7.5), 1.5 M NaCl, and 0.5% Tween-20 obtained from Sigma-Aldrich, to which 5% BSA and 0.1% sodium azide (Sigma-Aldrich) had been added. Specific primary antibodies to HIF-1α (1:1000), HIF-2a (1:1000), LDH-A (1:1000), LDH-B (1:1000), TLR-4 (1:1000), NF-κB (1:1000), VEGF (1:1000), α-tubulin (1:1000), Actin (1:1000), and GAPDH (1:5000). The next day, the membranes were washed with TBST and incubated for 2 h with anti-rabbit secondary antibody (1:10000). Immunoblots were developed using a western blot detection reagent (Abclone, Seoul, Korea) and exposed to x-ray film (Agfa, Leverkusen, Germany) according to the manufacturer's protocol.

Example 12. Immunocytochemistry

ARPE-19 and SK-N-SH cells were fixed on bio-coated coverslips (BD bioscience, San Jose, CA, USA) by 4% PFA for 20 min and then incubated with the primary antibodies for 15 h. The primary antibodies were as follows: HIF-1α (1:300, BD Biosciences, San Jose, CA, USA); LDH-A (1:300, Santa Cruz Biotechnology, Santa Cruz, CA, USA); LDH-B (1:300, Santa Cruz Biotechnology, Santa Cruz, CA, USA); NF-κB (1:300, Santa Cruz Biotechnology, Santa Cruz, CA, USA); TLR-4 (1:300, Santa Cruz Biotechnology, Santa Cruz, CA, USA); apoE (1:200, Santa Cruz Biotechnology, Santa Cruz, CA, USA). After PBS wash, the cells were incubated with anti-mouse secondary biotinylated antibody (1:2000, Vector Laboratorie, Burlingame, CA, USA) and visualized with streptavidin conjugated to Fluorescein (Vector Laboratorie, Burlingame, CA, USA). Coverslips were mounted on microscope slides with VECTASHIELD® Hard Set™ Mounting Medium with DAPI (Vector Laboratories, Burlingame, CA, USA). Confocal fluorescence images were obtained with confocal laser scanning microscopy (LSCM, Nikon A1+, Tokyo, Japan) under a 60× oil immersion lens.

Example 13. Animal Model for NASH

All experiments were performed under the institutional guidelines established by the Institutional Animal Care and Use Committee at Gachon University (IACUC-2017-0008). Female 5-week-old C57BL/6 mice were purchased form KOATEC (Pyeongtaek, South Korea) and were fed Methionine-Choline diet (MCD) for 4 weeks. When the mice weighed 15 g each, the mice were autopsied randomly to identify nonalcoholic steatohepatitis (NASH). The mice were injected twice daily (B.I.D) with subcutaneous calcium lactate (2 mg/kg) for 4 weeks.

Example 14. Animal Model for Age-Related Macular Degeneration

All experiments were performed under the institutional guidelines established by the Institutional Animal Care and Use Committee at Gachon University (IACUC-2017-0008). Six-week-old female C57BL/6 mice (20-25 g) were purchased from Orient (Charles River Korea, Seoul, Korea). All animals were maintained in a 12-hour light/dark cycle (light on, 08:00) at 22° C.-25° C. with free access to food and water. The mice were placed individually in an induction chamber, and anesthesia was induced with 2% isoflurane (HANA PHARM CO., Seoul, Korea). The lesions were induced in each eye of the mice by laser photocoagulation (SDL405-700, SD Laser, China). The laser pulses were from blue laser (wavelength, 405 nm; SD Laser). Laser parameters were 100 µm spot size, 700 mw power and 1 s exposure time. A total of 15 mice were randomized into three groups: (i) not subjected to laser induction (n=3); (ii) subjected to laser burns and injected with the vehicle buffer (n=5); and (iii) CaLa, 2 mg/kg/day (B.I.D) (n=7). CaLa treatment was started the days after laser photocoagulation and was treated subcutaneously for 14 days. (33, 34)

Example 15. Histological Analysis for NASH Model

Mouse liver tissues (n=5) were dissected and fixed in 4% paraformaldehyde PBS solution for 15 h at 4° C. Fixed liver tissues were embedded in paraffin and sectioned at 10 µm. Slides were incubated at 55° C. for 2 h, and subsequently deparaffinized in xylene and rehydrated in a graded ethanol series and used for hematoxylin (Merck, Darmstadt, Germany) and eosin (H&E) staining (35). Paraffin sections (10 µm thick) stained with H&E were imaged using a Leica DM 1000 LED microscope (Leica Microsystems, Wetzlar, Germany).

Example 16. Histological Analysis for Age-Related Macular Degeneration

The histopathologic examination of retinal lesions was performed 2 weeks after 2 mg/kg of CaLa was administered subcutaneously. The enucleated eyes were fixed with 4% paraformaldehyde (PFA) for 24 h at 4° C., and eyes obtained by removing the anterior segments were washed three times in phosphate-buffered saline. The fixed flat-mounts were dehydrated in a graded series of ethanol and embedded in paraffin. Paraffin sections (10 µm thick) were stained with hematoxylin (Merck, Darmstadt, Germany) and eosin (Sigma-Aldrich, St Louis, MO, USA) (H&E) and were imaged using a Leica DM 1000 LED microscope (Leica Microsystems, Wetzlar, Germany). The choroidal lesion and neovascularization on the flat-mounts were observed by confocal microscopy (Carl Zeiss, Oberkochen, Germany).

Example 17. Masson Trichrome Stain

Mouse liver tissues (n=5) were dissected and fixed in 4% paraformaldehyde PBS solution for 15 h at 4° C. Fixed tissues were embedded in paraffin and sectioned at 5 mm. Slides were incubated at 55° C. for 2 h, and subsequently deparaffinized in xylene and rehydrated in a graded ethanol series and re-fix in Bouin's solution for 1 hr at 56° C., remove the yellow color to rinse running tap water for 5-10 min and stained Biebrich scarlet-acid fuchsin solution for 5 min then in phosphomolybdic-phosphotungstic acid solution (ratio 1:1) for 30 minutes, and aniline blue solution and stain for 15 minutes. Rinse briefly in distilled water and in 1% acetic acid solution for 2-5 min. Dehydrate 95% ethyl alcohol, absolute ethyl alcohol and clear in xylene. Mount with mounting medium. Imaged using a Leica DM 1000 LED microscope (Leica Microsystems, Wetzlar, Germany).

Example 18. Results

FIG. 1 is an in vitro experiment of human leukemic monocytes. Western blot results show that inflammatory factor (NF-κb) was decreased by 2.5 mM calcium lactate treatment in THP-1 cells (human leukemic monocyte) hypoxia condition.

Figure 2:
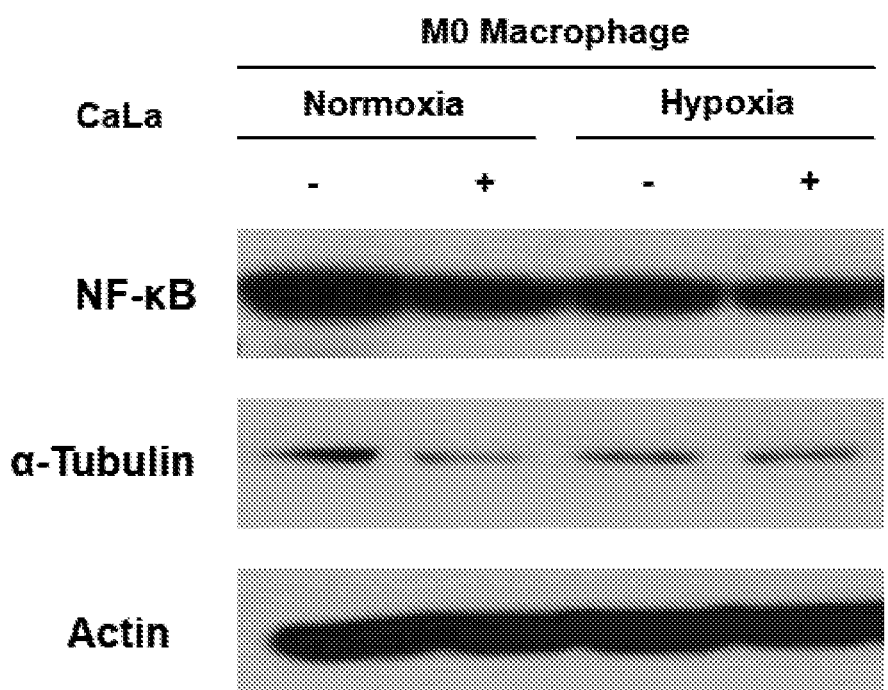
FIG. 2. In vitro experiment of human leukemic monocytes differentiated into macrophages. Western blot results indicated that inflammatory factor (NF-κb) was decreased by 2.5 mM calcium lactate treatment in differentiated THP-1 cells with PMA (phorbol-12-myristate-13-acetate) (M0 macrophage) under normoxia and hypoxia conditions.

FIG. 2 is an in vitro experiment of human leukemic monocytes differentiated into macrophages. Western blot results show that inflammatory factor (NF-κb) was decreased by 2.5 mM calcium lactate treatment in differentiated THP-1 cells with PMA (phorbol-12-myristate-13-acetate) (M0 macrophage) under normoxia and hypoxia conditions.

Figure 3:
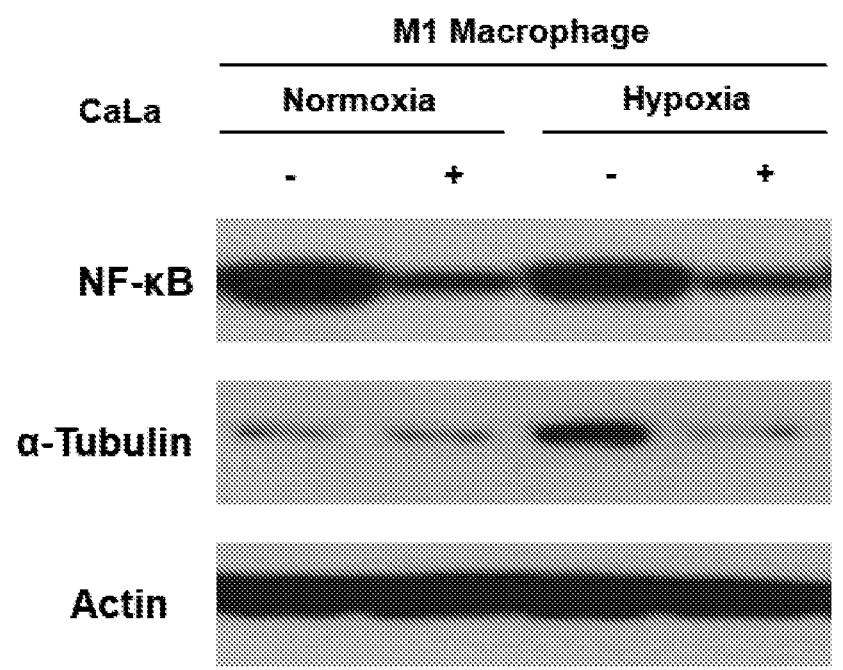
FIG. 3. Western blot results indicated that inflammatory factor (NF-κb) was decreased by 2.5 mM calcium lactate treatment in differentiated THP-1 cells with interferon gamma (IFN-γ) and Lipopolysaccharide (LPS) (M1 macrophage) under normoxia and hypoxia conditions.

FIG. 3 provides Western blot results showing that inflammatory factor (NF-κb) was decreased by 2.5 mM calcium lactate treatment in differentiated THP-1 cells with interferon gamma (IFN-γ) and lipopolysaccharide (LPS) (M1 macrophage) under normoxia and hypoxia conditions.

Figure 4:
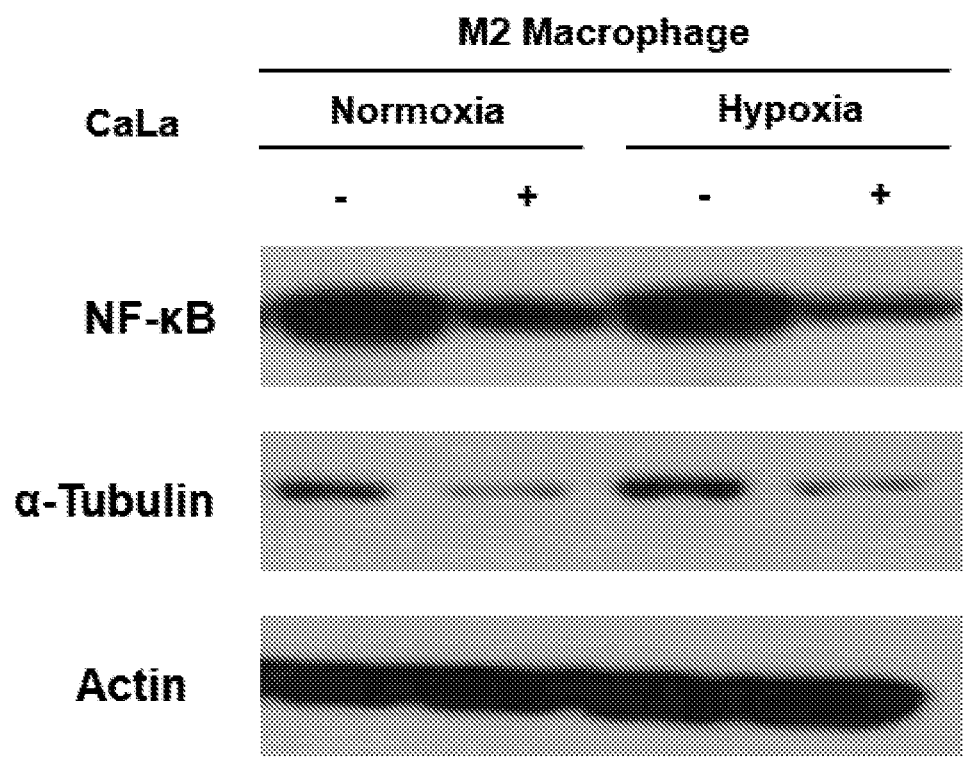
FIG. 4. Western blot results indicated that inflammatory factor (NF-κb) was decreased by 2.5 mM calcium lactate treatment in differentiated THP-1 cells with interleukin-4 (IL-4) and interleukin-10 (IL-10) (M2 macrophage) under normoxia and hypoxia conditions.

FIG. 4 provides Western blot results showing that inflammatory factor (NF-κb) was decreased by 2.5 mM calcium lactate treatment in differentiated THP-1 cells with interleukin-4 (IL-4) and interleukin-10 (IL-10) (M2 macrophage) under normoxia and hypoxia conditions.

Figure 5:
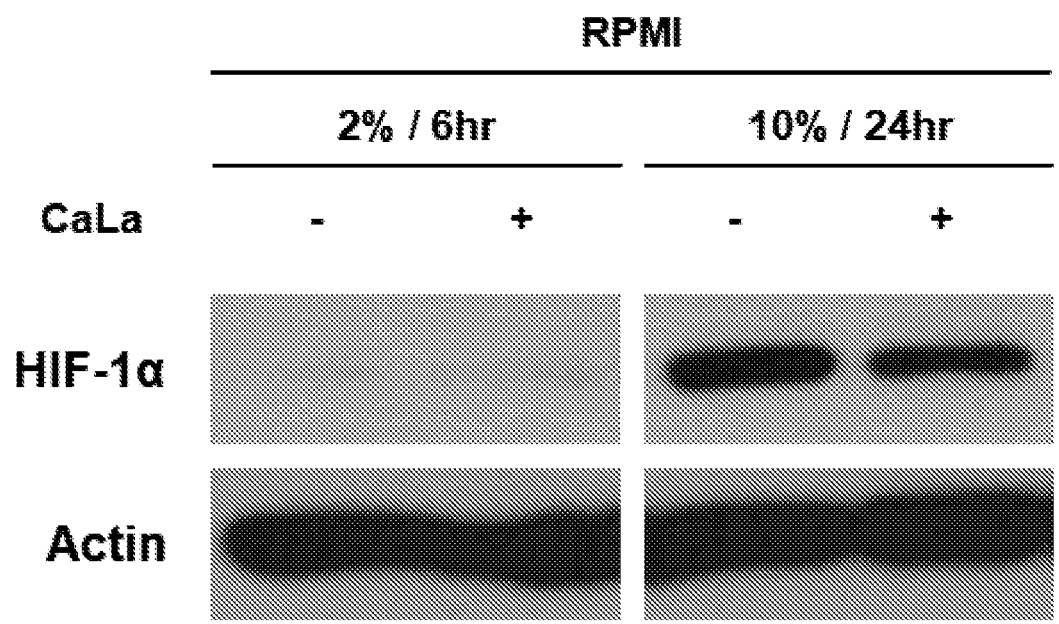
FIG. 5. Liver fibrosis in vitro experiment. Western blot results indicated that hypoxia inducible factor-1α (HIF-1α) was decreased by 2.5 mM calcium lactate treatment in LX-2 cells (human hepatic stellate cell) under hypoxia condition.

FIG. 5 is a liver fibrosis in vitro experiment. Western blot results show that hypoxia inducible factor-1α (HIF-1α) was decreased by 2.5 mM calcium lactate treatment in LX-2 cells (human hepatic stellate cell) under hypoxia condition.

Figure 6:
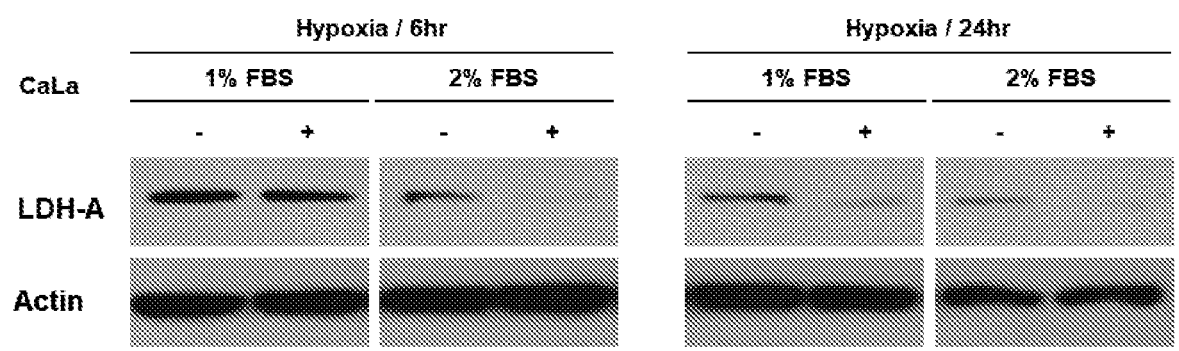
FIG. 6. Human endothelia cells in vitro experiment. Western blot results indicated that hypoxia-mediated factors (lactate dehydrogenase A) were decreased by 2.5 mM calcium lactate treatment in human umbilical vein endothelial cells under hypoxia condition.

FIG. 6 is a human endothelial cell in vitro experiment. Western blot results show that hypoxia-mediated factors (lactate dehydrogenase A) were decreased by 2.5 mM calcium lactate treatment in human umbilical vein endothelial cells under hypoxia condition.

Figure 7:
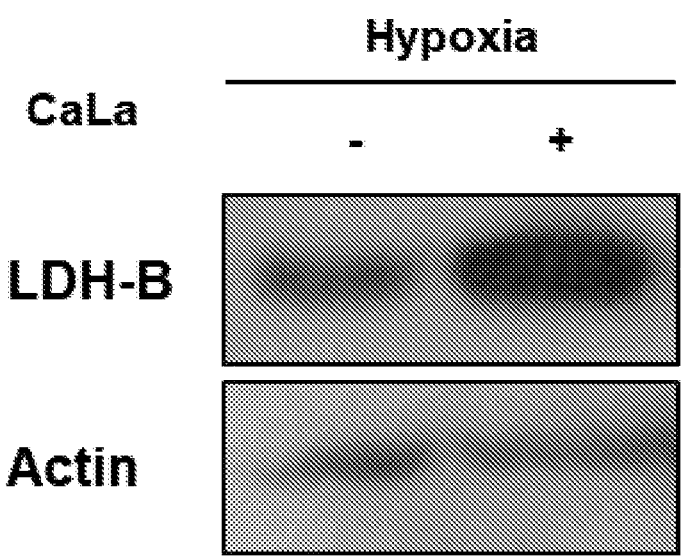
FIG. 7. Human fibroblast in vitro experiment. Western blot results indicated that lactate dehydrogenase B was increased by 2.5 mM calcium lactate treatment in CCD-18Co cells (human colon fibroblast) under hypoxia condition.

FIG. 7 is a human fibroblast in vitro experiment. Western blot results show that lactate dehydrogenase B was increased by 2.5 mM calcium lactate treatment in CCD-18Co cells (human colon fibroblast) under hypoxia condition.

Figure 8:
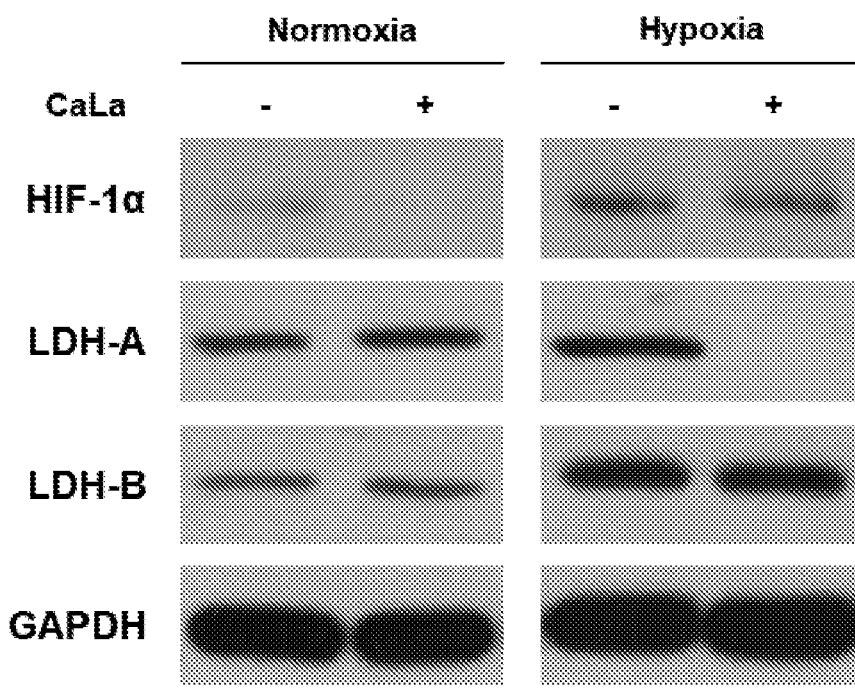
FIG. 8. Brain CID in vitro experiment. Western blot results indicated that hypoxia-mediated factors were decreased by 2.5 mM calcium lactate treatment in SK-N-SH cells (brain epithelium) under normoxia and hypoxia conditions.

FIG. 8 is a brain CID in vitro experiment. Western blot results show that hypoxia-mediated factors were decreased by 2.5 mM calcium lactate treatment in SK-N-SH cells (brain epithelium) under normoxia and hypoxia conditions.

Figure 9:
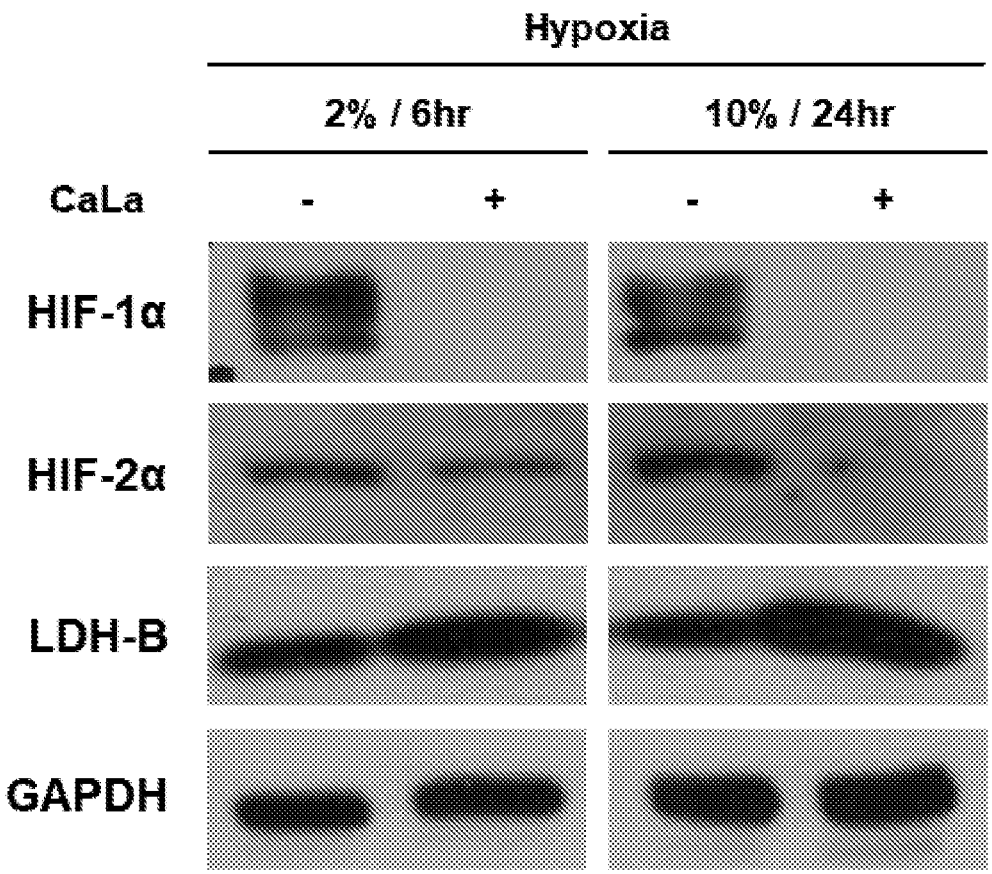
FIG. 9. Liver CID in vitro experiment. Western blot results indicated that hypoxia-mediated factors were changed by 2.5 mM calcium lactate treatment in HepG2 cells (liver epithelium) under hypoxia condition.

FIG. 9 is a liver CID in vitro experiment. Western blot results show that hypoxia-mediated factors were changed by 2.5 mM calcium lactate treatment in HepG2 cells (liver epithelium) under hypoxia condition.

Figure 10:
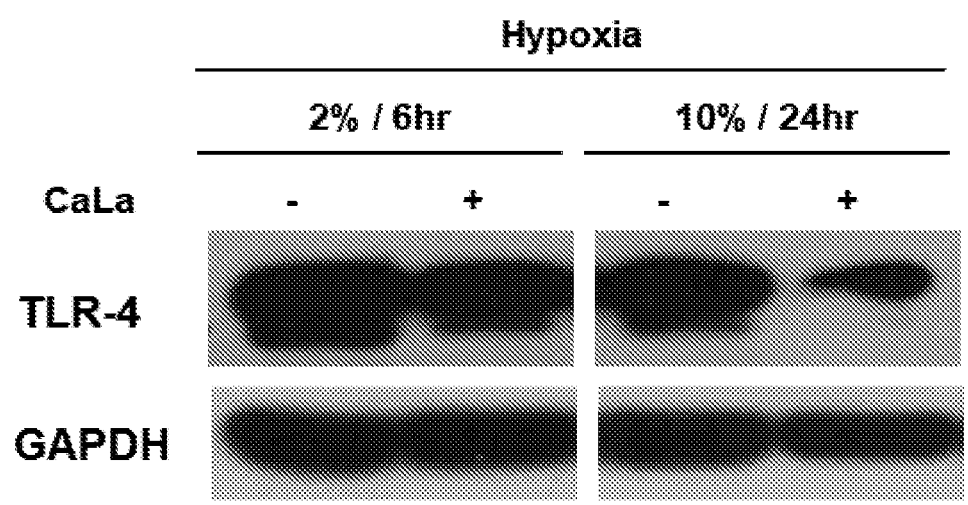
FIG. 10. Western blot results indicated that inflammatory factor (TLR-4) was decreased by 2.5 mM calcium lactate treatment in HepG2 cells (liver epithelium) under hypoxia condition.

FIG. 10 provides Western blot results showing that inflammatory factor (TLR-4) was decreased by 2.5 mM calcium lactate treatment in HepG2 cells (liver epithelium) under hypoxia condition.

Figure 11:
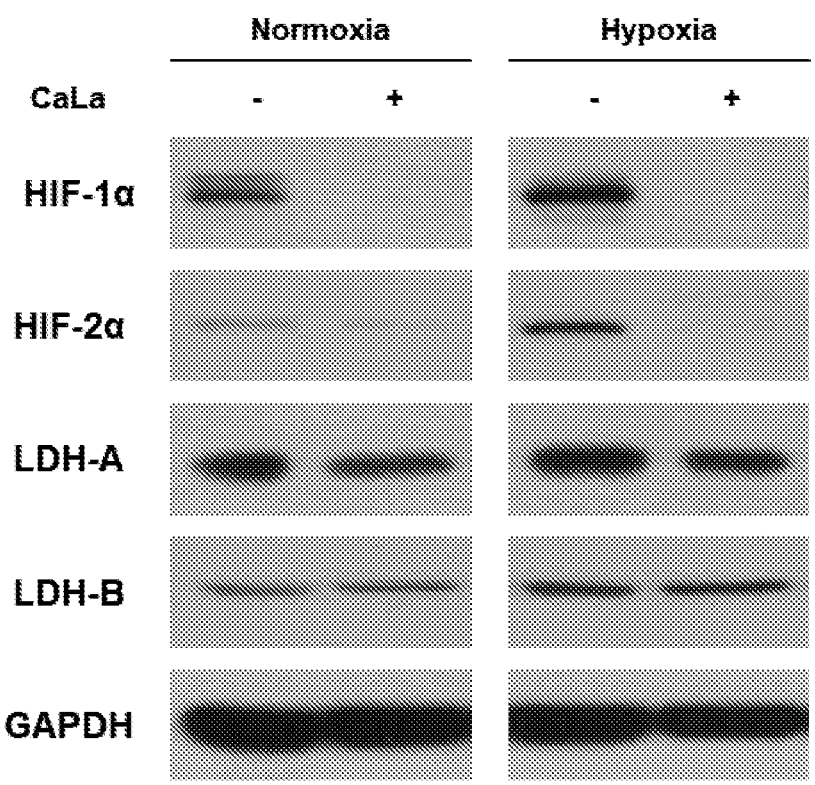
FIG. 11. Eye CID in vitro experiment. Western blot results indicated that hypoxia-mediated factors were decreased by 2.5 mM calcium lactate treatment in ARPE-19 cells (retinal pigment epithelium) under normoxia and hypoxia conditions.

FIG. 11 is an eye CID in vitro experiment. Western blot results show that hypoxia-mediated factors were decreased by 2.5 mM calcium lactate treatment in ARPE-19 cells (retinal pigment epithelium) under normoxia and hypoxia conditions.

Figure 12:
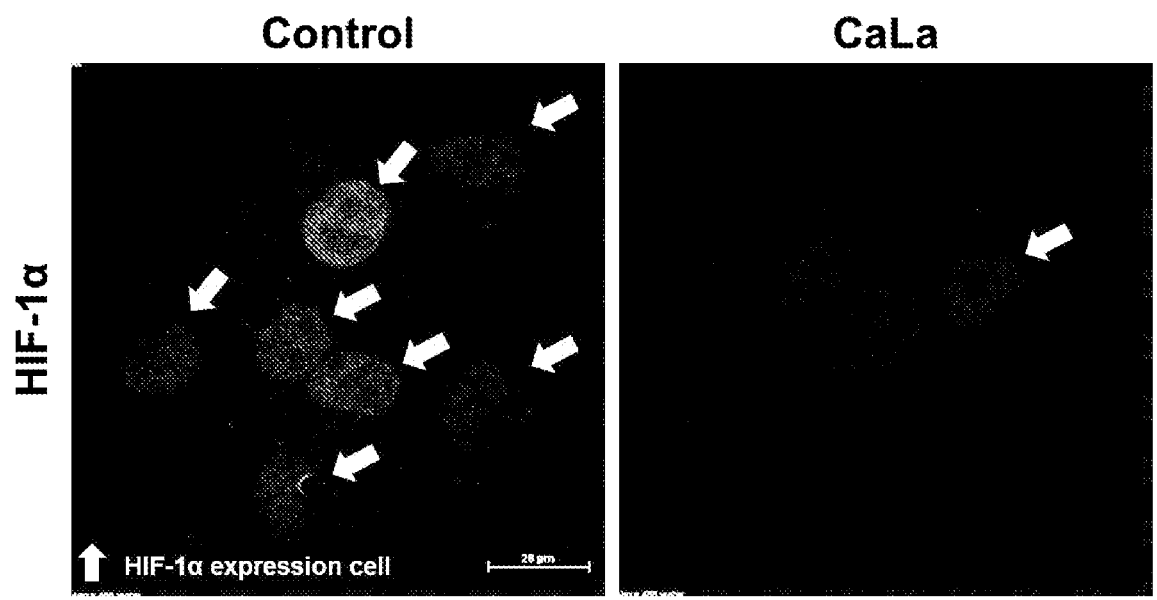
FIG. 12. Immunocytochemistry results indicated that hypoxia inducible factor-1α (HIF-1α) was decreased by 2.5 mM calcium lactate treatment in ARPE-19 cells (retinal pigment epithelium) under hypoxia condition.

FIG. 12 provides immunocytochemistry results showing that hypoxia inducible factor-1α (HIF-1α) was decreased by 2.5 mM calcium lactate treatment in ARPE-19 cells (retinal pigment epithelium) under hypoxia condition.

Figure 13:
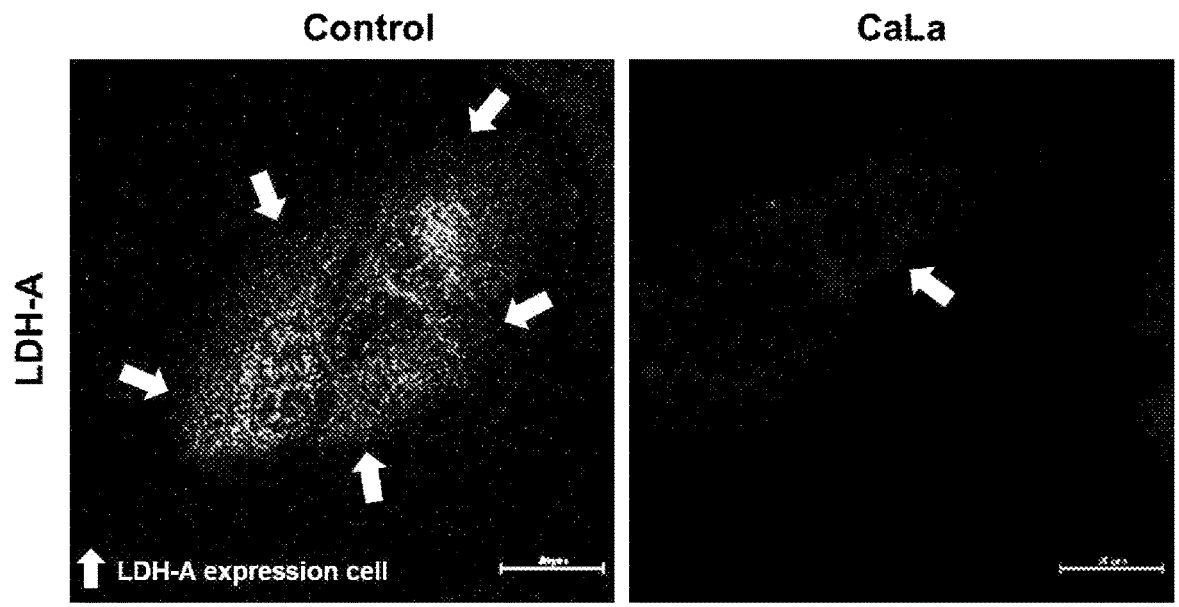
FIG. 13. The immunocytochemical results indicated that lactate dehydrogenase A was decreased by 2.5 mM calcium lactate treatment in the ARPE-19 cells (retinal pigment epithelium) under normoxia condition.

FIG. 13 provides immunocytochemical results showing that lactate dehydrogenase A was decreased by 2.5 mM calcium lactate treatment in the ARPE-19 cells (retinal pigment epithelium) under normoxia condition.

Figure 14:
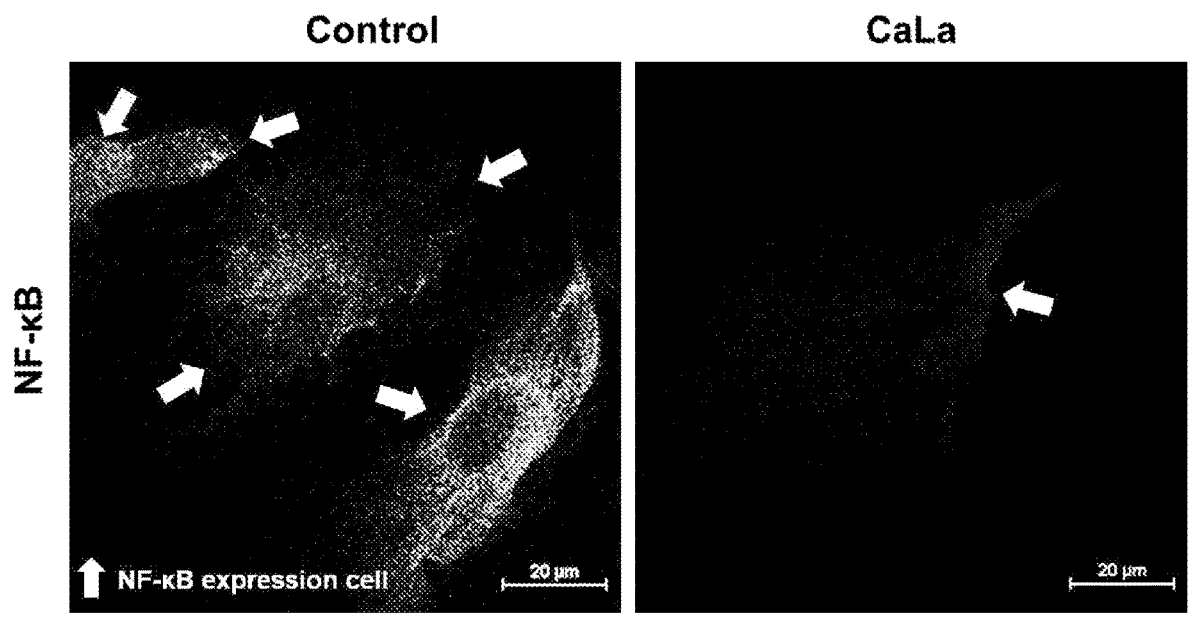
FIG. 14. The immunocytochemical results indicated that inflammatory factor (nuclear factor-kappa B) was decreased by 2.5 mM calcium lactate treatment in the ARPE-19 cells (retinal pigment epithelium) under hypoxia condition.

FIG. 14 provides immunocytochemical results showing that inflammatory factor (nuclear factor-kappa B) was decreased by 2.5 mM calcium lactate treatment in the ARPE-19 cells (retinal pigment epithelium) under hypoxia condition.

Figure 15:
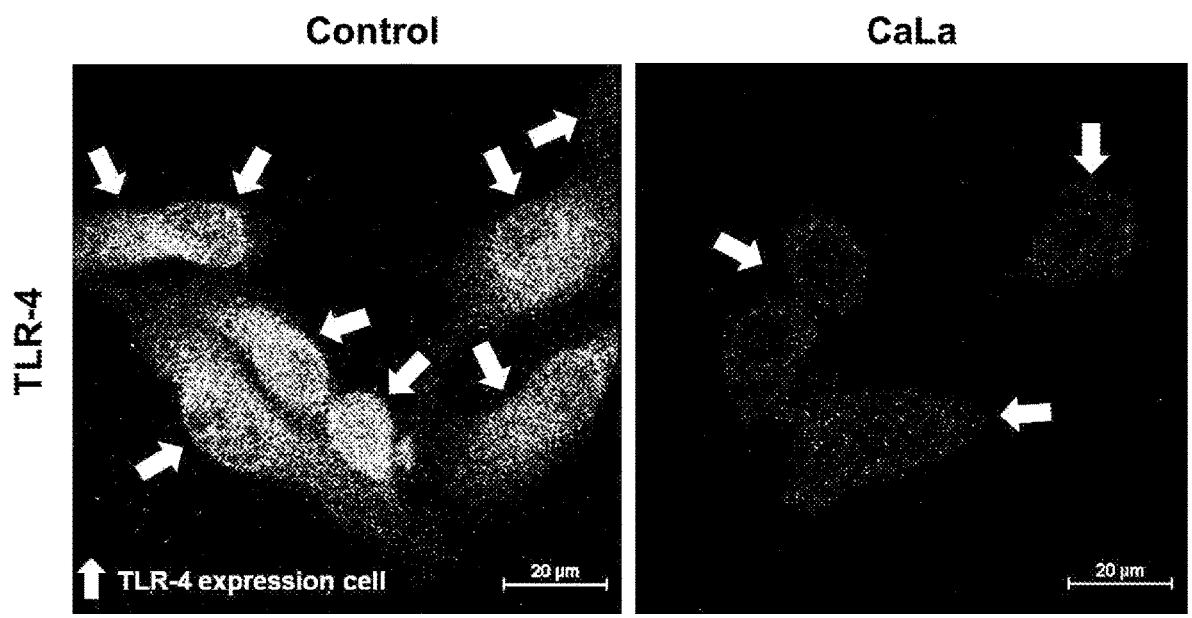
FIG. 15. The immunocytochemical results indicated that inflammatory factor (toll like receptor 4) was decreased by 2.5 mM calcium lactate treatment in the ARPE-19 cells (retinal pigment epithelium) under hypoxia condition.

FIG. 15 provides immunocytochemical results showing that inflammatory factor (toll like receptor 4) was decreased by 2.5 mM calcium lactate treatment in the ARPE-19 cells (retinal pigment epithelium) under hypoxia condition.

Figure 16:
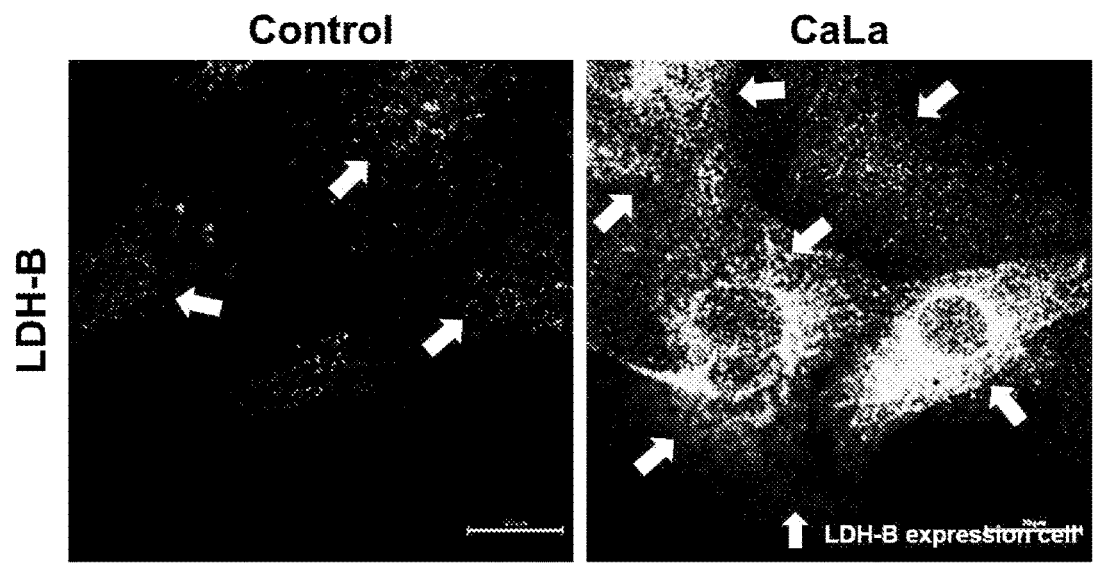
FIG. 16. The immunocytochemical results indicated that lactate dehydrogenase B was increased by 2.5 mM calcium lactate treatment in the ARPE-19 cells (retinal pigment epithelium) under hypoxia condition.

FIG. 16 provides immunocytochemical results showing that lactate dehydrogenase B was increased by 2.5 mM calcium lactate treatment in the ARPE-19 cells (retinal pigment epithelium) under hypoxia condition.

Figure 17:
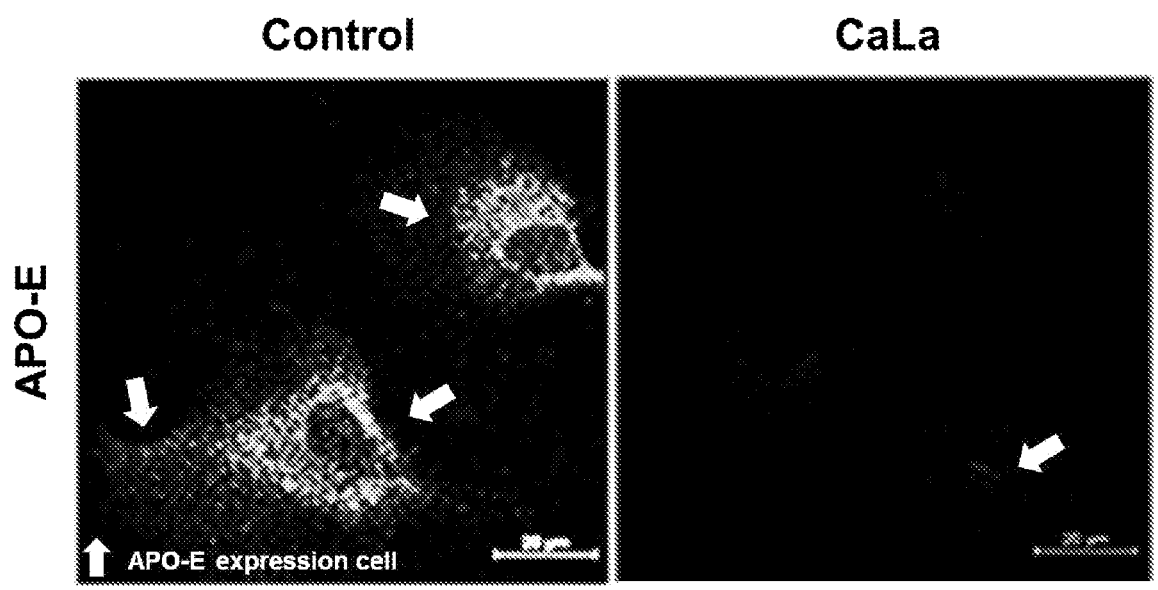
FIG. 17. The immunocytochemical results indicated that drusen marker (Apolipoprotein E) was decreased by 2.5 mM calcium lactate treatment in the ARPE-19 cells (retinal pigment epithelium) under hypoxia condition.

FIG. 17 provides immunocytochemical results showing that drusen marker (Apolipoprotein E) was decreased by 2.5 mM calcium lactate treatment in the ARPE-19 cells (retinal pigment epithelium) under hypoxia condition.

Figure 18:
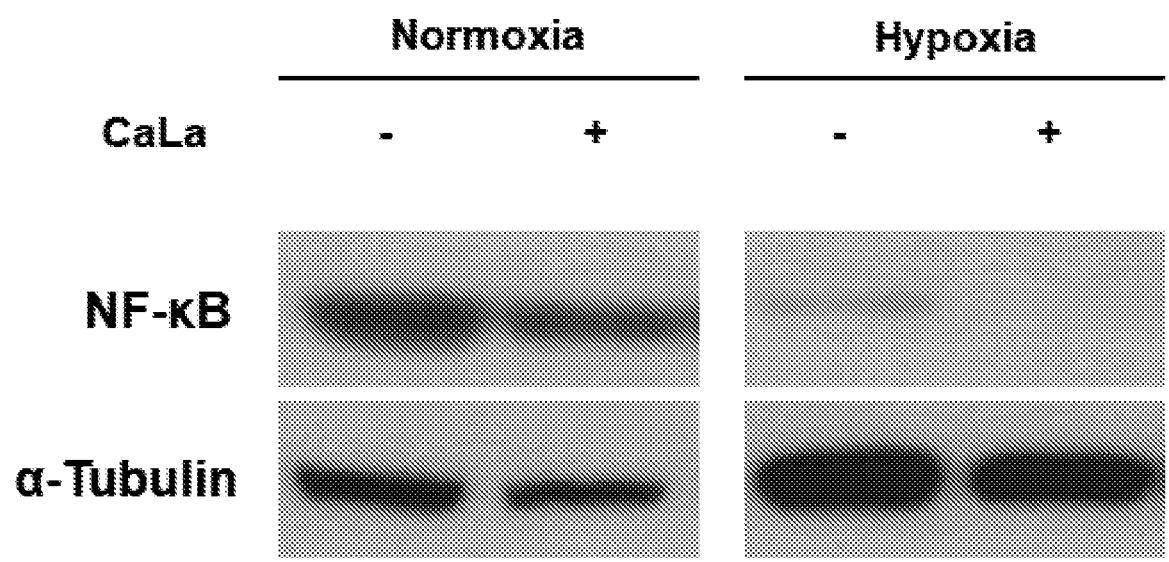
FIG. 18. Western blot results indicated that inflammatory factor (NF-κb) was decreased by 2.5 mM calcium lactate treatment in ARPE-19 cells (retinal pigment epithelium) under hypoxia condition.

FIG. 18 provides Western blot results showing that inflammatory factor (NF-κb) was decreased by 2.5 mM calcium lactate treatment in ARPE-19 cells (retinal pigment epithelium) under hypoxia condition.

Figure 19:
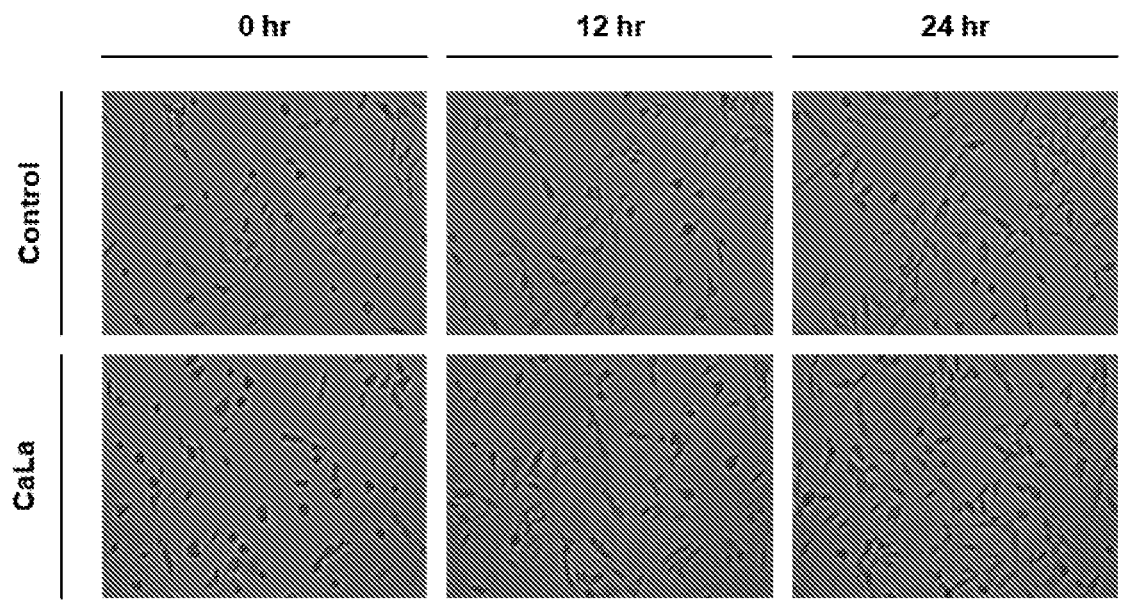
FIG. 19. The photos show that there is no toxicity in ARPE-19 cells (retinal pigment epithelium) by 2.5 mM calcium lactate treatment. Calcium lactate only plays an important role in the metabolic change of injured epithelial cells.

FIG. 19 shows that there is no toxicity in ARPE-19 cells (retinal pigment epithelium) by 2.5 mM calcium lactate treatment. Calcium lactate only plays an important role in the metabolic change of injured epithelial cells.

Figure 25:
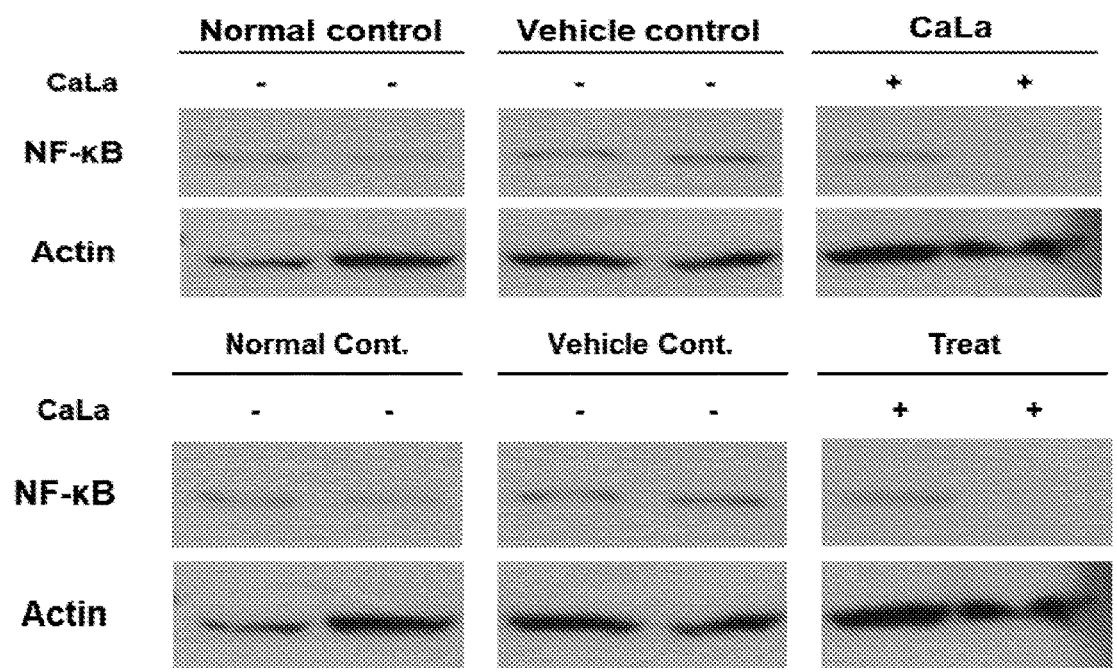
FIG. 25. Western blot results indicated that inflammatory factor (NF-κB) was decreased by 2.5 mM calcium lactate treatment in the tissue of retinal pigment epithelium.

FIG. 25 provides Western blot results showing that inflammatory factor (NF-κb) was decreased by 2.5 mM calcium lactate treatment in the tissue of retinal pigment epithelium.

Example 19. Targeting Digestive Disease (NFALD, NASH)

Materials and Methods

Animal Model for liver diseases. All experiments were performed under the institutional guidelines established by the Institutional Animal Care and Use Committee at Gachon University (IACUC-2017-0008). Female 5-week-old C57BL/6 mice were purchased form KOATEC (Pyeongtaek, South Korea) and were fed Methionine-Choline (MCD) diet for 4 weeks. The mice were injected twice daily (B.I.D) with subcutaneous calcium lactate (2 mg/kg) for 4 weeks. Histological analysis. Mouse Liver tissues (n=5) were dissected and fixed in 4% paraformaldehyde PBS solution for 15 h at 4° C. Fixed liver tissues were embedded in paraffin and sectioned at 10 μm. Slides were incubated at 55° C. for 2 h, and subsequently deparaffinized in xylene and rehydrated in a graded ethanol series and used for hematoxylin (Merck, Darmstadt, Germany) and eosin (H&E) staining. Paraffin sections (10 μm thick) stained with H&E were imaged using a Leica DM 1000 LED microscope (Leica Microsystems, Wetzlar, Germany Masson Trichrome Stain. Mouse Liver tissues (n=5) were dissected and fixed in 4% paraformaldehyde PBS solution for 15 h at 4° C. Fixed tissues were embedded in paraffin and sectioned at 5 mm. Slides were incubated at 55° C. for 2 h, and subsequently deparaffinized in xylene and rehydrated in a graded ethanol series and re-fix in Bouin's solution for 1 hr at 56° C., remove the yellow color to rinse running tap water at 5-10 min and stained Biebrich scarlet-acid fuchsin solution for 5 min than in phosphomolybdic-phosphotungstic acid solution (ratio 1:1) for 30 minutes, and aniline blue solution and stain for 15 minutes. Rinse briefly in distilled water and in 1% acetic acid solution for 2-5 minutes. Dehydrate 95% ethyl alcohol, absolute ethyl alcohol and clear in xylene. Mount with mounting medium. Imaged using a Leica DM 1000 LED microscope (Leica Microsystems, Wetzlar, Germany).

Figure 20:
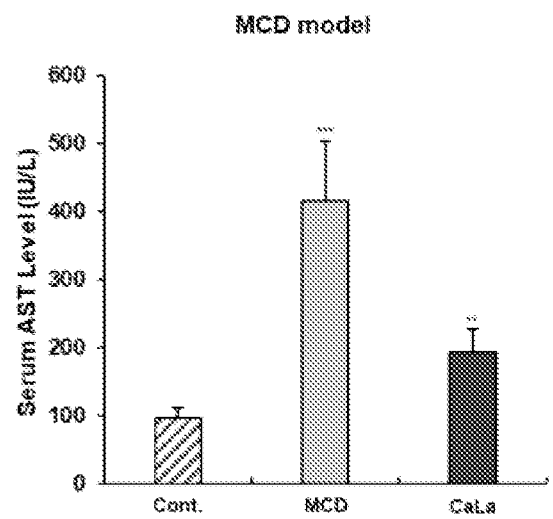
FIG. 20. Liver CID (NASH) in vivo experiment. The blood chemistry results indicated that serum aspartate aminotransferase (AST) and alanine aminotransferase (ALT) were significantly decreased by 2 mg/kg calcium lactate treatment. **P<0.001 vs. methionine-choline deficient (MCD). Results are MEAN±SD.
Figure 20:
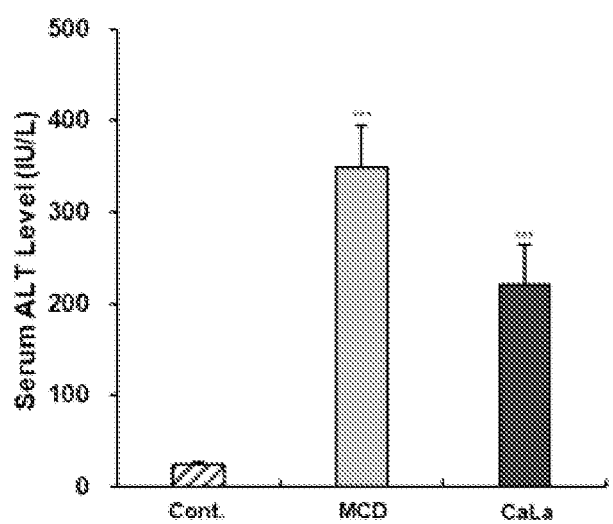

FIG. 20 is a liver CID (NASH) in vivo experiment. To induce NASH, mice were fed methionine-choline deficient (MCD) diet with polyunsaturated fat for 8 weeks. The blood chemistry results show that serum AST and ALT were significantly decreased by 2 mg/kg calcium lactate treatment. **P<0.001 vs. methionine-choline deficient (MCD). Results are MEAN±SD.

Figure 21:
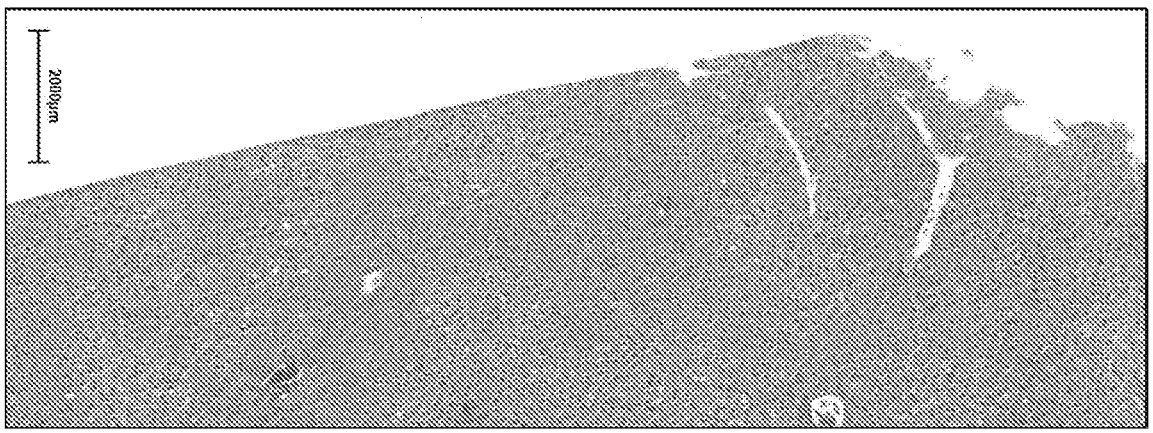
FIG. 21. Immunohistochemical results show that in the liver steatosis was prevented by 2 mg/kg calcium lactate treatment.
Figure 21:
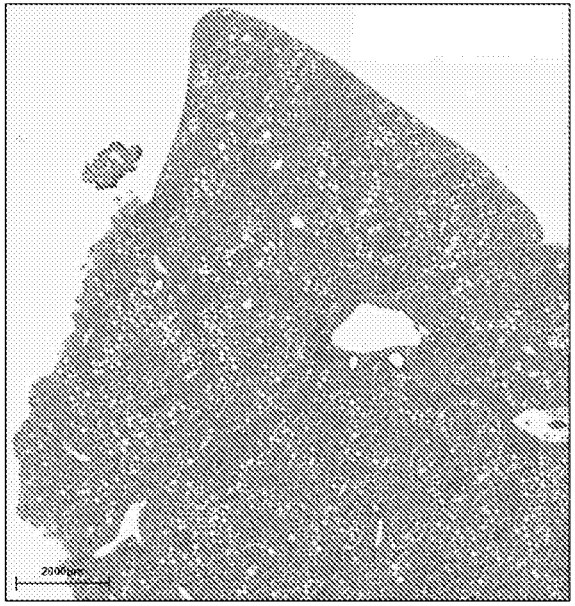
Figure 21:
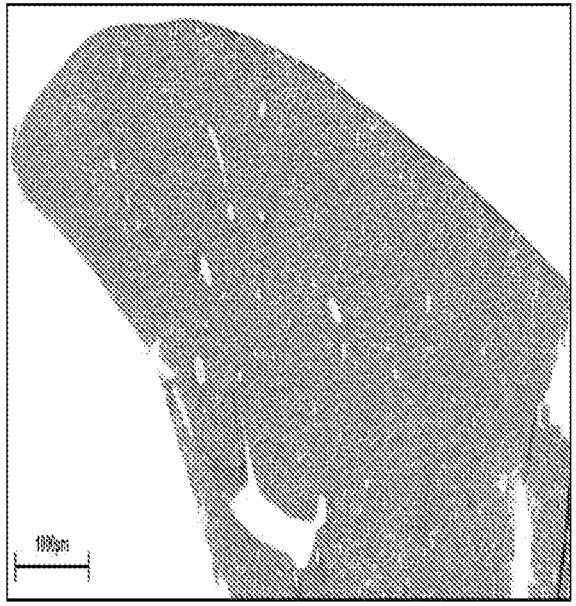

FIG. 21 provides immunohistochemical results showing that lipid droplets (white pores in liver tissues) were not observed in the calcium lactate-treated group while the lipid droplets were well observed in the methionine-choline deficient (MCD) group. Wteatosis was prevented by 2 mg/kg calcium lactate treatment. The results show that steatosis is prevented by calcium lactate treatment.

Figure 22B:
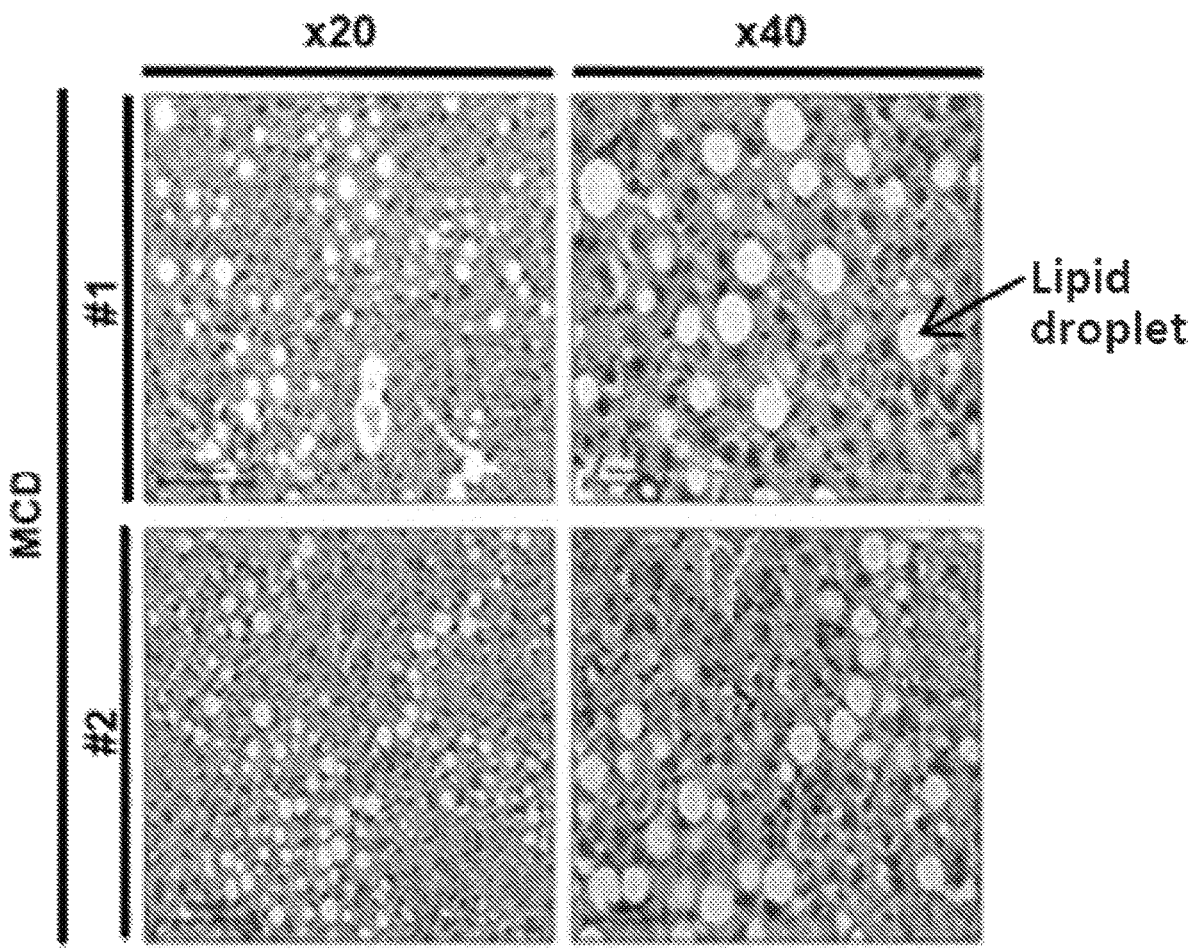
Figure 22C:
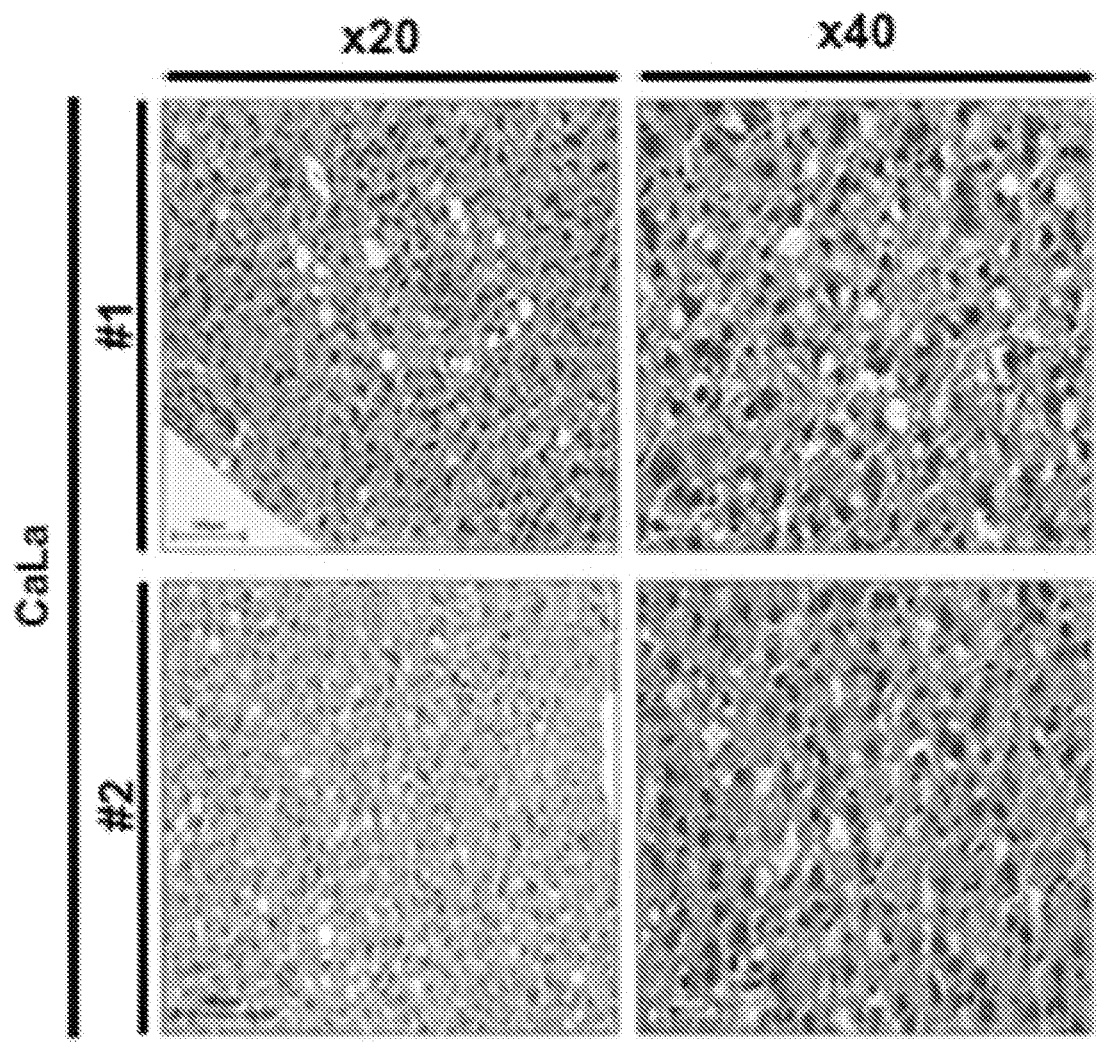

FIGS. 22A, 22B, and 22C provide immunohistochemical results showing that in the liver lipid droplets (white pores in liver tissues) are not present in the 2 mg/kg calcium lactate-treated group, similar to the control group, while they are found in the methionine-choline deficient (MCD) group.

Figure 23:
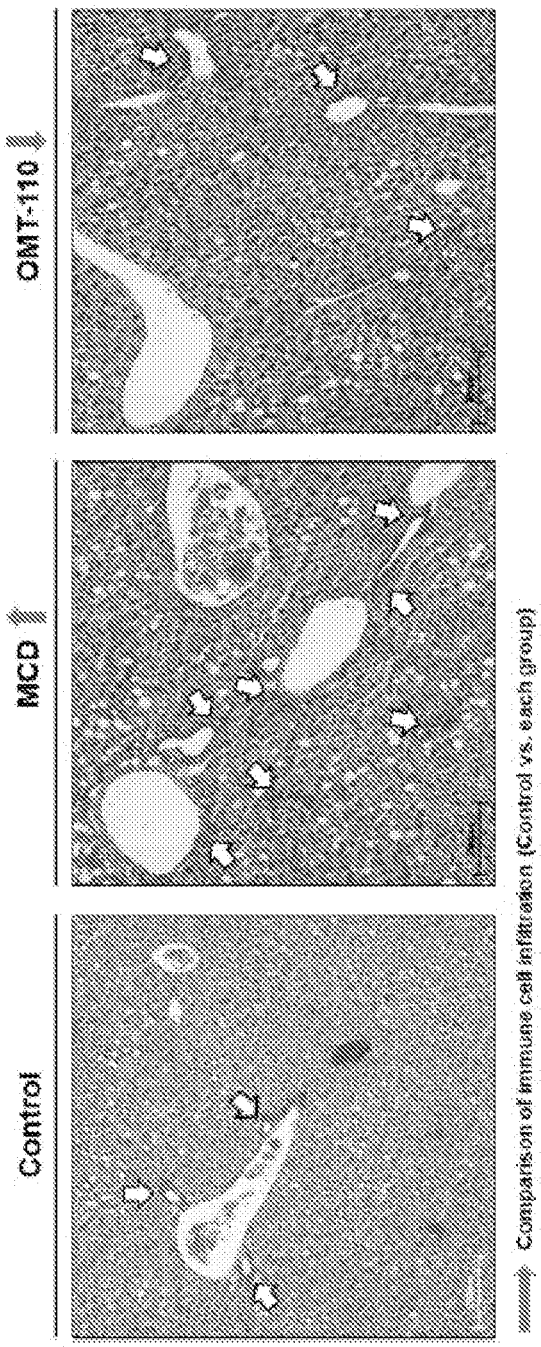
FIG. 23. Immunohistochemical results show that in the liver immune cell infiltration is decreased in the 2 mg/kg calcium lactate-treated group, similar to the control group, while immune cell infiltration is increased in the methionine-choline deficient (MCD) group.

FIG. 23 provides immunohistochemical results showing that in the liver immune cell infiltration is decreased in the 2 mg/kg calcium lactate-treated group, similar to the control group, while immune cell infiltration is increased in the methionine-choline deficient (MCD) group.

Figure 24:
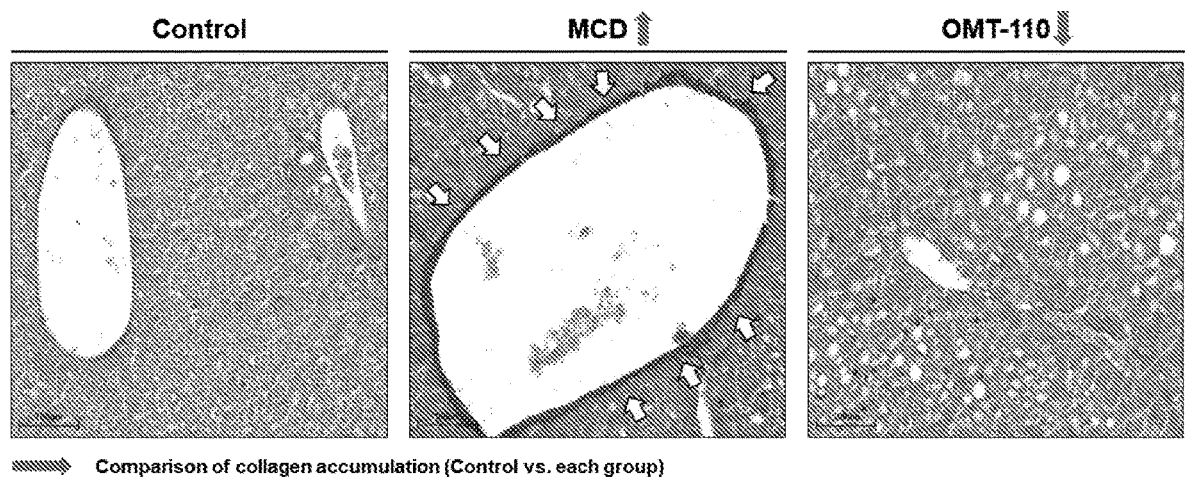
FIG. 24. Immunohistochemical results show that in the liver fibrosis is not present in the 2 mg/kg calcium lactate-treated group, similar to the control group, while it is present in the methionine-choline deficient (MCD) group.

FIG. 24 provides immunohistochemical results showing that in the liver fibrosis (collagen accumulation site; white arrows) is not present in the 2 mg/kg calcium lactate-treated group, similar to the control group, while it is present in the methionine-choline deficient (MCD) group.

Example 20. Targeting Ocular Disease (Age-Related Macular Degeneration (AMD), Keratitis, and Diabetic Retinopathy)

Materials and Methods

Animals. All experiments were performed under the institutional guidelines established by the Institutional Animal Care and Use Committee at Gachon University (IACUC-2017-0008). Six-week-old C57BL mice were purchased from Orient (Charles River Korea, Seoul, Korea). All animals were maintained in a 12-hour light/dark cycle (light on, 08:00) at 22-25° C. with free access to food and water.

Preparation of calcium lactate. Calcium lactate was purchased from Sigma Aldrich (St. Louis, MO, USA). Two mg/kg of calcium lactate was dissolved in saline for daily subcutaneous injection (21 days).

Animal model for ocular disease. The mice were placed individually in an induction chamber, and anesthesia was induced with 2% isoflurane (HANA PHARM CO., Seoul, Korea). The laser-induced rupture of Bruch's membrane was induced in both eyes of mice by laser photocoagulation (SDL405-700, SD Laser, China). The laser pulses were from green laser (wave length, 532 nm; Visulas, 532; SD Laser). Laser parameters were 100 µm spot size, 700 mw power and 1 s exposure time.

Preparation of choroidal flat mounts. Twenty one days after laser injury, mice in each group were anesthetized and perfused through the left ventricle with 1.0 mL PBS containing 25 mg fluorescein isothiocyanate-dextran (Sigma-Aldrich, St. Louis, MO, USA). Eyes were enucleated and fixed in 4% paraformaldehyde for 1 hour. Retinal pigment epithelium-choroid-sclera eyecups were prepared after hemisecting the eye, with total removal of the lens, vitreous body, and retina. Retinal pigment epithelium-choroid-sclera eyecups were flattened by the creation of four or five radial incisions, from the edge to the equator, and flat-mounted in aqua-mount.

Histological analysis. The fixed flat-mounts were dehydrated in a graded series of ethanol and embedded in paraffin. Paraffin sections (10 µm thick) were stained with hematoxylin (Merck, Darmstadt, Germany) and eosin (Sigma-Aldrich, St Louis, MO, USA) (H&E) and were imaged using a Leica DM 1000 LED microscope (Leica Microsystems, Wetzlar, Germany). The choroidal lesion and neovascularization on the flat-mounts were observed by confocal microscopy (Carl Zeiss, Oberkochen, Germany).

Results

Figure 26:
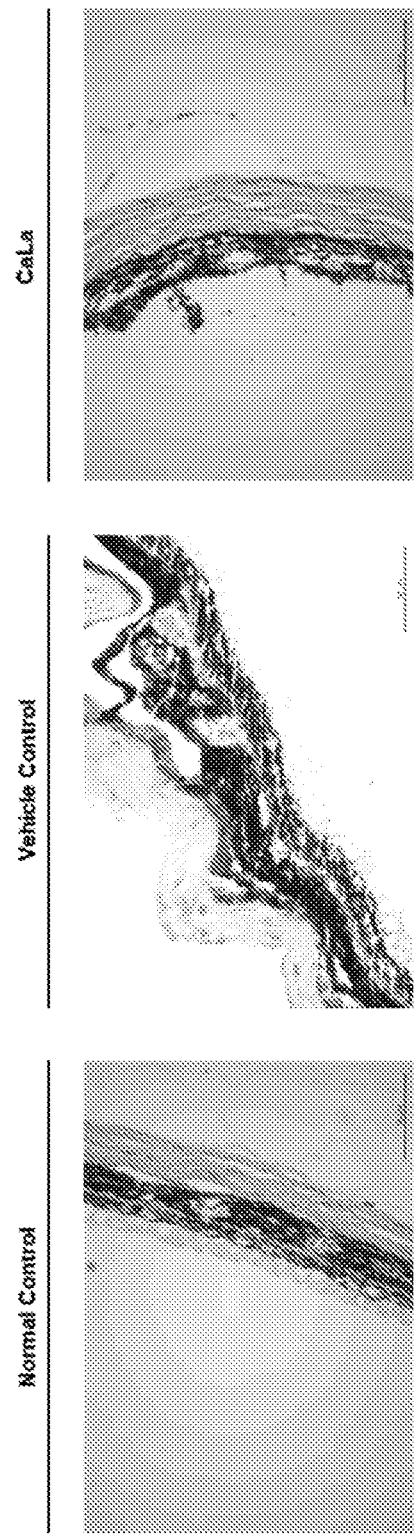
FIG. 26. Immunohistochemical results showed that the retinal pigment epithelium was recovered in a similar morphology to the normal control epithelium by treatment with 2.5 mM calcium lactate.

FIG. 26 provides representative images for H&E staining of lesion of inner layer of choroidal flat-mount. An abnormal morphology of retinal pigment epithelium was observed after AMD induction (middle image). The morphology of the retinal pigment epithelium was recovered in a similar manner to the normal control epithelium (left image) by treatment with 2.5 mM calcium lactate (right image).

Figure 27:
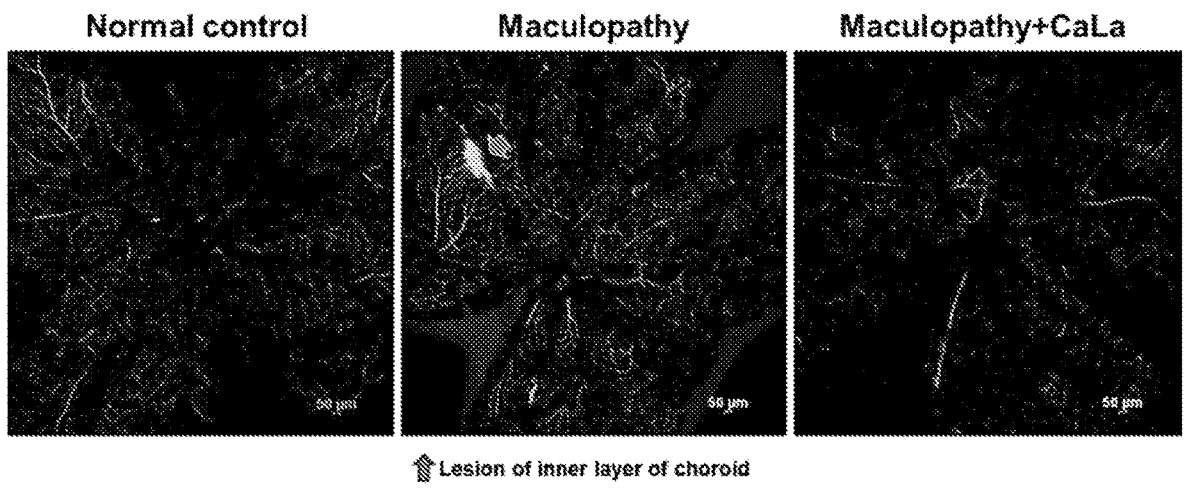
FIG. 27. Fluorescence images for lesion of inner layer of choroid on flat-mount by laser-induced age-related macular degeneration (AMD).

FIG. 27 provides fluorescence images for lesion of inner layer of choroid on flat-mount by laser-induced AMD. The choroidal lesion was observed after AMD induction (middle image). The choroidal lesion was restored after treatment with calcium lactate (right image).

Figure 28:
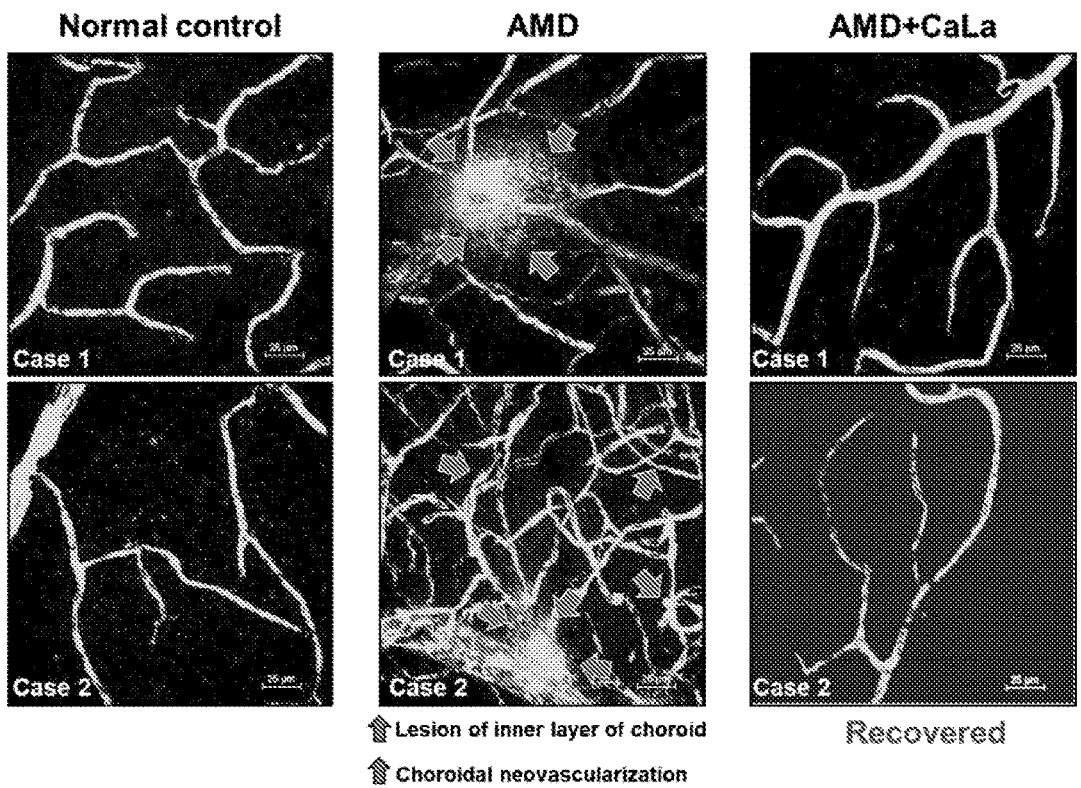
FIG. 28. Fluorescence images for lesion of inner layer and neovascularization of choroid on flat-mount by laser-induced age-related macular degeneration (AMD).

FIG. 28 provides fluorescence images for lesion of inner layer and neovascularization of choroid on flat-mount by laser-induced AMD. The choroidal lesion and neovascularization were observed after AMD induction (middle image). The choroidal lesion and neovascularization were restored after treatment with calcium lactate (right image), same with the normal control (left image).

Example 21. Targeting Alzheimer & Stroke

Materials and Methods

Animals. All experiments were carried out in accordance with animal care guidelines under Korean law (11737, rev'd Apr. 5, 2013) and the guidelines set by the Institutional Animal Care and Use Committee at Gachon university (LCDI-2018-0073). Eight-week old male Sprague-Dawley (SD) rats were obtained from Samtako Co. (Osan, Gyeonggi-do, Republic of Korea) and bred under specific-pathogen-free (SPF) conditions. All animals were maintained in a 12-hour light/dark cycle at 22-25° C. with free access to food and water.

Preparation of Lipopolysaccharides (LPS) and Calcium Lactate. Dissolve 1 mg of LPS powder in 1 ml of saline. Keep the tubes on ice if LPS is going to be used fresh. For long storage, screw cap vials are preferred. The aliquots were stored at −20° C. Calcium lactate was purchased from Sigma Aldrich (St. Louis, MO, USA). Two mg/kg of calcium lactate were dissolved in saline for daily subcutaneous injection (21 days).

Intracranial injection of LPS. The animals were placed in a small acrylic cage that was coupled with an anesthesia machine that allowed them to breathe freely under gaseous anesthesia (2% isoflurane, Spartanburg, SC, USA). After full anesthesia of an animal was achieved, it was positioned on an operating table (while maintaining the gaseous anesthesia) with the superior aspect of the neck hyperextended to expose the posterior region. The animal fur of head was shaved with an electric clipper, and the skin was swabbed with iodine. LPS was kept it on ice before use. All the surgical materials disinfected with 70% ethanol. Hamilton syringe barrel inner space was cleaned with distilled water and 70% ethanol. The Hamilton syringe was placed in the syringe holder. The animal in the stereotaxic apparatus was placed on horizontal position. A midline incision (about 1 cm) on the skin of head was made with the scalpel. The needle of Hamilton syringe was placed on the bregma. Read the three coordinates (AP: −3.6, LM: 2.0, and DV: −3.8) on the manipulator (in mm) and write them down; this was used for starting point. Slowly, set the DV coordinate of the injection point; this inserts the needle tip into the brain until the injection point. The LPS solution (2 µl) was released at an approximate flow rate of 0.5 µl/min. After the injection, the needle was removed very slowly. The wound area was closed by suturing, and then disinfectant was applied. The rat was marked for further identification.

Immunohistochemistry. Brain tissue was sectioned at 5 µm on cryostat and stained for histological examination. Microscopic images were obtained at 200× magnification. For immunohistochemistry, sections were blocked with 1% BSA and 10% NGS in 0.05 M PBS for 1 h at room temperature and then reacted with rabbit anti-Iba-1 (1:1000, Bioss, MA, USA) at 4° C. two overnights. ABC staining system was used to visualize microglia (Iba-1) in the sections (Vector Laboratories, CA, USA).

Results

Figure 29:
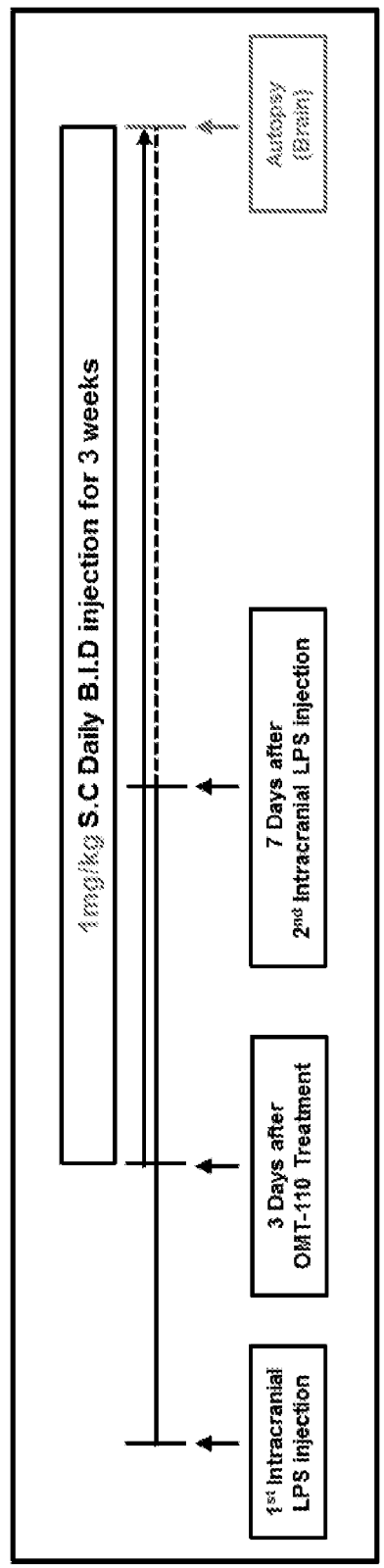
FIG. 29. Experimental scheme for establishing Alzheimer's disease and stroke.
Figure 30:
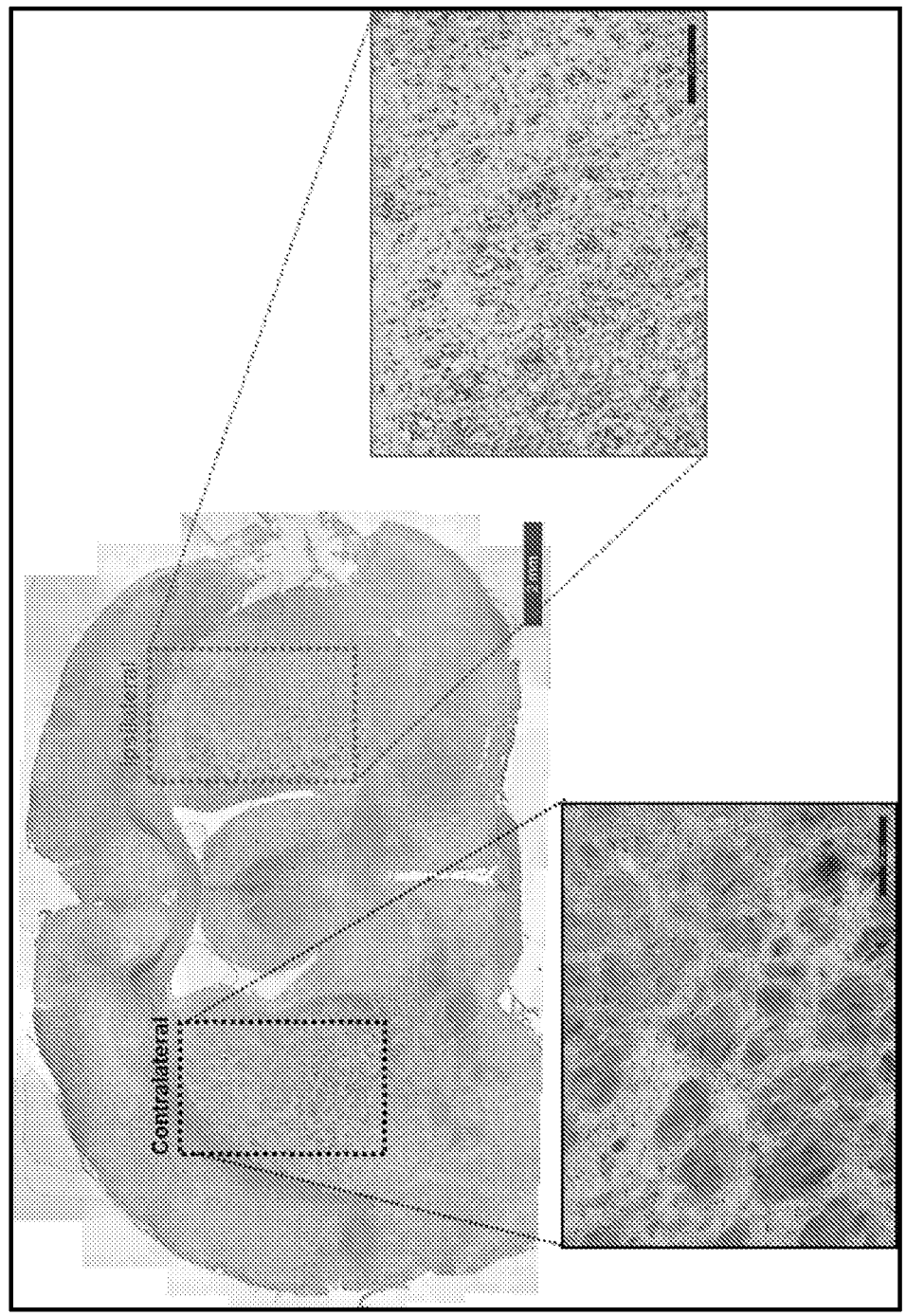
FIG. 30. Representative images for brain damage by lipopolysaccharide (LPS). Contralateral: normal region. Ipsilateral: LPS injection.

FIG. 29 provides an experimental scheme for establishing Alzheimer and stroke diseases. OMT-110 is calcium lactate. FIG. 30 provides representative images for showing brain damage by LPS. Contralateral: normal region. Ipsilateral: LPS injection.

Figure 31:
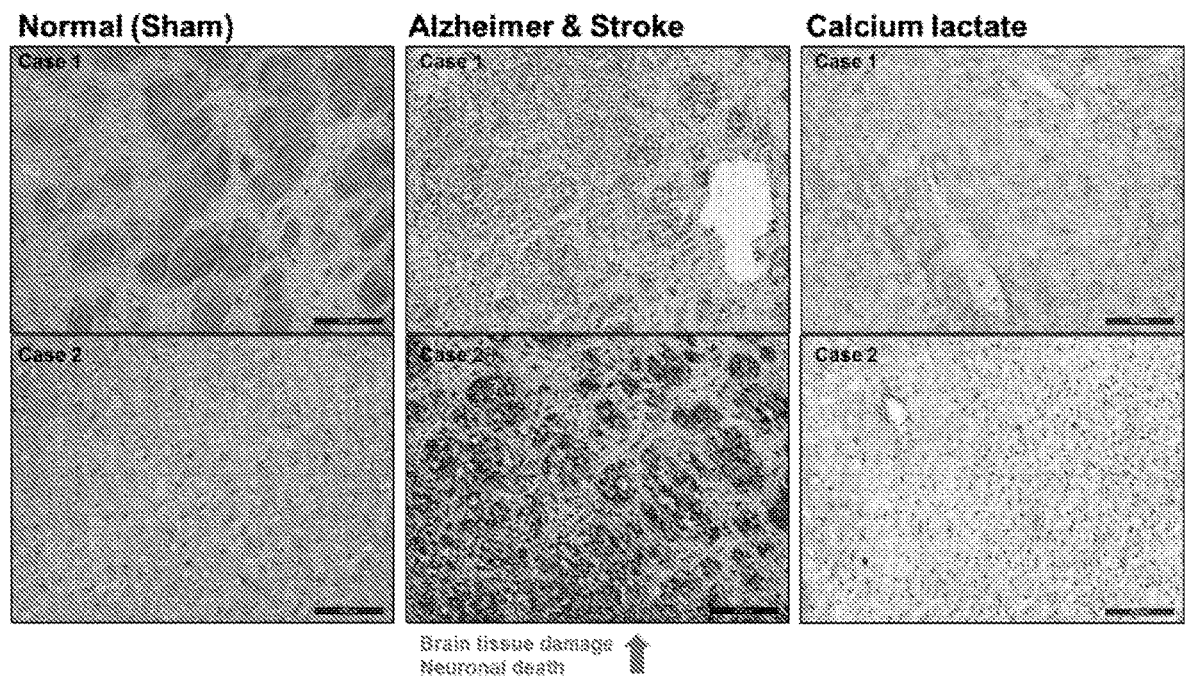
FIG. 31. Recovery of damaged brain tissue and reduction of microglia infiltration that recruited upon brain damage.

FIG. 31 shows the recovery of damaged brain tissue and the reduction of microglia infiltration that recruited upon brain damage. The results show that the inflammatory reaction, which exacerbates Alzheimer's and stroke, is greatly reduced.

Example 22. Targeting Parkinson's Disease

Materials and Methods

Animals. All experiments were carried out in accordance with animal care guidelines under Korean law (11737, rev'd Apr. 5, 2013) and the guidelines set by the Institutional Animal Care and Use Committee at Gachon university (LCDI-2018-0073). Eight-week old male Sprague-Dawley (SD) rats were obtained from Samtako Co. (Osan, Gyeonggi-do, Republic of Korea) and bred under specific-pathogen-free (SPF) conditions. All animals were maintained in a 12-hour light/dark cycle at 22-25° C. with free access to food and water.

Preparation of desipramine, 6-OHDA, and calcium lactate. Desipramine (12.5 mg/kg; noradrenaline transporter blocker; Sigma Aldrich, St. Louis, USA) was dissolved in saline for intraperitoneal injection. 6-OHDA (20 µg/rat, Sigma Aldrich, St. Louis, USA) was dissolved in saline for intracranial injection. 2 mg/kg of calcium lactate (Sigma Aldrich, St. Louis, USA) was dissolved in saline for daily subcutaneous injection (21 days).

Injection of desipramine and 6-OHDA. The animals were injected with desipramine into the abdominal cavity (intraperitoneal injection) 30 min before 6-OHDA injection. 30 min after Desipramine injection, the animals were placed in a small acrylic cage that was coupled with an anesthesia machine that allowed them to breathe freely under gaseous anesthesia (2% isoflurane, Spartanburg, SC, USA). After full anesthesia of an animal was achieved, it was positioned on an operating table (while maintaining the gaseous anesthesia) with the superior aspect of the neck hyperextended to expose the posterior region. The animal fur of head was shaved with an electric clipper, and the skin was swabbed with iodine. All the surgical materials disinfected with 70% ethanol. Hamilton syringe barrel inner space was cleaned with distilled water and 70% ethanol. The Hamilton syringe was placed in the syringe holder. The animal in the stereotaxic apparatus was placed on horizontal position. A midline incision (about 1 cm) on the skin of head was made with the scalpel. The needle of Hamilton syringe was placed on the bregma. The three coordinates (AP: −5.6, LM: 2.0, and DV: −7.6) on the manipulator (in mm) were read and used as the starting point. The DV coordinate of the injection point was set slowly; this inserts the needle tip into the brain until the injection point. The 6-OHDA solution (20 µg/4 µl) was released at an approximate flow rate of 1 µl/min. After the injection, the needle was removed very slowly. The wound area was closed by suturing, and then disinfectant was applied. The rat was marked for further identification.

Immunohistochemistry. Brain tissue was sectioned at 5 µm on cryostat and stained for histological examination. Microscopic images were obtained at 200× magnification. For immunohistochemistry, sections were blocked with 1% BSA and 10% NGS in 0.05 M PBS for 1 h at room temperature and then reacted with rabbit anti-tyrosine hydroxylase (1:500, Chemicon, Tokyo, Japan) at 4° C. two overnights. ABC staining system was used to visualize dopaminergic neuron in the sections (Vector Laboratories, CA, USA).

Results

Figure 32:
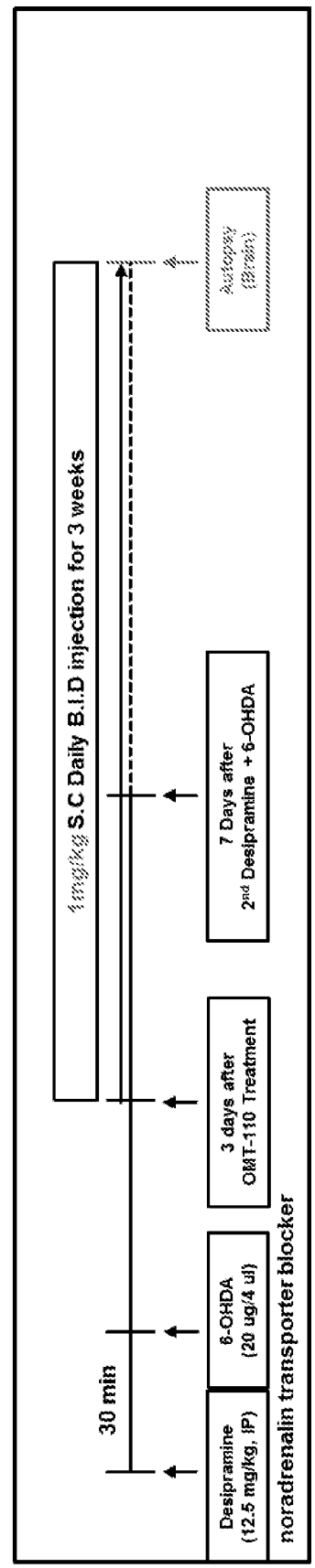
FIG. 32. Experimental scheme for establishing Parkinson's disease.

FIG. 32 provides an experimental scheme for establishing Parkinson's disease. OMT-110 is calcium lactate.

Figure 33:
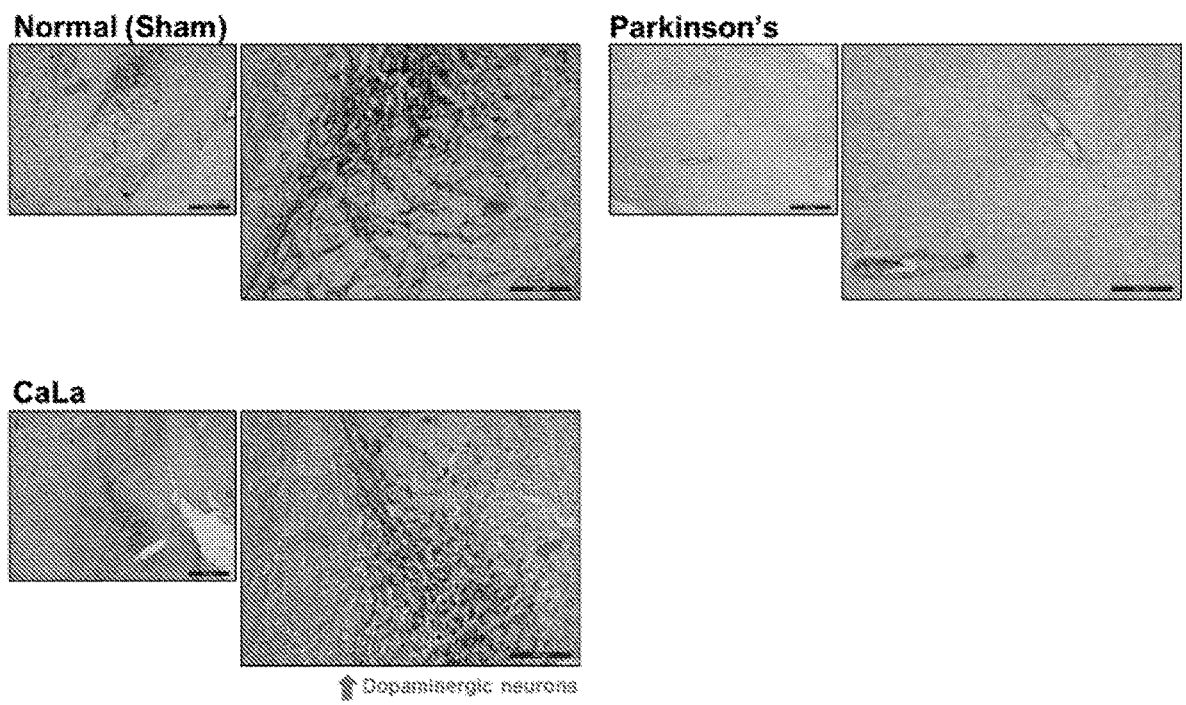
FIG. 33. Recovery of dopaminergic neuron by treatment with calcium lactate.

FIG. 33 shows the recovery of dopaminergic neuron by treatment with calcium lactate. Parkinson's disease is a neurodegenerative disorder that affects dopamine-producing by disrupting dopaminergic neurons in a specific area of the brain (substantia nigra).

Example 23. Targeting Multiple Sclerosis and Spinal Cord Injury

Materials and Methods

Animals. All experiments were carried out in accordance with animal care guidelines under Korean law (11737, rev'd Apr. 5, 2013) and the guidelines set by the Institutional Animal Care and Use Committee at Gachon university (LCDI-2018-0073). Eight-week old male Sprague-Dawley (SD) rats were obtained from Samtako Co. (Osan, Gyeonggi-do, Republic of Korea) and bred under specific-pathogen-free (SPF) conditions. All animals were maintained in a 12-hour light/dark cycle at 22-25° C. with free access to food and water.

Preparation of Lipopolysaccharides (LPS) and Calcium Lactate. Dissolve 1 mg of LPS powder in 1 ml of saline. Keep the tubes on ice if LPS is going to be used fresh. For long storage, use screw cap vials are preferred. The aliquots were stored at deep freezer (−20° C.). Calcium lactate was purchased from Sigma Aldrich (St. Louis, USA). Two mg/kg of calcium lactate was dissolved in saline for daily subcutaneous injection (21 days).

Intraspinal injection of LPS. The animals were placed in a small acrylic cage that was coupled with an anesthesia machine that allowed them to breathe freely under gaseous anesthesia (2% isoflurane, Spartanburg, SC, USA). After full anesthesia of an animal was achieved, it was positioned on an operating table (while maintaining the gaseous anesthesia). For intraspinal injection of LPS, the laminectomy site of rats was exposed. Two small holes, 1 mm apart, were made in the dura over the left dorsal column. A volume of 1 µl of LPS solution was carefully drawn up into a sterile Hamilton syringe, and the LPS solution was slowly injected into the spinal cord. The syringe maintained in place for an additional 2 min to prevent back-flux from the injection site. Then, the injection site was closed by surgical clips.

Immunohistochemistry. Spinal cord tissue was sectioned at 5 µm on cryostat and stained for histological examination. Microscopic images were obtained at 200× magnification. For immunohistochemistry, sections were blocked with 1% BSA and 10% NGS in 0.05 M PBS for 1 h at room temperature and then reacted with rabbit anti-Iba-1 (1:1000, Bioss, MA, USA) at 4° C. two overnights. ABC staining system was used to visualize microglia (Iba-1) in the sections (Vector Laboratories, CA, USA).

Results

Figure 34:
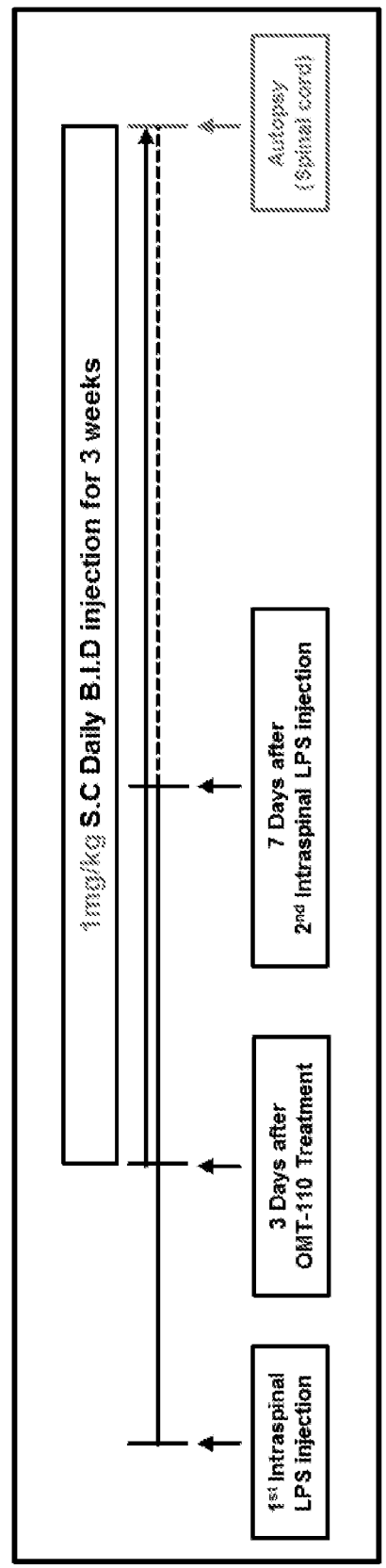
FIG. 34. Experimental scheme for establishing multiple sclerosis.

FIG. 34 provides an experimental scheme for establishing multiple sclerosis. OMT-110 is calcium lactate.

Figure 35:
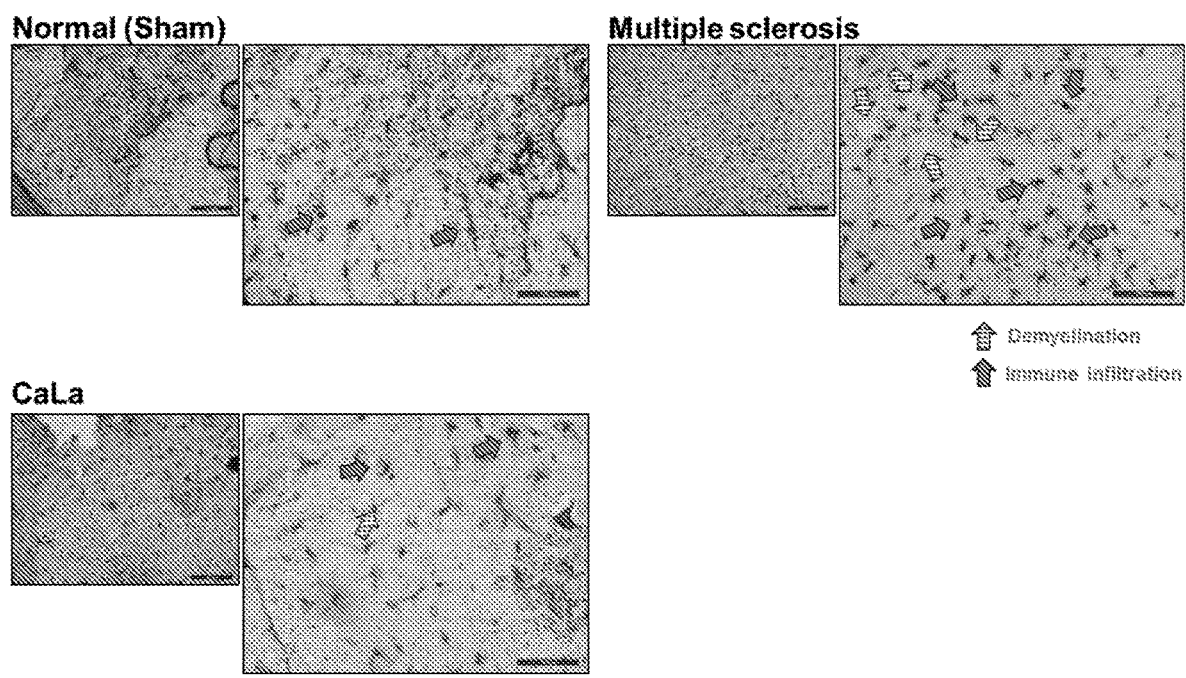
FIG. 35. Recovery of demyelinated spinal cord and reduction of microglia infiltration by treatment with calcium lactate.

FIG. 35 shows the recovery of demyelinate spinal cord and the reduction of microglia infiltration by treatment with calcium lactate. Demyelination of central nervous system and immune infiltration occur in association with inflammation in a number of disorders, including multiple sclerosis and spinal cord injury.

Example 24. Targeting Vascular Disease (Atherosclerosis, Cerebral Hemorrhage, and Myocardial Infarction)

Materials and Methods

Animals. All experiments were carried out in accordance with animal care guidelines under Korean law (11737, rev'd Apr. 5, 2013) and the guidelines set by the Institutional Animal Care and Use Committee at Gyeonggi bio center (2017-11-0008, South Korea). Fibe-week old male BALB/c ApoE$^{shi}$ mice were obtained from Japan SLC Inc. (Shizuoka, Japan) and bred under specific-pathogen-free (SPF) conditions. All animals were maintained in a 12-hour light/dark cycle at 22-25° C. with free access to food and water.

Preparation of Calcium Lactate. Calcium lactate was purchased from Sigma Aldrich (St. Louis, MO, USA). Two mg/kg of calcium lactate was dissolved in saline for daily subcutaneous injection (21 days).

Animal model for vascular disease. BALB/c ApoE$^{shi}$ species is used for spontaneous induction of vascular disease. In this investigation, a high fat (40%) diet was provided for 4 weeks to induce strong atherosclerosis.

Histological analysis. The thoracic aorta was transected, and a half of the aorta was fixed in 10% neutral buffer formalin fixative solution. Then, histological analysis was performed.

Histological analysis was performed with H&E and Oil red O staining. Aortic wall thickness, atherosclerotic plaque areas, foam cell numbers, and lipidated regions were analyzed.

Statistical analysis. Statistical analysis was performed using SPSS statistics, and the results were analyzed using Student t-test. Histologic analysis was performed using the Mann-Whitney method. P<0.05 was considered statistically significant.

Results

TABLE 1

Quantitative analysis for histological analysis. All clinical indicators of arteriosclerosis were significantly increased after disease induction. However, the indicators were significantly decreased after treatment with calcium lactate.

| | HISTOPATHOLOGICAL ANALYSIS | | | |
|---|---|---|---|---|
| Group | MEAN AORTA WALL THICKNESS (μm) | ATHEROSCLEROTIC PLAQUE AREAS (mm$^2$) | FOAM CELL NUMBERS (cells/mm$^2$) | MALE LIPID DEPOSITED REGIONS (mm$^2$) |
| G1 | 47.71 ± 2.43 | 0.00 ± 0.00 | 0.00 ± 0.00 | 0.01 ± 0.00 |
| G2 | 147.51 ± 23.58* | 0.50 ± 0.08* | 135.75 ± 31.76* | 0.41 ± 0.06* |
| G3 | 85.83 ± 8.70+ | 0.10 ± 0.03++ | 39.00 ± 10.13+ | 0.09 ± 0.03++ |

*significantly different between G2 and G1, P < 0.05;
++significantly different between G2 and G3, P < 0.01;
+significantly different between G2 and G3, P < 0.05.
Data were expressed as mean ± S.E.M. The results were statistically analyzed by Mann-Whitney methods.
G1: Normal control (Saline);
G2: Vehicle control (Saline);
G3: Calcium lactate;
G2-G3: High cholesterol diet supplied ApoE-deficient mice (Atherosclerosis)

Evidence for direct targeting on Atherosclerosis

TABLE 2

| | Clinical blood chemistry | | | |
|---|---|---|---|---|
| | CLINICAL BLOOD BIOCHEMISTRY (mg/dL) | | | MALE |
| GROUP | TCHO | TG | LDL | HDL |
| G1 | 113.73 ± 3.0 | 75.73 ± 1.5 | 15.0 ± 2.9 | 87.34 ± 13.0 |
| G2 | 2092.4 ± 349.2** | 48.6 ± 6.8* | 1541.6 ± 30.9** | 220.4 ± 11.7** |
| G3 | 2328.0 ± 56.7 | 54.8 ± 2.8 | 1537.1 ± 14.2 | 197.2 ± 3.7 |

Data were expressed as mean ± S.E.M. statistically analyzed by student t-test methods.
**statistically different between G2 and G1, P < 0.01
*statistically different between G2 and G1, P < 0.05
G1: Normal control (Saline, n = 3)
G2: Vehicle control (Saline, n = 8)
G3: Test article (Calcium lactate pentahydrate, n = 8)
G2-G3: High cholesterol diet supplied ApoE-deficient mice Pathogenic factors such as cholesterol (TCHO), LDL cholesterol (LDL), triglycerides (TG), and HDL-cholesterol (HDL) were not controlled by calcium lactate. The combined form of calcium with lactate acts as a single ingredient directly on the disease site (see FIG. 36).

Figure 36:
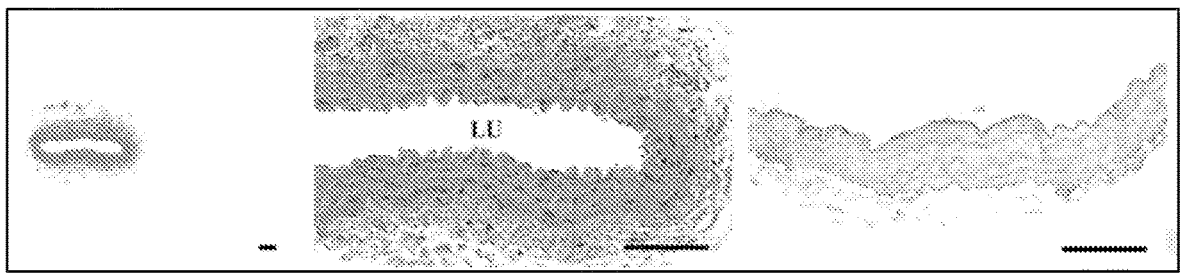
FIG. 36. Representative histological profiles of aorta tissues. The tissues in left and middle side are hematoxylin and eosin (H&E) staining. The tissues in right side are oil red o staining.
Figure 36:
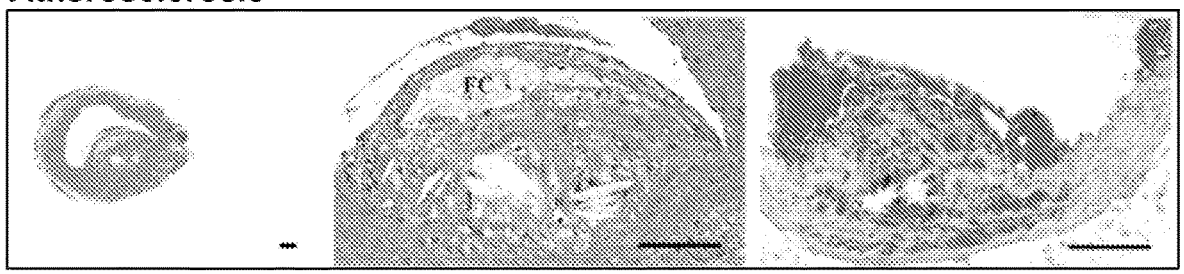
Figure 36:
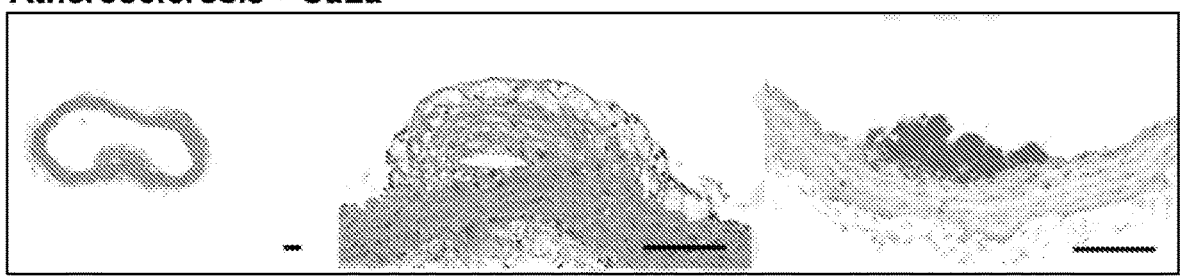

FIG. 36 provides representative histological profiles of the aorta tissues. The tissues in left and middle side of pictures are a H&E staining. The tissues in right side of pictures are an oil red staining for distinguishing the atherosclerotic lesions. The atherosclerotic lesions were decreased by treatment with calcium lactate.

Example 25. Targeting Periodontal Disease (Pulpitis and Periodontitis)

Materials and Methods

Animals. All experiments were carried out in accordance with animal care guidelines under Korean law (11737, revised Apr. 5, 2013) and the guidelines set by the Institutional Animal Care and Use Committee at Gachon university (LCDI-2018-0073). Eight-week old male Sprague-Dawley (SD) rats were obtained from Samtako Co. (Osan, Gyeonggi-do, Republic of Korea) and bred under specific-pathogen-free (SPF) conditions. All animals were maintained in a 12-hour light/dark cycle at 22-25° C. with free access to food and water.

Preparation of Lipopolysaccharides (LPS) and Calcium Lactate. Dissolve 1 mg of LPS powder in 100 μl of saline. Keep the tubes on ice if LPS is going to be used fresh. For long storage, use screw cap vials are preferred. The aliquots were stored in a deep freezer (−20° C.). Calcium lactate was purchased from Sigma Aldrich (St. Louis, MO, USA). Two mg/kg of calcium lactate was dissolved in saline for daily subcutaneous injection (21 days).

Animal model for periodontal disease. Periodontal disease was induced by intragingival injection of LPS (1 mg/100 μl) in sterile saline. A fine hypodermic needle was inserted at the mesiolateral aspect of the first right mandibular molar and the tip moved distally so that the injection was made at the interdental papilla between the first and second molars. The injection was slowly made, and the needle held in place for 10 seconds post injection to ensure that the LPS was not lost through the needle track.

Figure 37:
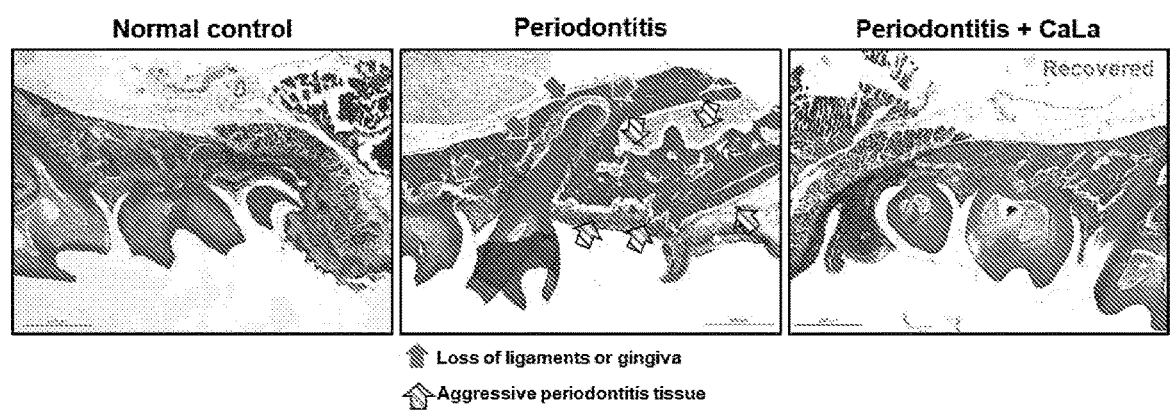
FIG. 37. Masson's trichrome staining for periodontal tissues.

Histological analysis. Rat gingiva including tooth were dissected and fixed in 4% paraformaldehyde for 2 days at 4° C. Fixed tissues were embedded in paraffin and sectioned at 10 μm. Slides were incubated at 55° C. for 2 h, and subsequently deparaffinized in xylene and rehydrated in a graded ethanol series and re-fix in Bouin's solution for 1 h, remove the yellow color to rinse running tap water for 5-10 min and stained with Biebrich scarlet-acid fuchsin solution for 5 min than in phosphomolybdic-phosphotungstic acid solution (ratio 1:1) for 30 min, and aniline blue solution for 15 min. Rinse briefly in distilled water and in 1% acetic acid solution for 5 min. Dehydrate 95% ethyl alcohol, absolute ethyl alcohol and clear in xylene. Mount with mounting medium. The stained tissues were Imaged using a Leica DM 1000 LED microscope (Leica Microsystems, Wetzlar, Germany).
Results FIG. 37 shows Masson's trichrome staining for periodontal tissues. LPS treatment induces periodontal disease, which causes loss of ligaments and gingiva around the root of tooth (middle image). The ligaments and gingiva were recovered after treatment with calcium lactate (right image), same with the normal control (left image).

Figure 38:
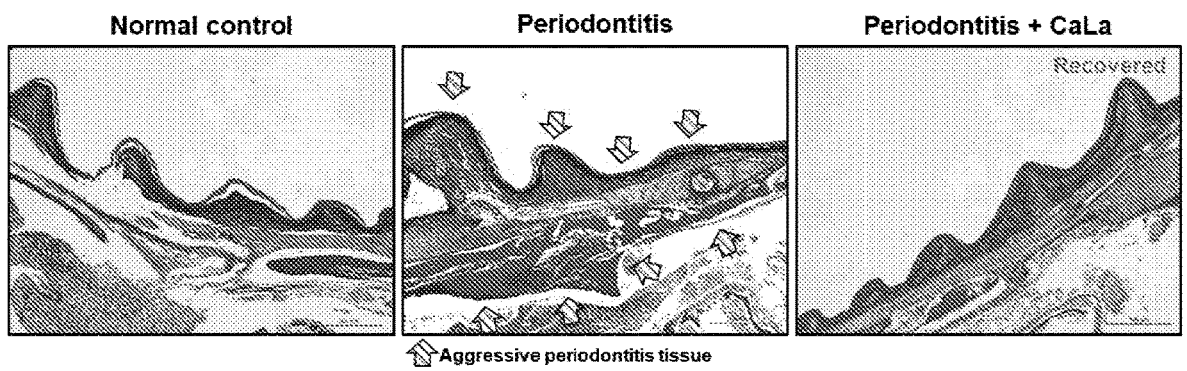
FIG. 38. Masson's trichrome staining for upper gum.

FIG. 38 shows Masson's trichrome staining for the upper gum. The upper gum around the periodontal tissue that was treated with LPS shows abnormal morphology by severe inflammation (middle image). The morphology of the upper gum was recovered after treatment with calcium lactate (right image), same with the normal control (left image).

Example 26. Targeting Musculoskeletal Disease (Rheumatoid Arthritis)

Materials and Methods

Animals. All experiments were carried out in accordance with animal care guidelines under Korean law (11737, rev'd Apr. 5, 2013) and the guidelines set by the Institutional Animal Care and Use Committee at Gyeonggi bio center (2017-11-0003, South Korea). Six-week old male DBA1/J mice were obtained from Japan SLC Inc. (Shizuoka, Japan) and bred under specific-pathogen-free (SPF) conditions. All animals were maintained in a 12-hour light/dark cycle at 22-25° C. with free access to food and water.

Preparation of agents. Two mg/mL Type II collagen was mixed with the same volume of complete Freund's adjuvant (CFA) for primary induction of rheumatoid arthritis. Two mg/mL Type II collagen was mixed with the same volume of incomplete Freund's adjuvant (IFA) for secondary induction of rheumatoid arthritis. Two mg/kg of calcium lactate was dissolved in saline for daily subcutaneous injection (21 days).
Animal Model for Rheumatoid Arthritis Primary induction: 0.1 mL of the mixed solution (Type II collagen+CFA) was injected subcutaneously into the area of 1.5 cm from the base of tail of mice. The administration site and depth were the same in all mice.

Secondary induction: 21 days after primary induction, 0.1 mL of the mixed solution (Type II collagen+IFA) was injected subcutaneously into the area of 1.5 cm from the base of tail of mice. The administration site and depth were the same in all mice.

Figure 39:
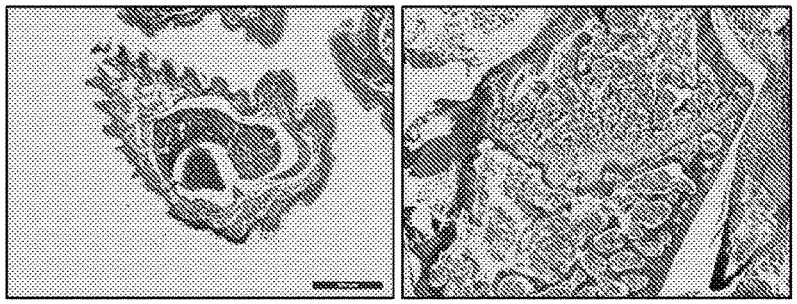
FIG. 39. Masson's trichrome staining for foot and knee joint tissues.
Figure 39:
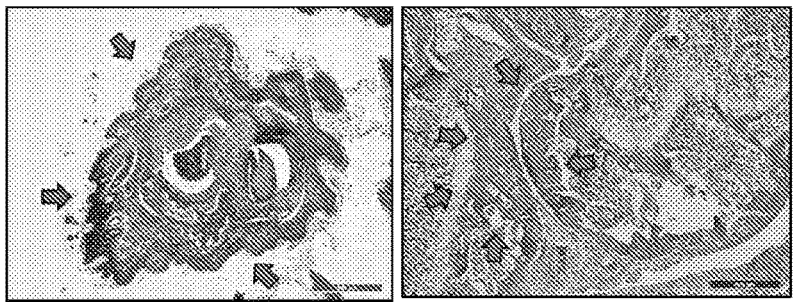
Figure 39:
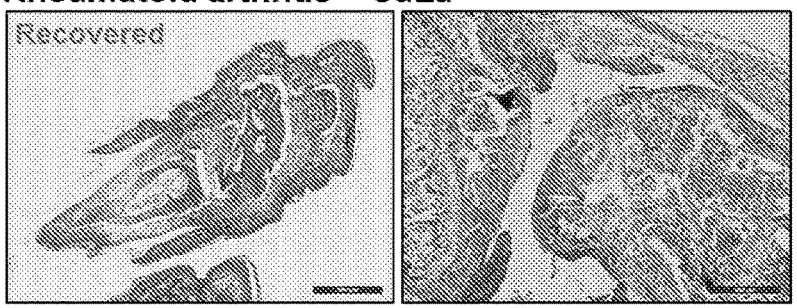

Histological analysis. The mice foot and knee joint were dissected and fixed (4% paraformaldehyde) and decalcified for 2 days at 4° C. The tissues were embedded in paraffin and sectioned at 15 μm. Slides were incubated at 55° C. for 2 h, and subsequently deparaffinized in xylene and rehydrated in a graded ethanol series and stained with Biebrich scarlet-acid fuchsin solution for 5 min than in phosphomolybdic-phosphotungstic acid solution (ratio 1:1) for 30 min, and aniline blue solution for 15 min. Rinse briefly in distilled water and in 1% acetic acid solution for 5 min. Dehydrate 95% ethyl alcohol, absolute ethyl alcohol and clear in xylene. Mount with mounting medium. The stained tissues were Imaged using a Leica DM 1000 LED microscope (Leica Microsystems, Wetzlar, Germany).
Results FIG. 39 shows Masson's trichrome staining for foot and knee joint tissues. Inflammatory edema was observed in the toes and knee joint by rheumatoid arthritis (middle images). 21 days after treatment with CaLa, the inflammatory edema clearly decreased in the toes and knee joint (lower images), and it was morphologically recovered same with the normal control (upper images).

Example 27. Targeting Digestive Disease (Inflammatory Bowel Disease: Crohn's and Colitis)

Materials and Methods

Animals. All experiments were carried out in accordance with animal care guidelines under Korean law (11737, rev'd Apr. 5, 2013) and the guidelines set by the Institutional Animal Care and Use Committee at Gachon university (LCDI-2018-0073). Six-week old male Sprague-Dawley (SD) rats were obtained from Samtako Co. (Osan, Gyeonggi-do, Republic of Korea) and bred under specific-pathogen-free (SPF) conditions. All animals were maintained in a 12-hour light/dark cycle at 22-25° C. with free access to food and water.

Figure 40:
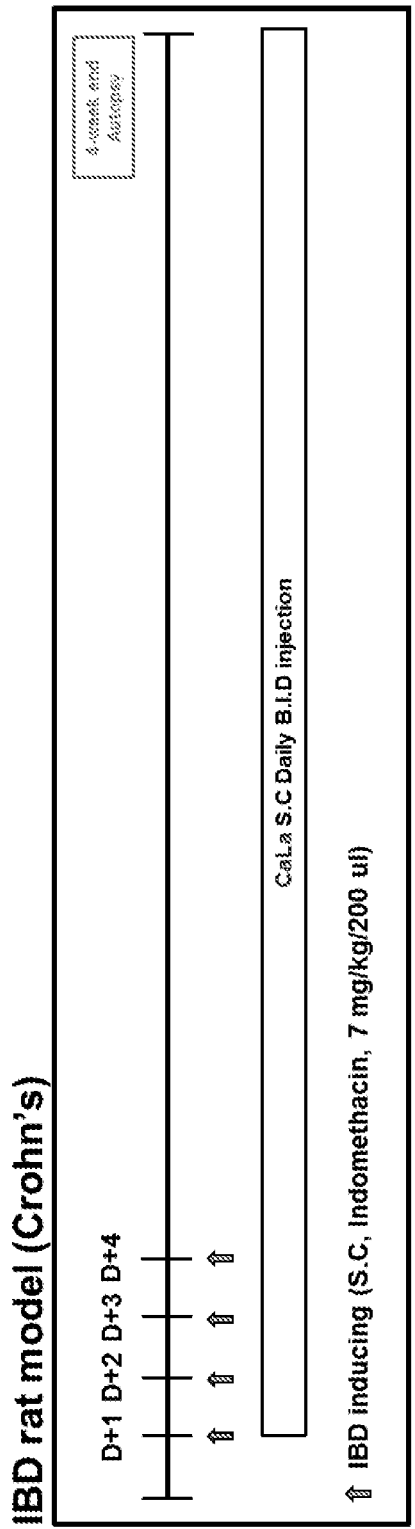
FIG. 40. Experimental scheme for inducing Crohn's disease.

Agents and animal model. To induce Crohn's disease and colitis, Indomethacin was purchased from Sigma Chemical (St. Louis, Missouri, USA) and was dissolved in saline. Two mg/kg of calcium lactate was dissolved in saline for daily subcutaneous injection (21 days). Two models of inflammatory bowel disease were used. Crohn's disease was induced by oral administration of Indomethacin (7 mg/kg), and colitis was induced by subcutaneous injections of Indomethacin (7 mg/kg) daily at a 24 h intervals (FIGS. 40 and 42).

Histological analysis. The fixed flat-mounts were dehydrated in a graded series of ethanol and embedded in paraffin. Paraffin sections (5 μm thick) were stained with hematoxylin (Merck, Darmstadt, Germany) and eosin (Sigma-Aldrich, St Louis, MO, USA) (H&E) and were imaged using a Leica DM 1000 LED microscope (Leica Microsystems, Wetzlar, Germany).
Results FIG. 40 provides an experimental scheme for inducing Crohn's disease.

Figure 41:
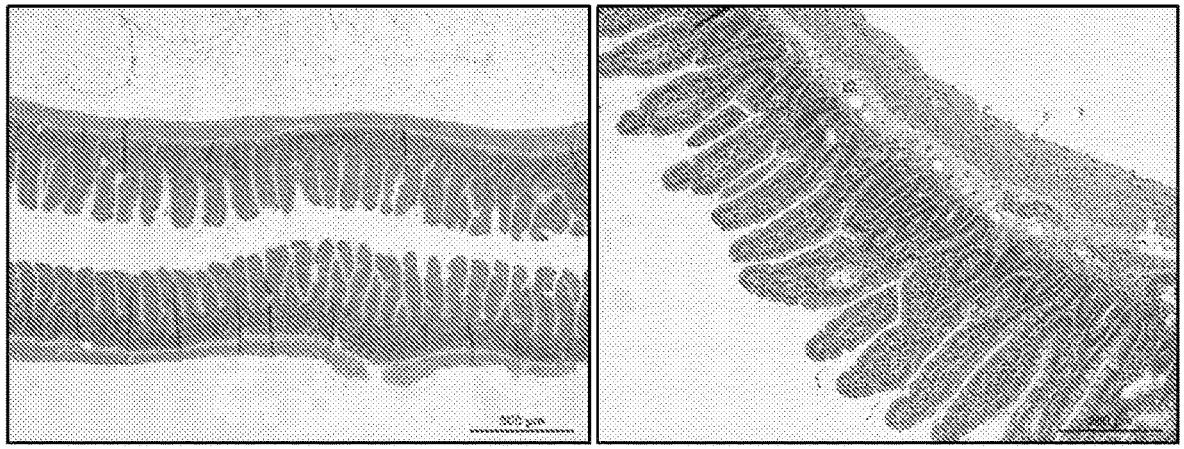
FIG. 41. Representative images for hematoxylin and eosin (H&E) staining of Crohn's disease.
Figure 41:
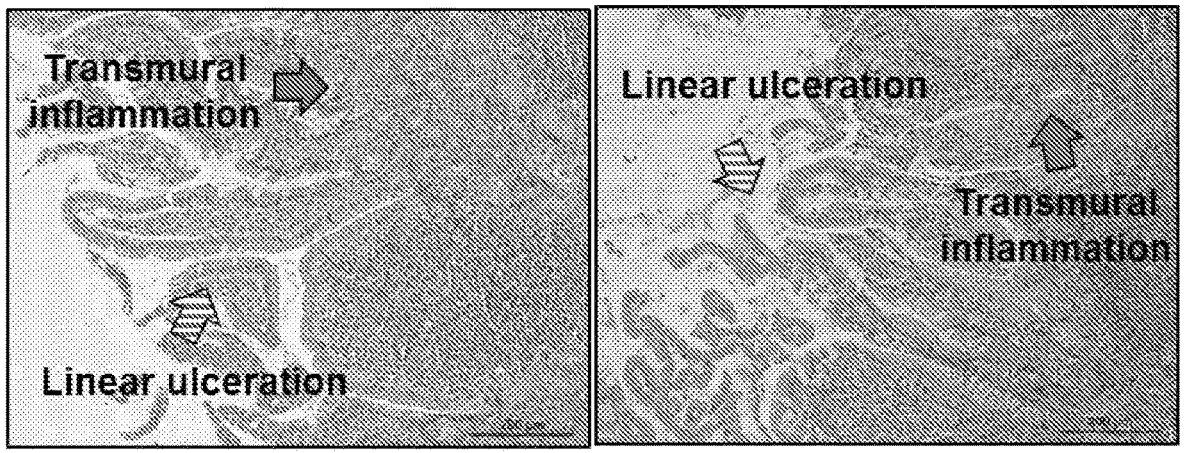
Figure 41:
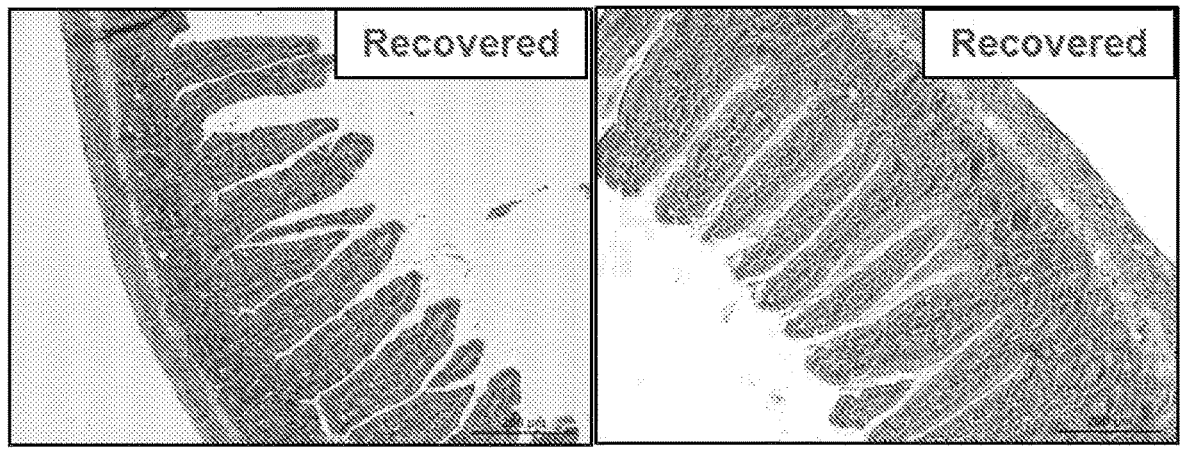

FIG. 41 provides representative images for H&E staining of Crohn's disease. Transmural inflammation and linear ulceration in intestine were observed after induction of Crohn's disease (middle image). Four-week after treatment with CaLa, the transmural inflammation and linear ulceration were clearly decreased in the intestinal tissues (lower images), and it was morphologically recovered same with the normal control (upper images).

Figure 42:
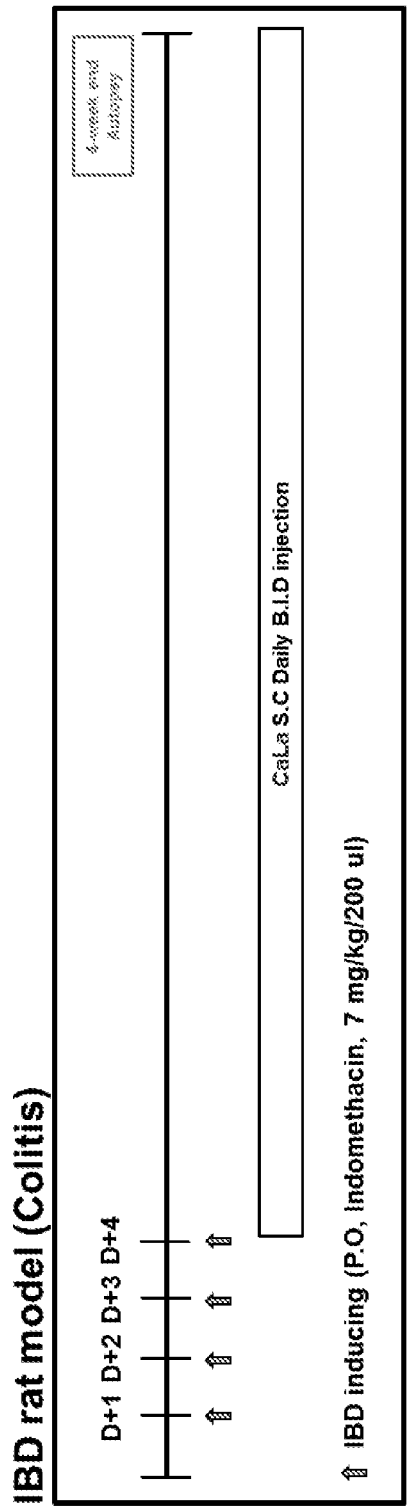
FIG. 42. Experimental scheme for inducing colitis.

FIG. 42 provides an experimental scheme for inducing colitis.

Figure 43:
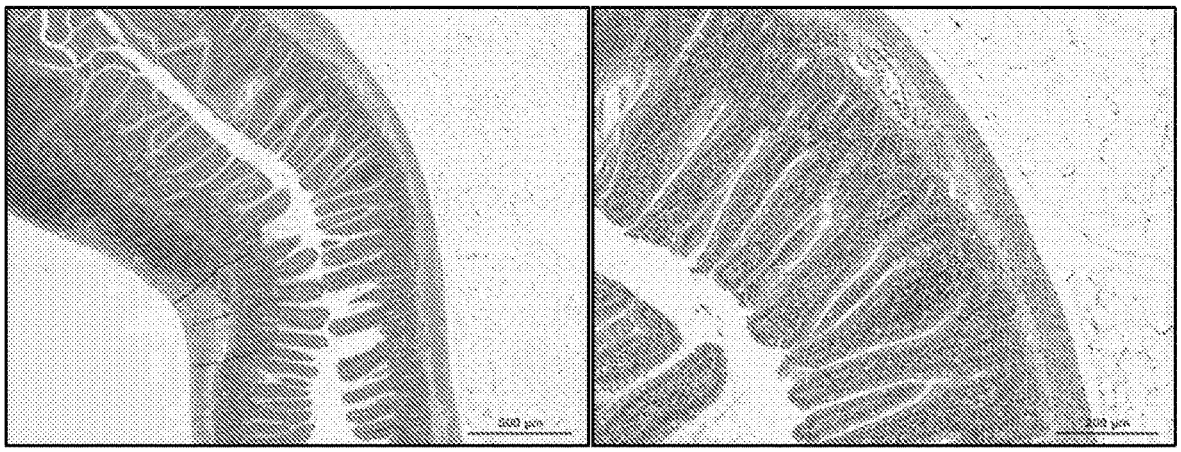
FIG. 43. Representative images for hematoxylin and eosin (H&E) staining of colitis.
Figure 43:
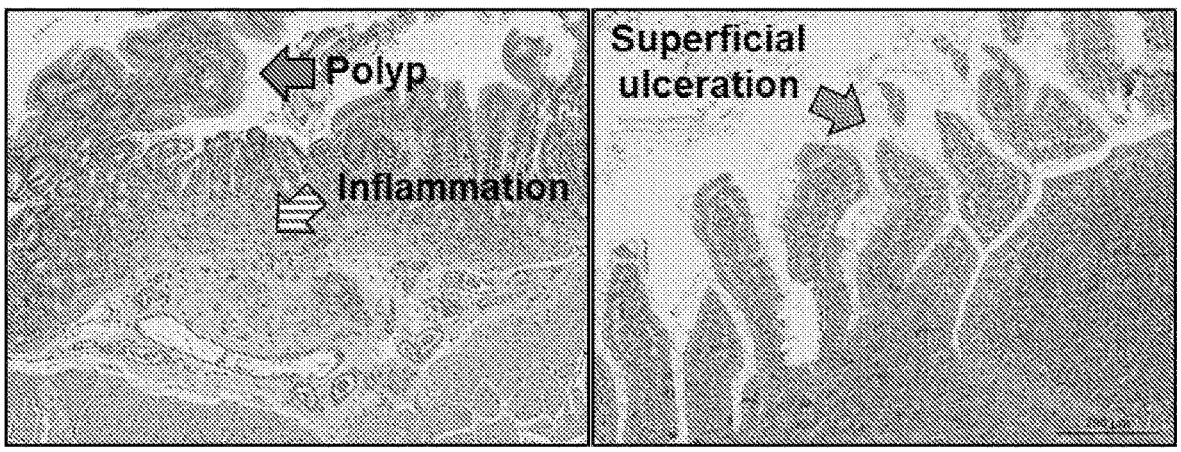
Figure 43:
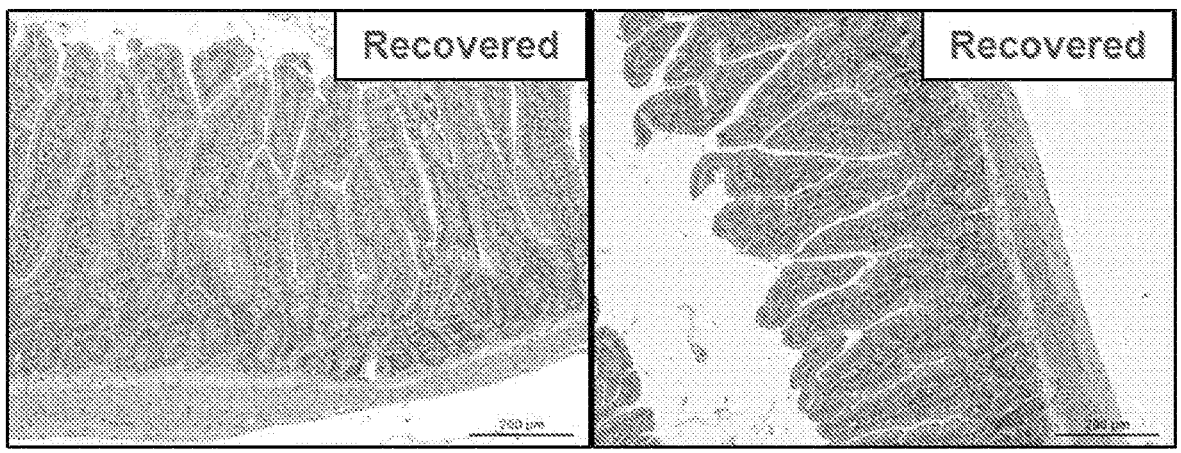

FIG. 43 provides representative images for H&E staining of colitis. Superficial ulceration, polyp, and inflammation in intestine were observed after induction of colitis (middle image). Four-week after treatment with CaLa, the Superficial ulceration, polyp, and inflammation were clearly decreased in the intestinal tissues (lower images), and it was morphologically recovered same with the normal control (upper images).

Some additional embodiments disclosed herein include but are not limited to the following:

A. A method of treating asthma, pulmonary fibrosis, obesity, gastroenteritis, chronic inflammatory bowel disease, and/or atopic dermatitis, the method comprising administering to a subject in need thereof a therapeutically effective amount of calcium lactate.

B. A method of treating chronic obstructive pulmonary disease, pneumonitis, keratitis, atherosclerosis, arteriosclerosis, myocarditis, diabetes, rheumatoid arthritis, pulpitis, periodontitis, and/or psoriasis, the method comprising administering to a subject in need thereof a therapeutically effective amount of calcium lactate.

C. A method of treating Alzheimer's disease, stroke, Parkinson's disease, multiple sclerosis, age-related macular degeneration, non-alcoholic fatty liver disease, sepsis, and/or osteoporosis, the method comprising administering to a subject in need thereof a therapeutically effective amount of calcium lactate.

D. The method of any one of embodiments A-C, wherein the calcium lactate is administered in a pharmaceutical composition comprising a pharmaceutically acceptable carrier, excipient, or diluent.

E. The method of any one of embodiments A-D, wherein the pharmaceutical composition is formulated into liquid, powder, aerosol, injection, fluid transfusion, patch, capsule, pill, tablet, depot, or suppository.

F. The method of any one of embodiments A-D, wherein the pharmaceutical composition comprises a therapeutically effective amount of calcium lactate as an active agent and a pharmaceutically acceptable polysaccharide, polymer, lipid, or combinations thereof.

G. The method of embodiment F, wherein the pharmaceutical composition comprises the calcium lactate and the polysaccharide.

H. The method of embodiment G, wherein a weight ratio of the calcium lactate to the polysaccharide is 1:<0.2 to 1:5.

I. The method of embodiment G, wherein a weight ratio of the calcium lactate to the polysaccharide is 1:<0.2.

J. The method of embodiment G, wherein a weight ratio of the calcium lactate to the polysaccharide is 1:0.2 to 1:5.

K. The method of any one of embodiment F-J, further comprising a polymer and/or lipid.

L. The method of embodiment K, further comprising the polymer and lipid, wherein the weight ratio of the polymer to the lipid is 1:0.1 to 1:50.

M. The method of any one of embodiments K-L, wherein the weight ratio of the calcium lactate to the polymer and/or lipid is at least 1:5.

N. The method of embodiment M, wherein a weight ratio of the calcium lactate to the polymer and/or lipid is 1:5 to 1:30.

O. The method of embodiment F, comprising the calcium lactate and the polymer and/or lipid.

P. The method of embodiment 0, comprising the polymer and lipid, wherein the weight ratio of the polymer to the lipid is 1:0.1 to 1:50.

Q. The method of any one of embodiments O-P, wherein a weight ratio of the calcium lactate to the polymer and/or lipid is at least 1:5.

R. The method of any one of embodiments O-Q, wherein the weight ratio of the calcium lactate to the polymer and/or lipid is 1:5 to 1:30.

S. The method of any one of embodiments O-R, wherein the composition is short-acting.

T. The method of any one of embodiments O-R, wherein the composition is long-acting.

U. The method of any one of embodiments F-T, wherein the composition is an injectable composition.

V. The method of any one of embodiments F-U, comprising the polysaccharide that is a cellulose derivative, pectin, hyaluronic acid, starch, guar gum, chitosan, gelatin, collagen, alginate, alginic acid or combinations thereof.

W. The method of any one of embodiments F-V, comprising the polymer that is a poloxamer, polyvinylpyrrolidone, polyethylene glycol (PEG), polyglycolic lactic acid (PLGA), or combinations thereof.

X. The method of any one of embodiments F-W, comprising the lipid that is a mono- or tri-fatty acid glycerin ester or polyethylene glycol, polyethylene glycol esters of vegetable oils, fatty acid propylene glycol esters, sesame oil, soybean oil, castor oil, corn oil, palm oil, peanut oil, cacao oil, cottonseed oil, sunflower seed oil, safflower oil, almond oil, olive oil, hydrogenated oil, oleic acid, linolenic acid, linoleic acid, palmitic acid, palmitoleic acid, arachadonic acid, myristic acid, capric acid, caprylic acid, lauric acid, stearic acid, ethyl oleate, isopropyl palmitate, octyldodecyl myristate, cetyl palmitate, lauryl alcohol, oleyl alcohol, cetyl alcohol, stearyl alcohol, or combinations thereof.

Y. The method of any one of embodiments F-S and U-X, wherein upon placement of the composition in an in vitro dissolution test comprising an elution test method at 300 rpm in 200 ml aqueous medium having a pH of 6.8 at 37° C. using a nylon filter having a pore size of 45 μm, at least about 40% of the active agent is released after 6 hours.

Z. The method of any one of embodiments F-S and U-Y, wherein upon placement of the composition in an in vitro dissolution test comprising an elution test method at 300 rpm in 200 ml aqueous medium having a pH of 6.8 at 37° C. using a nylon filter having a pore size of 45 μm, at least about 60% of the active agent is released after 12 hours.

AA. The method of any one of embodiments F-S and U-Z, wherein upon placement of the composition in an in vitro dissolution test comprising an elution test method at 300 rpm in 200 ml aqueous medium having a pH of 6.8 at 37° C. using a nylon filter having a pore size of 45 μm, at least about 80% of the active agent is released after 24 hours.

BB. The method of any one of embodiments F-S and U-AA, wherein upon placement of the composition in an in vitro dissolution test comprising an elution test method at 300 rpm in 200 ml aqueous medium having a pH of 6.8 at 37° C. using a nylon filter having a pore size of 45 inn, at least about 90% of the active agent is released after 48 hours.

CC. The method of any one of embodiments F-H, J-R, and T-X, wherein upon placement of the composition in an in vitro dissolution test comprising an elution test method at 300 rpm in 200 ml aqueous medium having a pH of 6.8 at 37° C. using a nylon filter having a pore size of 45 inn, less than about 40% of the active agent is released after 24 hours.

DD. The method of any one of embodiments F-H, J-R, and T-CC, wherein upon placement of the composition in an in vitro dissolution test comprising an elution test method at 300 rpm in 200 ml aqueous medium having a pH of 6.8 at 37° C. using a nylon filter having a pore size of 45 inn, less than about 60% of the active agent is released after 48 hours.

EE. The method of any one of embodiments F-H, J-R, and CC-DD, wherein upon placement of the composition in an in vitro dissolution test comprising an elution test method at 300 rpm in 200 ml aqueous medium having a pH of 6.8 at 37° C. using a nylon filter having a pore size of 45 µm, less than about 80% of the active agent is released after 72 hours.

FF. The method of any one of embodiments F-H, J-R, and CC-EE, wherein upon placement of the composition in an in vitro dissolution test comprising an elution test method at 300 rpm in 200 ml aqueous medium having a pH of 6.8 at 37° C. using a nylon filter having a pore size of 45 inn, less than about 90% of the active agent is released after 144 hours.

GG. The method of any one of embodiments F-FF, wherein the composition is contained in a sterile glass or polyolefin container.

HH. The method of any one of embodiments A-D, wherein the calcium lactate is coated with a pharmaceutically acceptable enteric coating.

II. The method of embodiment HH, wherein the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof.

JJ. The method of any one of embodiments HH-II, wherein the weight ratio of the calcium lactate to the enteric coating is 10:0.5 to 1:1.5.

KK. The method of any one of embodiments HH-JJ, wherein in an in vitro dissolution test comprising a USP Paddle method at a paddle speed of 50 rpm at 37° C., when the composition is placed in 0.1 HCl for 120 minutes followed by adjusting to pH 6.8 with phosphate buffer, less than about 20% of the active agent is released after 30 minutes.

LL. The method of any one of embodiments HH-KK, wherein in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 30% of the active agent is released after 60 minutes.

MM. The method of any one of embodiments HH-LL, wherein in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 50% of the active agent is released after 120 minutes.

NN. The method of any one of embodiments HH-MM, wherein in an in vitro dissolution test comprising a USP Paddle method at a paddle speed of 50 rpm at 37° C., when the composition is placed in 0.1 N HCl for 120 minutes followed by adjusting to pH 6.8 with phosphate buffer, less than 10% of the active agent is released after 120 minutes.

OO. The method of any one of embodiments A-B, wherein the calcium lactate is provided in a food or nutrient composition comprising calcium lactate.

PP. The method of embodiment 00, wherein the composition is an injectable nutritional supplement.

The foregoing description of the specific embodiments will so fully reveal the general nature of the invention that others can, by applying knowledge within the skill of the art, readily modify and/or adapt for various applications, without departing from the general concept of the invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

REFERENCES

1. Shaw A C, Goldstein D R, Montgomery R R, "Age-dependent dysregulation of innate immunity," Nature Reviews Immunol. 13:875-87 (2013).
2. Sevenoaks M J, Stockley R A, "Chronic Obstructive Pulmonary Disease, inflammation and co-morbidity—a common inflammatory phenotype", Respiratory Res. 7:70 (2006).
3. Hessen M, Akpek E K, "Dry eye: an inflammatory ocular disease," J. Ophthalmic & Vision Res. 9:240-50 (2014).
4. Blanco P, Palucka A K, Pascual V, Banchereau J, "Dendritic cells and cytokines in human inflammatory and autoimmune diseases," Cytokine & Growth Factor Rev. 19:41-52 (2008).
5. Fornoni A, Ijaz A, Tejada T, Lenz 0, "Role of inflammation in diabetic nephropathy," Current Diabetes Rev. 4:10-7 (2008).
6. Minghetti L, "Role of inflammation in neurodegenerative diseases," Current Opinion Neurology 18:315-21 (2005).
7. Kofler S, Nickel T, Weis M, "Role of cytokines in cardiovascular diseases: a focus on endothelial responses to inflammation," Clinical Sci. 108:205-13 (2005).
8. Hotamisligil G S, "Inflammation and metabolic disorders," Nature 444:860-7 (2006).
9. Choy E H, Panayi G S, "Cytokine pathways and joint inflammation in rheumatoid arthritis," New England J. Medicine 344:907-16 (2001).
10. Mundy G R, "Osteoporosis and inflammation," Nutrition Rev. 65:S147-51 (2007).
11. Page R C, Schroeder H E, "Pathogenesis of inflammatory periodontal disease. A summary of current work," Laboratory Investigation 34:235-49 (1976).
12. Tilg H, Moschen A R, "Insulin resistance, inflammation, and non-alcoholic fatty liver disease," Trends in Endocrinology and Metabolism: TEM 19:371-9 (2008).
13. Hamid Q, Boguniewicz M, Leung D Y, "Differential in situ cytokine gene expression in acute versus chronic atopic dermatitis," J. Clinical Investigation 94:870-6 (1994).

14. Arican O, Aral M, Sasmaz S, Ciragil P, "Serum levels of TNF-alpha, IFN-gamma, IL-6, IL-8, IL-12, IL-17, and IL-18 in patients with active psoriasis and correlation with disease severity," Mediators of Inflammation 2005:273-9 (2005).
15. Gilroy D, De Maeyer R, "New insights into the resolution of inflammation," Seminars in Immunology 27:161-8 (2015).
16. Manabe I, "Chronic inflammation links cardiovascular, metabolic and renal diseases," Circulation J. 75:2739-48 (2011).
17. Fujiwara N, Kobayashi K, "Macrophages in inflammation. Current drug targets," Inflammation and Allergy 4:281-6 (2005).
18. Gilmore T D, "Introduction to NF-kappaB: players, pathways, perspectives," Oncogene 25:6680-4 (2006).
19. Karin M, "How NF-kappaB is activated: the role of the IkappaB kinase (IKK) complex," Oncogene 18:6867-74 (1999).
20. Taylor C T, "Interdependent roles for hypoxia inducible factor and nuclear factor-kappaB in hypoxic inflammation," J. Physiology 586:4055-9 (2008).
21. Eltzschig H K, "Carmeliet P. Hypoxia and inflammation," New England J. Medicine 364:656-65(2011).
22. Taylor C T, McElwain J C, "Ancient atmospheres and the evolution of oxygen sensing via the hypoxia-inducible factor in metazoans," Physiology 25:272-9 (2010).
23. Benizri E, Ginouves A, Berra E, "The magic of the hypoxia-signaling cascade. Cellular and molecular life sciences," CMLS 65:1133-49 (2008).
24. Wang G L, Jiang B H, Rue E A, Semenza G L, "Hypoxia-inducible factor 1 is a basic-helix-loop-helix-PAS heterodimer regulated by cellular 02 tension," PNAS USA 92:5510-4 (1995).
25. Barnes P J, Karin M, "Nuclear factor-kappaB: a pivotal transcription factor in chronic inflammatory diseases," New England J. Medicine 336:1066-71 (1997).
26. Whyte M K, Walmsley S R, "The regulation of pulmonary inflammation by the hypoxia-inducible factor-hydroxylase oxygen-sensing pathway," Annals of the American Thoracic Society 11:Supp. 5:S271-6 (2014).
27. Vadlapatla R K, Vadlapudi A D, Mitra A K, "Hypoxia-inducible factor-1 (HIF-1): a potential target for intervention in ocular neovascular diseases," Current Drug Targets 14:919-35 (2013).
28. Mojsilovic-Petrovic J, Callaghan D, Cui H, Dean C, Stanimirovic D B, Zhang W, "Hypoxia-inducible factor-1 (HIF-1) is involved in the regulation of hypoxia-stimulated expression of monocyte chemoattractant protein-1 (MCP-1/CCL2) and MCP-5 (Ccl12) in astrocytes," J. Neuroinflammation 4:12(2007).
29. Medina J, Arroyo A G, Sanchez-Madrid F, Moreno-Otero R, "Angiogenesis in chronic inflammatory liver disease," Hepatology 39:1185-95(2004).
30. Jang J H, Cho Y C, Kim K H, Lee K S, Lee J, Kim D E, et al., "BAI, a novel Cdk inhibitor, enhances farnesyltransferase inhibitor LB42708-mediated apoptosis in renal carcinoma cells through the downregulation of Bcl-2 and c-FLIP (L)," Int. J. Oncology 45:1680-90 (2014).
31. Narrima P, Paydar M, Looi C Y, Wong Y L, Taha H, Wong W F, et al, "*Persea declinata* (Bl.) kosterm bark crude extract induces apoptosis in MCF-7 cells via G0/G1 cell cycle arrest, Bcl-2/Bax/Bcl-xl signaling pathways, and ROS generation," Evidence-Based Complementary and Alternative Medicine 2014: (2014).
32. Genin M, Clement F, Fattaccioli A, Raes M, Michiels C, "M1 and M2 macrophages derived from THP-1 cells differentially modulate the response of cancer cells to etoposide," BMC Cancer 15:577 (2015).
33. Kang S, Park K C, Yang K J, Choi H S, Kim S H, Roh Y J, "Effect of cediranib, an inhibitor of vascular endothelial growth factor receptor tyrosine kinase, in a mouse model of choroidal neovascularization," Clin. Exp. Ophthalmol. 41:63-72 (2013).
34. Roh Y J, Rho C R, Cho W K, Kang S, "The Antiangiogenic Effects of Gold Nanoparticles on Experimental Choroidal Neovascularization in Mice," Investig. Ophthalmol. Vis. Sci. 57:6561-67 (2016).
35. Jiao J, Mo B, Wei H, Jiang Y R, "Comparative study of laser-induced choroidal neovascularization in rats by paraffin sections, frozen sections and high-resolution optical coherence tomography" Graefes Arch. Clin. Expt. Ophthalmol. 251:301-7 (2013).

All publications, patents, and patent applications mentioned in this specification are herein incorporated by reference to the same extent as if each individual publication, patent, or patent application was specifically and individually indicated to be incorporated by reference.

The invention claimed is:

1. A method of treating fibrosis comprising:
administering to a subject in need thereof a pharmaceutical composition comprising:
a therapeutically effective amount of calcium lactate;
a polymer; and
a lipid,
wherein,
the weight ratio of the polymer to the lipid is 1:0.1 to 1:50,
wherein the weight ration of the calcium lactate to the polymer and/or lipid is at least 1.5.

2. The method of claim 1, wherein the fibrosis is liver fibrosis or pulmonary fibrosis.

3. The method of claim 1, wherein the pharmaceutical composition further comprises a pharmaceutically acceptable carrier, excipient, or diluent.

4. The method of claim 1, wherein the pharmaceutical composition is liquid, powder, aerosol, injection, fluid transfusion, patch, capsule, pill, tablet, depot, or suppository.

5. The method of claim 1, wherein a weight ratio of the calcium lactate to the polymer and/or lipid is 1:5 to 1:30.

6. A method of treating fibrosis comprising:
administering to a subject in need thereof a pharmaceutical composition comprising:
a therapeutically effective amount of calcium lactate, wherein
the calcium lactate is coated with a pharmaceutically acceptable enteric coating.

7. The method of claim 6, wherein the enteric coating comprises hydroxypropyl methyl cellulose phthalate (HPMCP), cellulose acetate phthalate (CAP), polyvinyl acetate phthalate (PVAP), shellac, polymer of methacrylic acid and an ester thereof, or combinations thereof.

8. The method of claim 6, wherein the weight ratio of the calcium lactate to the enteric coating is 10:0.5 to 1:1.5.

9. The method of claim 6, wherein the fibrosis disease is liver fibrosis or pulmonary fibrosis.

* * * * *